US010913780B2

(12) United States Patent
Fuselier et al.

(10) Patent No.: US 10,913,780 B2
(45) Date of Patent: Feb. 9, 2021

(54) CONJUGATES, THEIR COMPOSITIONS, THEIR USES, AND THEIR METHODS OF MAKING

(71) Applicant: THE ADMINISTRATORS OF THE TULANE EDUCATIONAL FUND, New Orleans, LA (US)

(72) Inventors: Joseph A. Fuselier, New Orleans, LA (US); David H. Coy, New Orleans, LA (US)

(73) Assignee: THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 191 days.

(21) Appl. No.: 16/087,426

(22) PCT Filed: Mar. 23, 2017

(86) PCT No.: PCT/US2017/023743
§ 371 (c)(1),
(2) Date: Sep. 21, 2018

(87) PCT Pub. No.: WO2017/165607
PCT Pub. Date: Sep. 28, 2017

(65) Prior Publication Data
US 2019/0106473 A1    Apr. 11, 2019

Related U.S. Application Data

(60) Provisional application No. 62/312,751, filed on Mar. 24, 2016.

(51) Int. Cl.
| C07K 14/655 | (2006.01) |
| C07D 498/08 | (2006.01) |
| A61P 37/06 | (2006.01) |
| A61P 19/02 | (2006.01) |
| A61P 1/04 | (2006.01) |
| C07K 14/765 | (2006.01) |
| A61K 47/64 | (2017.01) |
| A61K 47/65 | (2017.01) |

(52) U.S. Cl.
CPC .............. *C07K 14/655* (2013.01); *A61P 1/04* (2018.01); *A61P 19/02* (2018.01); *A61P 37/06* (2018.01); *C07D 498/08* (2013.01); *C07K 14/765* (2013.01); *A61K 47/643* (2017.08); *A61K 47/65* (2017.08)

(58) Field of Classification Search
CPC .. C07K 14/655; C07K 14/765; C07D 498/08; A61P 37/06; A61P 19/02; A61P 1/04; A61K 47/643; A61K 47/65
See application file for complete search history.

(56) References Cited

U.S. PATENT DOCUMENTS

| 4,554,101 A | 11/1985 | Hopp |
| 5,604,234 A | 2/1997 | Or et al. |
| 5,922,729 A | 7/1999 | Chang et al. |
| 7,078,495 B1 | 7/2006 | Kasper et al. |
| 7,307,148 B2 | 12/2007 | Bousquet-Gagnon et al. |
| 7,605,257 B2 | 10/2009 | Gu et al. |
| 7,771,727 B2 | 8/2010 | Fuselier et al. |
| 2005/0176080 A1 | 8/2005 | Bodepudi et al. |
| 2011/0020343 A1 | 1/2011 | Senter et al. |
| 2011/0064753 A1 | 3/2011 | Senter et al. |
| 2011/0070248 A1 | 3/2011 | Ichikawa et al. |
| 2011/0097322 A1 | 4/2011 | Alley et al. |
| 2015/0314015 A1* | 11/2015 | Leamon .................... A61P 9/10 514/1.9 |

FOREIGN PATENT DOCUMENTS

| EP | 1206493 B1 | 11/2006 |
| WO | 99/03860 A1 | 1/1999 |
| WO | 03/028527 A2 | 4/2003 |
| WO | 03/074551 A2 | 9/2003 |
| WO | 2005/094895 A1 | 10/2005 |
| WO | 2011/079227 A1 | 6/2011 |
| WO | 2012/112792 A2 | 8/2012 |
| WO | 2015/095755 A1 | 6/2015 |

OTHER PUBLICATIONS

International Search Report from PCT/US2017/023743 dated May 26, 2017, 3 pages.
Written Opinion from PCT/US2017/023743 dated May 26, 2017, 5 pages.
Ballantyne et al., (1971) "Albumin metabolism in rheumatoid arthritis." Annals of the rheumatic diseases, vol. 30, No. 3, pp. 265-270.
Becker et al., (1999) "32-Indolyl Ether Derivatives of Ascomycin: Three-Dimensional Structures of Complexes with FK506-Binding Protein" J. Med. Chem., vol. 42, pp. 2798-2804.
Briesewitz et al., (1999) "Affinity modulation of small-molecule ligands by borrowing endogenous protein surfaces" Proc. Natl. Acad. Sci. USA, vol. 96, No. 5, pp. 1953-1958.

(Continued)

*Primary Examiner* — Sudhakar Katakam
(74) *Attorney, Agent, or Firm* — ALGM LLP; Harry J. Guttman

(57) ABSTRACT

Some embodiments of the invention include inventive compounds (e.g., compounds of Formula (I)) including but not limited to conjugates comprising FK-506 and ascomycin. Other embodiments include compositions (e.g., pharmaceutical compositions) comprising the inventive compound. Still other embodiments of the invention include compositions for treating, for example, certain diseases using the inventive compounds. Some embodiments include methods of using the inventive compound (e.g., in compositions or in pharmaceutical compositions) for administering and treating. Further embodiments include methods for making the inventive compound. Additional embodiments of the invention are also discussed herein.

63 Claims, 11 Drawing Sheets
Specification includes a Sequence Listing.

(56) References Cited

OTHER PUBLICATIONS

Canadas et al., (2005) "Equilibrium studies of a fluorescent tacrolimus binding to surfactant protein A" Analytical Biochemistry, vol. 340, pp. 57-65.
Denzler et al., (1999) "Expression of Somatostatin Receptors in Peritumoral Veins of Human Tumors" Cancer, vol. 85, No. 1, pp. 188-198.
Du et al., (2014) "Drug carriers for the delivery of therapeutic peptides" Biomacromol., vol. 15, pp. 1097-1114.
Ducry, Laurent, ed. Antibody-drug conjugates. Humana Press, 2013.
Elsadek et al., (2012) "Impact of albumin on drug delivery—new applications on the horizon." J. Cont. Rel., vol. 157, No. 1, pp. 4-28.
Erickson et al., (2006) "Antibody-Maytansinoid Conjugates Are Activated in Targeted Cancer Cells by Lysosomal Degradation and Linker-Dependent Intracellular Processing" Cancer Res., vol. 66, No. 8, pp. 4426-4433.
Erickson et al., (2010) "Tumor Delivery and In Vivo Processing of Disulfide-Linked and Thioether-Linked Antibody-Maytansinoid Conjugates" Bioconjugate chemistry, vol. 21, No. 1, pp. 84-92.
Fiehn et al., (2004a) "Albumin-coupled methotrexate (MTX-HSA) is a new anti-arthritic drug which acts synergistically to MTX" Rheumatology vol. 43, pp. 1097-1105.
Fiehn et al., (2004b) "Methotrexate (MTX) and albumin coupled with MTX (MTX-HSA) suppress synovial fibroblast invasion and cartilage degradation in vivo" Annals of the rheumatic diseases, vol. 63, pp. 884-886.
Fleischmann et al., (2006) "Tacrolimus in rheumatoid arthritis" Expert Opin. Pharmacother., vol. 7, pp. 91-98.
Griessinger et al. (2015) "64Cu antibody-targeting of the T-cell receptor and subsequent internalization enables in vivo tracking of lymphocytes by PET" Proc Natl Acad Sci., vol. 112, pp. 1161-1166 (with supporting information).
Hermanson, Bioconjugate Techniques, 3rd edition (2013) Chapters 2 and 3, Academic Press, Oxford. (2 pdfs).
Kratz (2008) "Albumin as a drug carrier: design of prodrugs, drug conjugates and nanoparticles." Journal of Controlled Release, vol. 132, No. 3, pp. 171-183.
Kratz et al., (2012) "Clinical impact of serum proteins on drug delivery" Journal of Controlled Release, vol. 161, Issue 2, pp. 429-445.
Kyte et al., (1982) "A Simple Method for Displaying the Hydropathic Character of a Protein" J. Mol. Biol., vol. 157, pp. 105-132.
Lukinius et al., (1999) "In vivo cellular distribution and endocytosis of the somatostatin receptor-ligand complex." Acta Onc., vol. 38, No. 3, pp. 383-387.
Patel et al., (2012) "Formulation strategies for drug delivery of tacrolimus: An overview" International Journal of Pharmaceutical Investigation, vol. 2, No. 4, pp. 169-175.
Reubi (2003) "Peptide Receptors as Molecular Targets for Cancer Diagnosis and Therapy" Endocrine Rev., vol. 24, No. 4, pp. 389-427.
Roivainen et al., (2012) "Gallium-labelled peptides for imaging of inflammation." European journal of nuclear medicine and molecular imaging, vol. 39, No. 1, pp. S68-S77.
Rooseboom et al., (2004) "Enzyme-Catalyzed Activation of Anticancer Prodrugs" Pharmacol. Rev., vol. 56, No. 1, pp. 53-102.
Sawada et al., (1987) "Novel Immunosuppressive Agent. FK506/In Vitro Effects on the cloned T Cell Activation" J. Immunol., vol. 139, No. 6, pp. 1797-1803.
Schaer et al., (1997) "Somatostatin receptor subtypes sst1, sst2, sst3 and sst5 expression in human pituitary, gastroentero-pancreatic and mammary tumors: comparison of mRNA analysis with receptor autoradiography." Int. J. Cancer, vol. 70, No. 5, pp. 530-537.
Signore et al., (2011) "The molecular imaging approach to image infections and inflammation by nuclear medicine techniques." Annals of nuclear medicine, vol. 25, No. 10, pp. 681-700.
Thorpe et al., (1987) "New coupling agents for the synthesis of immunotoxins containing a hindered disulfide bond with improved stability in vivo." Cancer research, vol. 47, No. 22, pp. 5924-5931.
Wunder et al., (2003) "Albumin-based drug delivery as novel therapeutic approach for rheumatoid arthritis." Arthritis Res Ther, vol. 5, Suppl 3, p. S4 abstract No. 9.

* cited by examiner

A

Chemical Formula: $C_{79}H_{123}N_{11}O_{28}S_2$
Molecular Weight: 1739.02

B

Chemical Formula: $C_{74}H_{119}BrN_{10}O_{26}S_2$
Molecular Weight: 1708.83

C

Chemical Formula: $C_{95}H_{143}N_{15}O_{40}S_2$
Molecular Weight: 2199.37

D

Chemical Formula: $C_{90}H_{139}BrN_{14}O_{38}S_2$
Molecular Weight: 2169.19

SEQUENCE LISTING

```
<160> NUMBER OF SEQ ID NOS: 9

<210> SEQ ID NO 1
<211> LENGTH: 9
<212> TYPE: PRT
<213> ORGANISM: Artificial Sequence
<220> FEATURE:
<223> OTHER INFORMATION: Related to Inflame target 1

<400> SEQUENCE: 1

Gly Gly Gly Gly Lys Gly Gly Gly Gly
1               5

<210> SEQ ID NO 2
<211> LENGTH: 17
<212> TYPE: PRT
<213> ORGANISM: Artificial Sequence
<220> FEATURE:
<223> OTHER INFORMATION: Related to Inflame target 2

<400> SEQUENCE: 2

Cys Ala Arg Leu Ser Leu Ser Trp Arg Gly Leu Thr Leu Cys Pro Ser
1               5                   10                  15

Lys

<210> SEQ ID NO 3
<211> LENGTH: 14
<212> TYPE: PRT
<213> ORGANISM: Artificial Sequence
<220> FEATURE:
<223> OTHER INFORMATION: Related to Somatostatin

<400> SEQUENCE: 3

Ala Gly Cys Lys Asn Phe Phe Trp Lys Thr Phe Thr Ser Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Related to Bombesin
<220> FEATURE:
<221> NAME/KEY: misc_feature
<222> LOCATION: (1)..(1)
<223> OTHER INFORMATION: Pyroglutamic acid

<400> SEQUENCE: 4

Xaa Gln Arg Leu Gly Asn Gln Trp Ala Val Gly His Leu Met
1               5                   10

<210> SEQ ID NO 5
<211> LENGTH: 32
<212> TYPE: PRT
<213> ORGANISM: Artificial Sequence
<220> FEATURE:
<223> OTHER INFORMATION: Related to Neuromedin B

<400> SEQUENCE: 5

Thr Pro Phe Ser Trp Asp Leu Pro Glu Pro Arg Ser Arg Ala Ser Lys
1               5                   10                  15

Ile Arg Val His Pro Arg Gly Asn Leu Trp Ala Thr Gly His Phe Met
                20                  25                  30
```

```
<210> SEQ ID NO 6
<211> LENGTH: 10
<212> TYPE: PRT
<213> ORGANISM: Artificial Sequence
<220> FEATURE:
<223> OTHER INFORMATION: Related to Neuromedin B 23-32

<400> SEQUENCE: 6

Gly Asn Leu Trp Ala Thr Gly His Phe Met
1               5                   10

<210> SEQ ID NO 7
<211> LENGTH: 27
<212> TYPE: PRT
<213> ORGANISM: Artificial Sequence
<220> FEATURE:
<223> OTHER INFORMATION: Related to Gastrin-releasing peptide

<400> SEQUENCE: 7

Val Pro Leu Pro Ala Gly Gly Gly Thr Val Leu Thr Lys Met Tyr Pro
1               5                   10                  15

Arg Gly Asn His Trp Ala Val Gly His Leu Met
            20                  25

<210> SEQ ID NO 8
<211> LENGTH: 10
<212> TYPE: PRT
<213> ORGANISM: Artificial Sequence
<220> FEATURE:
<223> OTHER INFORMATION: Related to Neuromedin C

<400> SEQUENCE: 8

Gly Ser His Trp Ala Val Gly His Leu Met
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Related to Bombesin analog

<400> SEQUENCE: 9

Gly Asn His Trp Ala Val Gly His Leu Met
1               5                   10
```

CONJUGATES, THEIR COMPOSITIONS, THEIR USES, AND THEIR METHODS OF MAKING

CROSS-REFERENCE TO RELATED APPLICATIONS

This application is a National Stage Entry of International Application No. PCT/US2017/023743 filed Mar. 23, 2017, entitled "CONJUGATES OF TACROLIMUS, THEIR COMPOSITIONS, AND THEIR USES" which is herein incorporated by reference in its entirety, and which claims the benefit of U.S. Provisional Application No. 62/312,751, filed Mar. 24, 2016, entitled "CONJUGATES, THEIR COMPOSITIONS, AND THEIR USES" which is herein incorporated by reference in its entirety claims the benefit of U.S. Provisional Application No. 62/312,751 filed Mar. 24, 2016, which is herein incorporated by reference in its entirety.

BACKGROUND

Tacrolimus (also known as FK-506) can act as an immunosuppressant. This has led to some medical uses of FK-506. FK-506 can sometimes have unintended side-effects including, for example, impaired kidney function, hypertension, tremor, dyspepsia, abdominal pain, nausea, headache, and diarrhea. FK-506 is hydrophobic which can sometimes result in difficulties in administration. Certain embodiments of the invention can address one or more of the deficiencies discussed above.

Some embodiments of the invention include inventive compounds (e.g., compounds of Formula (I)) including but not limited to conjugates comprising FK-506 and similar compounds. Other embodiments include compositions (e.g., pharmaceutical compositions) comprising the inventive compound. Still other embodiments of the invention include compositions for treating, for example, certain diseases using the inventive compounds. Some embodiments include methods of using the inventive compound (e.g., in compositions or in pharmaceutical compositions) for administering and treating. Further embodiments include methods for making the inventive compound. Additional embodiments of the invention are also discussed herein.

SUMMARY

Some embodiments of the present invention include a compound selected from Formula (I) salts, optical isomers, geometric isomers, salts of isomers, and derivatives thereof, where $R_1$ is H, allyl, vinyl, hydroxyl, Cl, Br, F, I, thiol, amino, nitro, cyano, branched or unbranched $C_1$-$C_4$, alkyl, branched or unbranched $C_1$-$C_4$ alkylnoic, phenyl, $C_1$-$C_2$ perfluorinated alkyl, alkyl amino, oxo, carboxy, acetyl, amido, or $C_1$-$C_3$ akloxy; $R_2$ is H, allyl, vinyl, hydroxyl, Cl, Br, F, I, thiol, amino, nitro, cyano, branched or unbranched $C_1$-$C_4$ alkyl, branched or unbranched $C_1$-$C_4$ alkylnoic, phenyl, $C_1$-$C_2$ perfluorinated alkyl, alkyl amino, oxo, carboxy, acetyl, amido, or $C_1$-$C_3$ akloxy; X is a substituted or unsubstituted $C_4$-$C_{12}$ conjugated cyclic hydrocarbon or

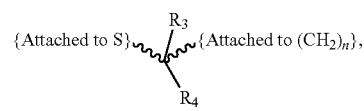

where $R_3$ and $R_4$ can be the same or different and are H or a substituted or unsubstituted, branched or unbranched bivalent $C_1$-$C_{11}$ alkyl; n is 0, 1, 2, 3, 4, or 5; m is 1, 2, 3, 4, or 5; Y is an amino acid sequence of no more than about 30 amino acids; and Z is targeting amino acid sequence, a stabilizing amino acid sequence, or both. In certain embodiments, $R_1$ is H, allyl, ethyl, methyl, or OH. In other embodiments, $R_2$ is H, allyl, ethyl, methyl, or OH. In yet other embodiments, X is a bivalent benzene or a bivalent substituted or unsubstituted $C_4$-$C_{12}$ conjugated cyclic hydrocarbon. In some embodiments, X is an unsubstituted $C_1$ or

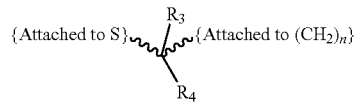

and $R_3$ and $R_4$ can be the same or different and are H or an unsubstituted, branched or unbranched $C_1$-$C_3$ alkyl. In certain embodiments, n is 0 or 1. While in some embodiments, m is 1 or 2. In other embodiments, the number of amino acids in Y is from about 2 to about 30, from about 4 to about 20, from about 5 to about 17, or from about 7 to about 15. In certain instances, the percentage of D-amino acids in Y is at least about 25%, at least about 50%, at least about 75%, no more than about 25%, no more than about 50%, or no (I)

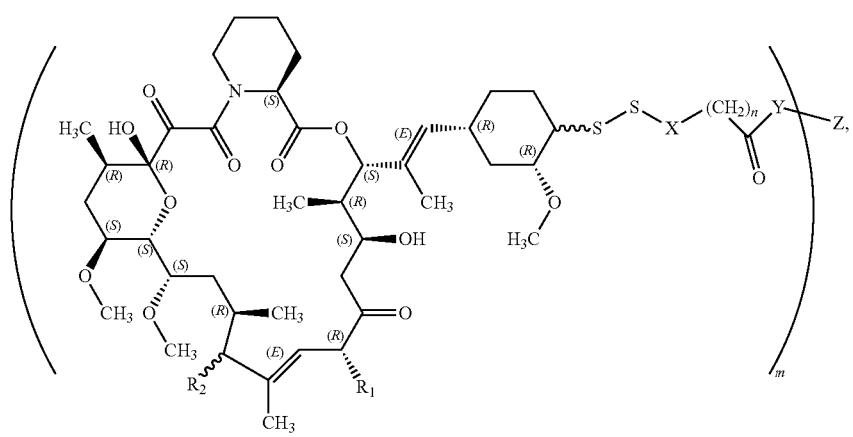

more than about 75%. In other embodiments, the percentage of L-amino acids in Y can be at least about 25%, at least about 50%, at least about 75%, no more than about 25%, no more than about 50%, or no more than about 75%. Further embodiments include where Y has 2, 3, 4, or 5 successive L-amino acids, or has 2, 3, 4, or 5 successive D-amino acids. In other embodiments, at least some successive amino acids in Y alternate D-forms and L-forms. Still other embodiments include where Y does not self assemble or have secondary structure. In certain embodiments, Y is DAsp-Asp-DAsp-Asp-DSer-Ser-Thr-Ser-DSer-Lys-DSer-NH$_2$, DSer-Ser-DSer-Ser-DSer-Nle-DTyr-DSer-Cys-Phe-DTrp-Lys-Thr-Cys-Thr-NH$_2$, or DSer-Ser-Thr-Ser-DSer-Lys-DSer-NH$_2$. In some embodiments, Z is no more than about 2500 amino acids, Z has a molecular mass of no more than about 300,000, or both. In yet other embodiments, Z is a protein, a mutated protein, a fragment of the protein or a fragment of the mutated protein. In still other embodiments, Z targets cells related to inflammation, organs, or combinations thereof. Other embodiments include where Z targets T cells, cytotoxic T cells, helper T cells, activated T-cells, differentiated T-cells, effector cells, transplanted organs, organs undergoing hyperacute rejection, organs undergoing acute rejection, organs undergoing chronic rejection, organs, tissues or cells associated with autoimmune diseases, organs, tissues or cells associated with inflammation, organs or tissues that are inflamed, or combinations thereof. In other embodiments, Z targets transplanted organs, organs undergoing hyperacute rejection, organs undergoing acute rejection, organs undergoing chronic rejection, or combinations thereof. In still other embodiments, Z targets organs, tissues or cells associated with autoimmune diseases or combinations thereof. And some embodiments include where Z targets organs, tissues or cells associated with autoimmune diseases or combinations thereof, and the autoimmune disease is arthritis, osteoarthritis, or rheumatoid arthritis. In other embodiments, Z is a somatostatin, a somatostatin analog, a bombesin, a bombesin analog, an antibody, a polyclonal antibody, a monoclonal antibody, a polyclonal antibody that targets T-cells, a monoclonal antibody that targets T-cells, a polyclonal antibody that targets Vascular adhesion protein 1, a monoclonal antibody that targets Vascular adhesion protein 1, a peptide that targets inflamed endothelial cells, a peptide that targets integrin $\alpha_v\beta_3$, murine-based antibodies, besilesomab, fanolesomab, sulesomab, antimicrobial peptides, human lactoferrin, ubiquicidin, the ubiquicidin 29-41 peptide fragment, human neutrophil peptide 1-3, annexin-V, IL-2, IL-12, monoclonal antibodies to TNFα, infliximab, adalimumab, monoclonal antibodies to CD4, monoclonal antibodies to CD20, monoclonal antibodies to CD3, KJ1-26 monoclonal antibodies, transferrin, an albumin, human serum albumin (HSA), Domain I of HSA, Domain II of HSA, Domain III of HSA, bovine serum albumin (BSA), an engineered albumin, mutants thereof or fragments thereof. In some embodiments Z is BSA, HSA, or transferrin. In other embodiments, Z comprises a stabilizing amino acid sequence. In some instances, the targeting amino acid sequence overlaps with the stabilizing amino acid sequence, the targeting amino acid sequence encompasses the stabilizing amino acid sequence, the targeting amino acid sequence is the same as the stabilizing amino acid sequence, or the targeting amino acid sequence does not overlap with the stabilizing amino acid sequence. In some embodiments, the stabilizing amino acid sequence is an albumin, human serum albumin (HSA), Domain I of HSA, Domain II of HSA, Domain III of HSA, bovine serum albumin (BSA), an engineered albumin, a casein, an insulin, a hemoglobin, a lysozyme, an α-2-macroglobulin, a fibronectin, a vitronectin, a fibrinonectin, a lipase, mutants thereof, or fragments thereof. In other embodiments, the stabilizing amino acid sequence is BSA or HSA.

In some instances, (a) $R_1$ is allyl; $R_2$ is methyl; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;

(b) $R_1$ is allyl; $R_2$ is methyl; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;

(c) $R_1$ is allyl; $R_2$ is methyl; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is somatostatin;

(d) $R_1$ is allyl; $R_2$ is methyl; X is bivalent benzene; n is 1; m is 1; Y is DSer-Ser-Thr-Ser-DSer-Lys-DSer-NH$_2$; and Z is BSA or HSA;

(e) $R_1$ is allyl; $R_2$ is methyl; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$;

(f) $R_1$ is allyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;

(g) $R_1$ is allyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;

(h) $R_1$ is allyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is somatostatin;

(i) $R_1$ is allyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is BSA or HSA;

(j) $R_1$ is allyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$;

(k) $R_1$ is ethyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;

(l) $R_1$ is ethyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;

(m) $R_1$ is ethyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is somatostatin;

(n) R₁ is ethyl; R₂ is H; X is bivalent benzene; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂; and Z is BSA or HSA;

(o) R₁ is ethyl; R₂ is H; X is bivalent benzene; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂; and Z is DSer-Ser-DSer-Ser-DSer-Nle-DTyr-DSer-Cys-Phe-DTrp-Lys-Thr-Cys-Thr-NH₂.

(p) R₁ is allyl; R₂ is methyl; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂, where the side-chain amino of Lys in Y is modified with a maleimide; and Z is BSA or HSA;

(q) R₁ is allyl; R₂ is methyl; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂, where the side-chain amino of Lys in Y is modified with a bromoacetamide; and Z is BSA or HSA;

(r) R₁ is allyl; R₂ is methyl; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂; and Z is somatostatin;

(s) R₁ is allyl; R₂ is methyl; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂; and Z is BSA or HSA;

(t) R₁ is allyl; R₂ is methyl; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂; and Z is DSer-Ser-DSer-Ser-DSer-Nle-DTyr-DSer-Cys-Phe-DTrp-Lys-Thr-Cys-Thr-NH₂;

(u) R₁ is allyl; R₂ is H; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂, where the side-chain amino of Lys in Y is modified with a maleimide; and Z is BSA or HSA;

(v) R₁ is allyl; R₂ is H; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂, where the side-chain amino of Lys in Y is modified with a bromoacetamide; and Z is BSA or HSA;

(w) R₁ is allyl; R₂ is H; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂; and Z is somatostatin;

(x) R₁ is allyl; R₂ is H; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂; and Z is BSA or HSA;

(y) R₁ is allyl; R₂ is H; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂; and Z is DSer-Ser-DSer-Ser-DSer-Nle-DTyr-DSer-Cys-Phe-DTrp-Lys-Thr-Cys-Thr-NH₂;

(z) R₁ is ethyl; R₂ is H; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂, where the side-chain amino of Lys in Y is modified with a maleimide; and Z is BSA or HSA;

(aa) R₁ is ethyl; R₂ is H; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂, where the side-chain amino of Lys in Y is modified with a bromoacetamide; and Z is BSA or HSA;

(bb) R₁ is ethyl; R₂ is H; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂; and Z is somatostatin;

(cc) R₁ is ethyl; R₂ is H; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂; and Z is BSA or HSA; or (dd) R₁ is ethyl; R₂ is H; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂; and Z is DSer-Ser-DSer-Ser-DSer-Nle-DTyr-DSer-Cys-Phe-DTrp-Lys-Thr-Cys-Thr-NH₂.

In some embodiments, the compound is where the attachment to the HSA is via an HSA cysteine thiol or via an HSA amine;

where the attachment to the HSA is via an HSA cysteine thiol or via an HSA amine;

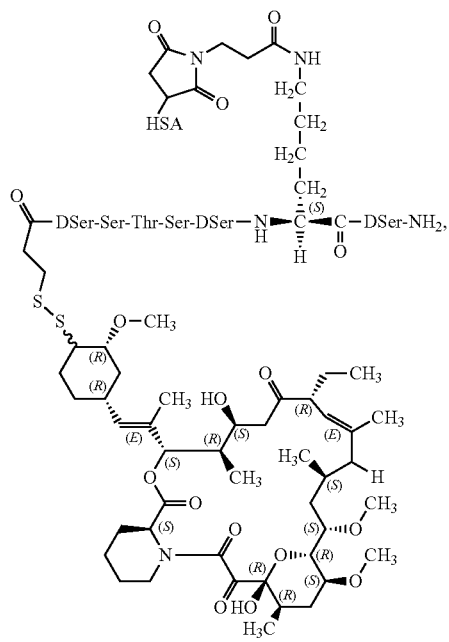
where the attachment to the HSA is via an HSA cysteine thiol or via an HSA amine;
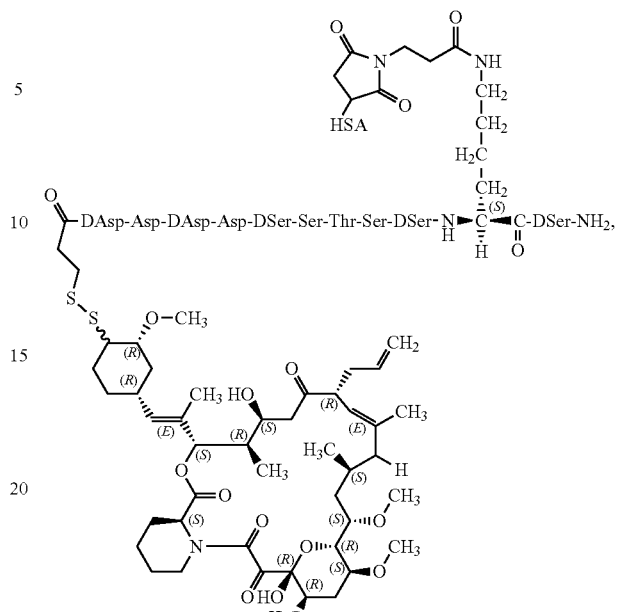
where the attachment to the HSA is via an HSA cysteine thiol or via an HSA amine;
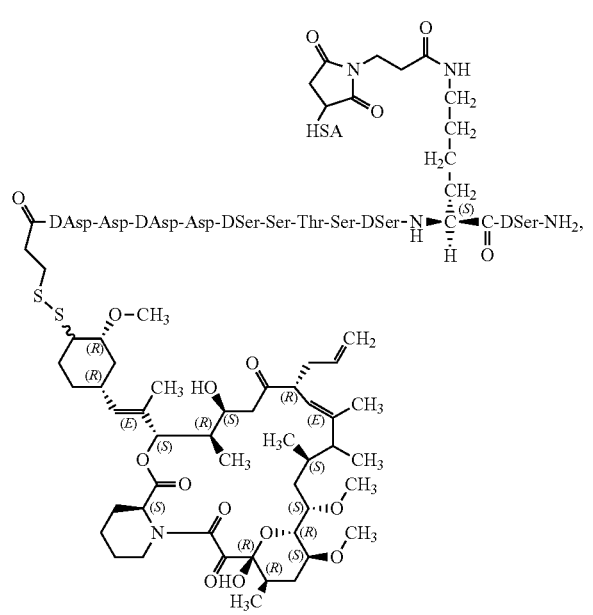
where the attachment to the HSA is via an HSA cysteine thiol or via an HSA amine;
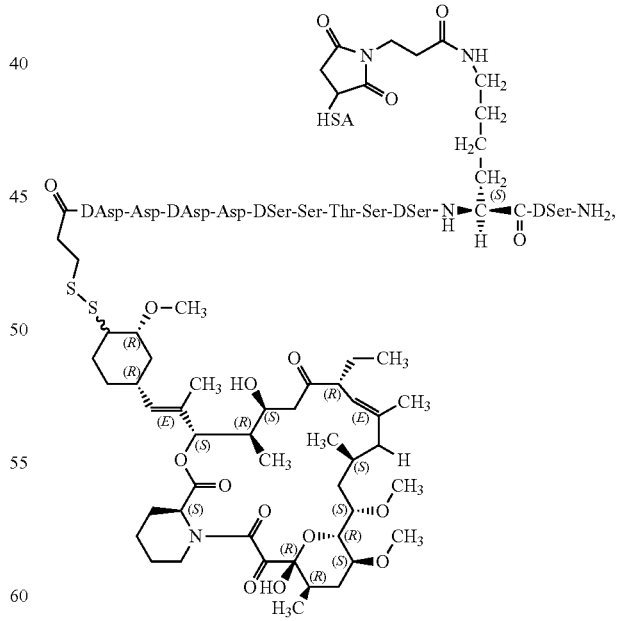
where the attachment to the HSA is via an HSA cysteine thiol or via an HSA amine;

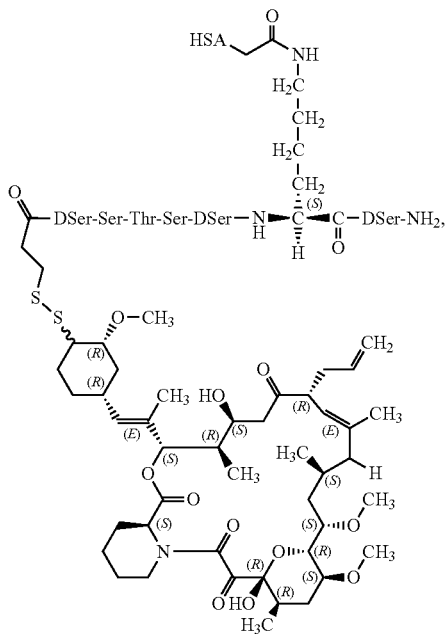
where the attachment to the HSA is via an HSA cysteine thiol or via an HSA amine;
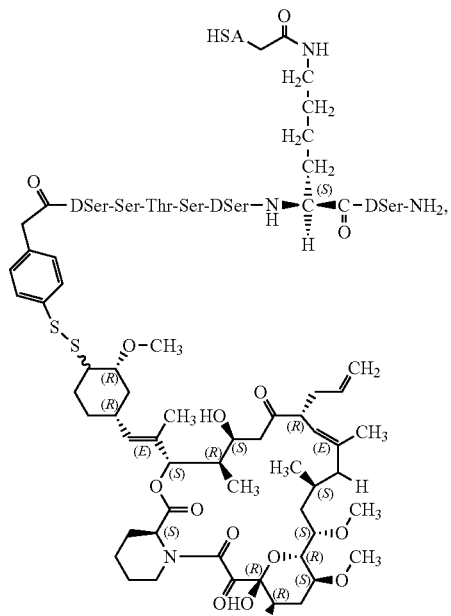
where the attachment to the HSA is via an HSA cysteine thiol or via an HSA amine;
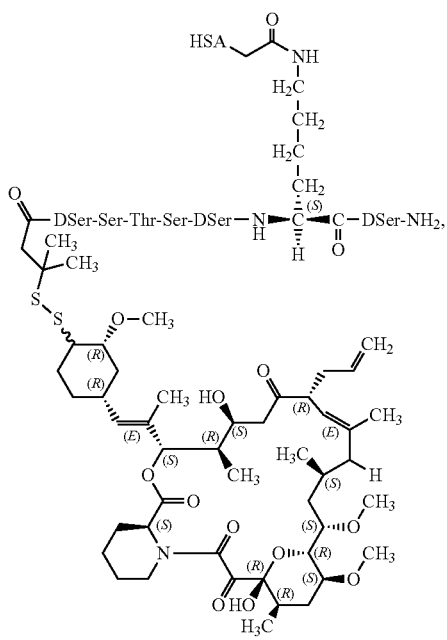
where the attachment to the HSA is via an HSA cysteine thiol or via an HSA amine;
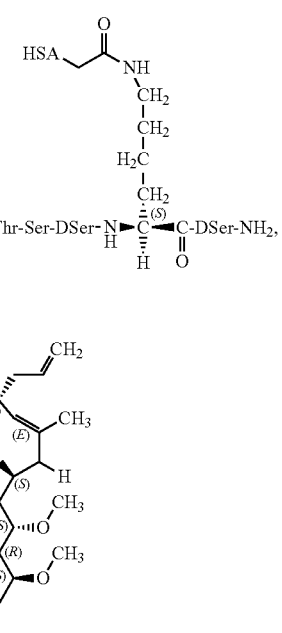
where the attachment to the HSA is via an HSA cysteine thiol or via an HSA amine;

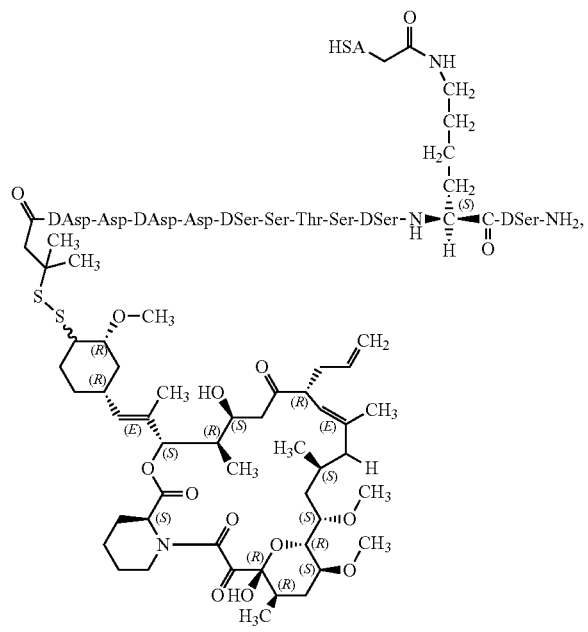
where the attachment to the HSA is via an HSA cysteine thiol or via an HSA amine;
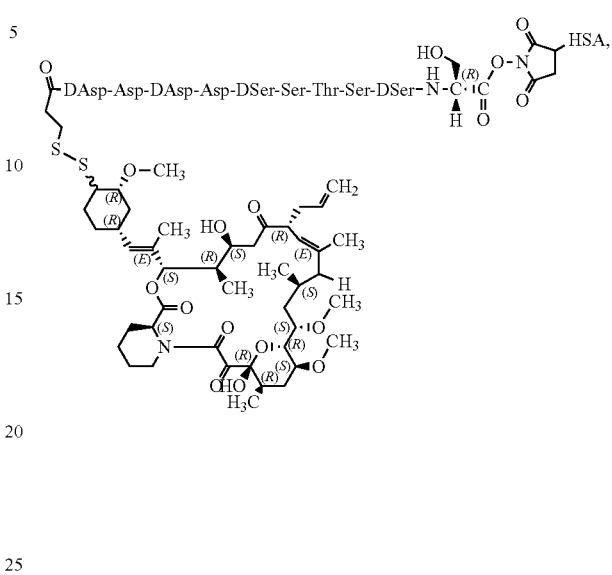
where the attachment to the HSA is via an HSA cysteine thiol or via an HSA amine;
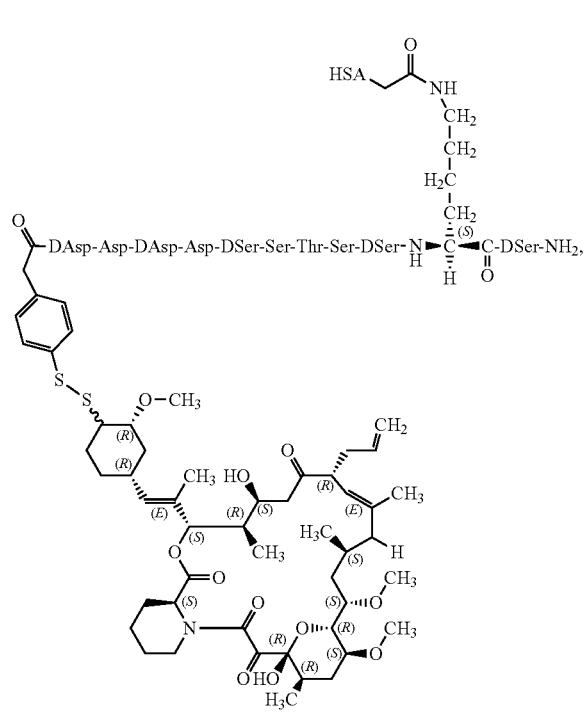
where the attachment to the HSA is via an HSA cysteine thiol or via an HSA amine;
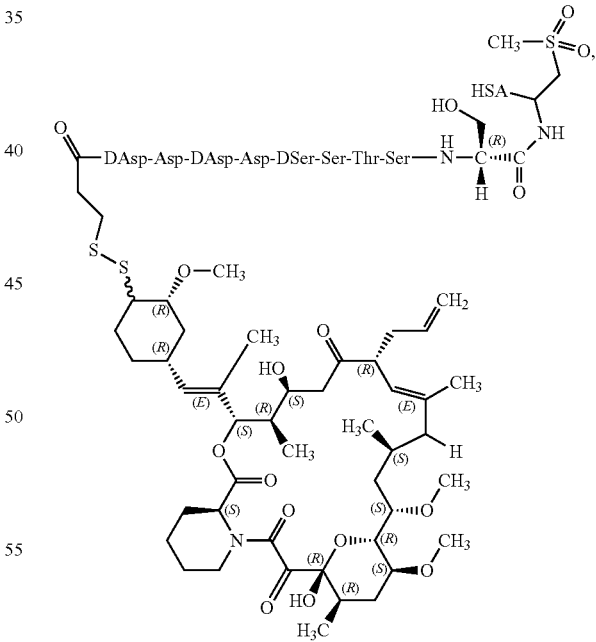
where the attachment to the HSA is via an HSA cysteine thiol or via an HSA amine; or

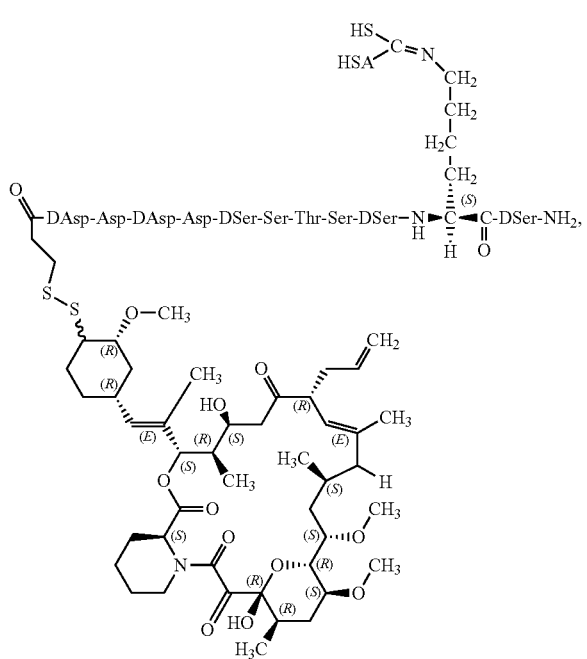

where the attachment to the HSA is via an HSA cysteine thiol or via an HSA amine.

Some embodiments of the present include compositions comprising any compound disclosed herein (e.g., a compound of Formula (I)). In other embodiments, the amount of the compound in the composition is from about 0.0001% (by weight total composition) to about 99%.

Other embodiments of the present invention include pharmaceutical compositions comprising any compound disclosed herein (e.g., a compound of Formula (I)). In some embodiments, the amount of the compound in the pharmaceutical composition is from about 0.0001% (by weight total composition) to about 50%. In still other embodiments, the pharmaceutical composition further comprises a formulary ingredient.

Other embodiments of the present invention include methods for providing an animal with any compound disclosed herein (e.g., a compound of Formula (I)) comprising one or more administrations of one or more compositions comprising the compound, wherein the compositions may be the same or different if there is more than one administration. In some embodiments, at least one of the one or more compositions further comprises a formulary ingredient. In other embodiments, at least one of the one or more compositions comprises any composition disclosed herein or any pharmaceutical composition disclosed herein. In some embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In some instances, if there is more than one administration at least one composition used for at least one administration is different from the composition of at least one other administration. In still other embodiments, the compound of at least one of the one or more compositions is administered to the animal in an amount of from about 0.01 mg/kg animal body weight to about 15 mg/kg animal body weight. In some embodiments, the animal is a human, canine, or a primate.

Some embodiments of the present invention include methods for treating an animal for an autoimmune disease or for organ rejection, comprising one or more administrations of one or more compositions comprising any compound disclosed herein (e.g., a compound of Formula (I)), wherein the compositions may be the same or different if there is more than one administration. In some embodiments, at least one of the one or more compositions further comprises a formulary ingredient. In other embodiments, at least one of the one or more compositions comprises the composition of any composition disclosed herein or the pharmaceutical composition of any pharmaceutical composition disclosed herein. In still other embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In some embodiments, if there is more than one administration at least one composition used for at least one administration is different from the composition of at least one other administration. In other embodiments, the compound of at least one of the one or more compositions is administered to the animal in an amount of from about 0.01 mg/kg animal body weight to about 15 mg/kg animal body weight. In some instances, the animal is a human, canine, or a primate. In some embodiments, the animal is in need of the treatment. In still other embodiments, the method is for treating organ rejection for an allograft transplantation or for a xenograft transplantation. In yet other embodiments, the method is for treating organ rejection for a liver transplant, a kidney transplant, or a heart transplant. In some instances, the method is for treating ulcerative colitis, inflammatory bowel disease, Crohn's disease arthritis, osteoarthritis, or rheumatoid arthritis. In yet other embodiments, the animal is susceptible to an autoimmune disease or to an organ rejection. In certain embodiments, the method prevents or ameliorates future autoimmune disease or future organ rejection.

Some embodiments of the present invention include methods for preparing any compound disclosed herein (e.g., a compound of Formula (I)) comprising, (a) reacting a compound of Formula (II)

(II)

[Chemical structure of Formula (II)]

with a W amino acid sequence, where one or more amino acids of W comprises one or more protecting groups and W is attached to a solid support via W's C-terminal amino acid;

(b) optionally removing one or more protecting groups from W;

(c) optionally modifying one of the W amino acids;

(d) cleaving the bond which connects the C-terminal amino acid of W to the solid support to produce a removed compound;

(e) attaching the removed compound to Z, if the removed compound does not include Z; and (f) recovering the compound;

where the W amino acid sequence without its one or more protecting groups is identical to (1) a Y' amino acid sequence, (2) a Y amino acid sequence, (3) a (Y—Z)' amino acid sequence, or (4) a Y—Z amino acid sequence; the Y' amino acid sequence is a pre-modified Y amino acid sequence; and the (Y—Z)' amino acid sequence is a pre-modified Y—Z amino acid sequence. In some embodiments, the method further comprises the step of removing all protecting groups from W after step (d) and before step (f). In other embodiments, the method further comprises the step of removing all protecting groups from W after step (d) and before step (e). In certain embodiments, the method further comprises the step of removing all protecting groups from W during step (d). In yet other embodiments, the removed compound in step (d) does not include Z. In other embodiments, step (b) is not optional. In still other embodiments, steps (b) and (c) are not optional. In some embodiments, steps (b) and (c) are not optional and the modifying of step (c) results in a Lys amino side chain being modified with a maleimide or with a bromoacetamide. In other embodiments, the solid support is a polystyrene resin. In some embodiments, the carboxy group adjacent to $(CH_2)_n$ in Formula (II) is activated.

Other embodiments of the invention are also disclosed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
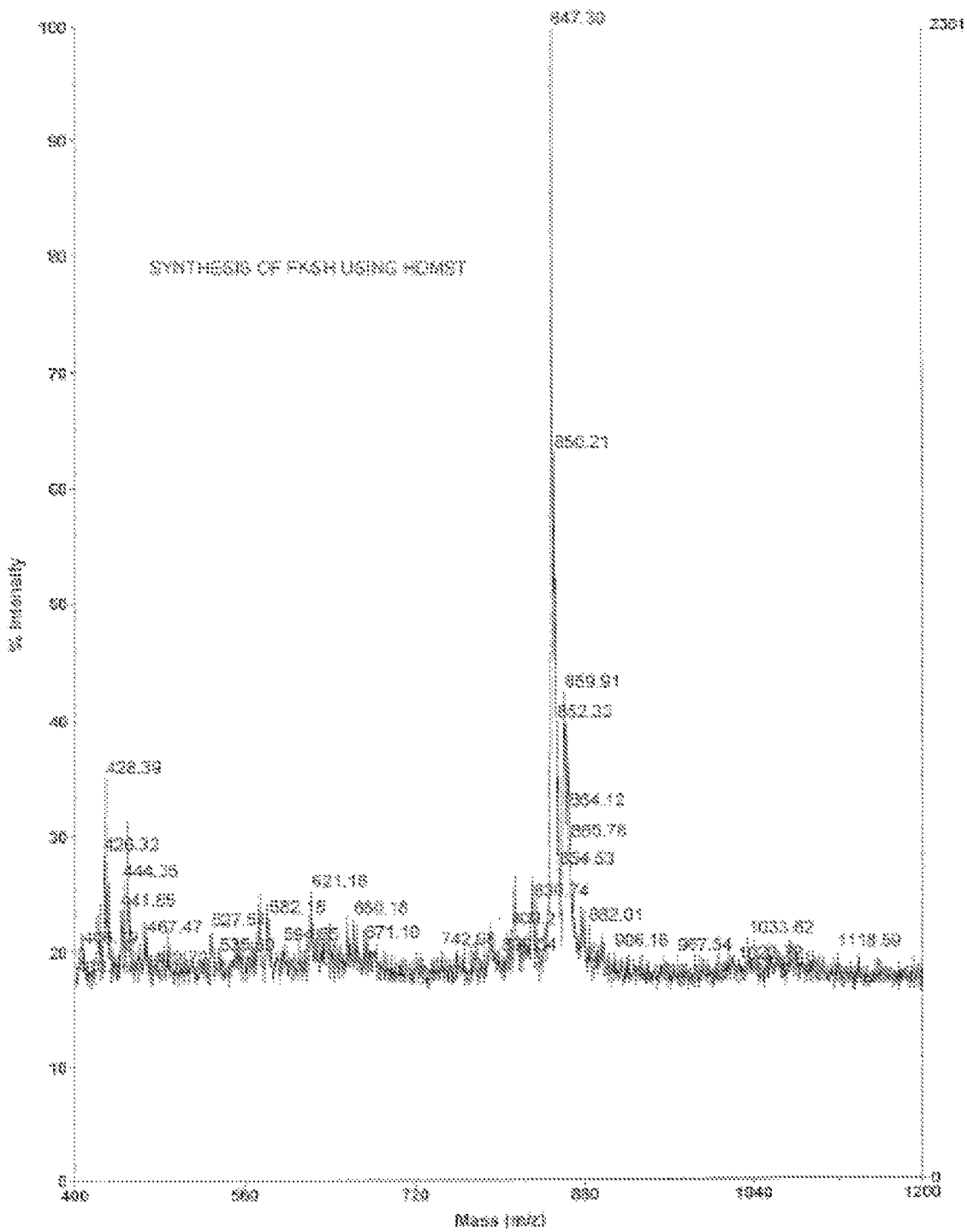
FIG. 1. The Mass Spectrometry data of tacrolimus-32-thiol, as discussed in Example 2.

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include inventive compounds (e.g., compounds of Formula (I)) including but not limited to conjugates comprising FK-506 and similar compounds. Other embodiments include compositions (e.g., pharmaceutical compositions) comprising the inventive compound. Still other embodiments of the invention include compositions for treating, for example, certain diseases using the inventive compounds. Some embodiments include methods of using the inventive compound (e.g., in compositions or in pharmaceutical compositions) for administering and treating. Further embodiments include methods for making the inventive compound.

As defined herein "amino acids" include but are not limited to any naturally occurring amino acids (including but not limited to the standard 20 amino acids which are Gly, Ala, Val, Leu, Ile, Met, Pro, Phe, Trp, Ser, Thr, Asn, Gln, Tyr, Cys, Lys, Arg, His, Asp, and Glu) and unusual amino acids. As defined herein, "unusual amino acids" are amino acids that are not one of the standard 20 amino acids. Some examples of unusual amino acids are listed in Table A, but are not limited to those listed in Table A.

TABLE A

| Abbr. | Amino Acid |
|---|---|
| | Unusual Amino Acids |
| Aad | 2-Aminoadipic acid |
| BAad | 3-Aminoadipic acid |
| BAla | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |

TABLE A-continued

| Abbr. | Amino Acid |
|---|---|
| | Unusual Amino Acids |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

Amino acids can be in the L-form, D-form, or neither (e.g., glycine). As used herein, if the amino acid three-letter or one-letter designation does not indicate, the amino acid is in the L-form, unless otherwise indicated. When not in a sequence, the form of the amino acid when designated includes a hyphen (e.g., L-Lys). When in a sequence the hyphen is removed.

As used herein (unless otherwise specified), a "fragment" of a protein or amino acid sequence includes at least 3 consecutive amino acids. For example, a fragment can include 3, 4, 5, 6, 7, 8, 9, 10, 11, 12, 13, 14, 15, 16, 17, 18, 19, 20, 50, 100, 150, 200, 250, 500, 1000, 1500, 2000, no more than 50, no more than 100, no more than 500, no more than 1000, no more than 1500, no more than 2000, at least 50, at least 100, at least 500, at least 1000, at least 1500, or at least 2000 consecutive amino acids of the protein or amino acid sequence. The length of the fragment can be appropriately changed depending on a desired property or function.

As used herein (unless otherwise specified), a "mutant" (or similar language such as mutated or mutation) of a protein or amino acid sequence includes truncations, additions, deletions, substitutions, and other alterations of the protein or amino acid sequence provided some degree of a desired property or a desired function remains. In some embodiments, the mutations can be a combination of two or more truncations, deletions, additions, substitutions, or other alterations. In some embodiments, one or more substitutions can be conservative substitutions. In some embodiments, conservative substitutions can be based on hydropathic index of Kyte and Doolittle J. Mol. Biol. 1982, Vol. 157, pp. 105-132 (e.g., substitutions of within ±2, within ±1, or within ±0.5), on hydrophilic values of U.S. Pat. No. 4,554,101 (e.g., substitutions of within ±2, within ±1, or within ±0.5), or on the size of the amino acid (e.g., side group size). In certain embodiments, the following substitutions are considered conservative if one amino acid is substituted from another in the same group: Group 1 is Ile, Leu, Val, Ala, Gly; Group 2 is Trp, Tyr, Phe; Group 3 is Asp, Glu, Asn, Gln; Group 4 is Cys, Ser, Thr, Met; Group 5 is His, Lys, Arg. In some instances, a conservative substitution minimally disrupts (or can enhance) one or more desired properties or functions.

Some embodiments of the invention include compounds of Formula (I):

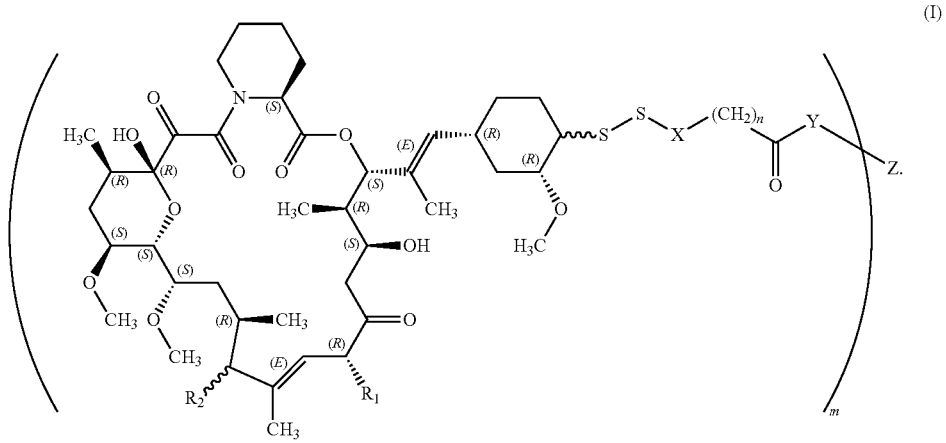

In some embodiments, the compounds of Formula (I) can be in the form of salts, optical and geometric isomers, and salts of isomers. In other embodiments, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. In some instances, for acidic compounds, salts can include metals, amines, or organic cations (e.g. quaternary ammonium). In yet other embodiments, simple derivatives of the compounds (e.g., ethers, esters, or amides) which have desirable retention and release characteristics but which are easily hydrolyzed by body pH, enzymes, or other suitable means, can be employed.

In certain embodiments, $R_1$ can be H, allyl, vinyl, hydroxyl, Cl, Br, F, I, thiol, amino, nitro, cyano, branched or unbranched $C_1$-$C_4$ (i.e., $C_1$, $C_2$, $C_3$, or $C_4$) alkyl, branched or unbranched $C_1$-$C_4$ (i.e., $C_1$, $C_2$, $C_3$, or $C_4$) alkylnoic, phenyl, $C_1$-$C_2$ perfluorinated alkyl, alkyl amino, oxo, carboxy, acetyl, amido, or $C_1$-$C_3$ (i.e., $C_1$, $C_2$, or $C_3$) akloxy. In some embodiments, $R_1$ is H, allyl, ethyl, methyl, or OH. In some embodiments, $R_1$ is allyl, ethyl, or methyl.

In certain embodiments, $R_2$ can be H, allyl, vinyl, hydroxyl, Cl, Br, F, I, thiol, amino, nitro, cyano, branched or unbranched $C_1$-$C_4$ (i.e., $C_1$, $C_2$, $C_3$, or $C_4$) alkyl, branched or unbranched $C_1$-$C_4$ (i.e., $C_1$, $C_2$, $C_3$, or $C_4$) alkylnoic, phenyl, $C_1$-$C_2$ perfluorinated alkyl, alkyl amino, oxo, carboxy, acetyl, amido, or $C_1$-$C_3$ (i.e., $C_1$, $C_2$, or $C_3$) akloxy. In some embodiments, $R_2$ is H, allyl, ethyl, methyl, or OH. In some embodiments, $R_1$ is H or OH. The stereocenter of the carbon connecting to $R_2$ can be R or S.

In some embodiments, $R_1$ can be the same or different than $R_2$. In other embodiments, $R_1$ is allyl and $R_2$ is H. In other embodiments, $R_1$ is ethyl and $R_2$ is H. In other embodiments, $R_1$ is methyl and $R_2$ is H. In other embodiments, $R_1$ is H and $R_2$ is H. In other embodiments, $R_1$ is allyl and $R_2$ is OH. In other embodiments, $R_1$ is ethyl and $R_2$ is OH. In other embodiments, $R_1$ is methyl and $R_2$ is OH. In other embodiments, $R_1$ is H and $R_2$ is OH. In other embodiments, $R_1$ is OH and $R_2$ is OH.

In some embodiments, X is a bivalent substituted or unsubstituted $C_4$-$C_{12}$ (i.e., $C_4$, $C_5$, $C_6$, $C_7$, $C_8$, $C_9$, $C_{10}$, $C_{11}$ or, $C_{12}$) conjugated cyclic hydrocarbon or a

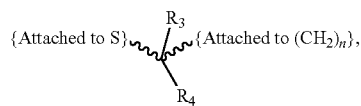

where $R_3$ and $R_4$ can be the same or different and can be a hydrogen or a substituted or unsubstituted, branched or unbranched $C_1$-$C_{11}$ (i.e., $C_1$, $C_2$, $C_3$, $C_4$, $C_5$, $C_6$, $C_7$, $C_8$, $C_9$, $C_{10}$, or $C_{11}$) alkyl. As used herein, "bivalent" means a radical with two hydrogens removed from one or two carbon atoms on the indicated compound; the places where the hydrogens are removed are attachment points to the adjacent parts of Formula (I). As used herein, "substituted" is defined by the substitution of one, two, or three hydrogens on a carbon by groups including, but not limited to, halogen (e.g., Cl, Br, or F), hydroxy, thiol, amino, nitro, cyano, branched or unbranched $C_1$-$C_4$ (i.e., $C_1$, $C_2$, $C_3$, or $C_4$) alkyl, branched or unbranched $C_1$-$C_4$ (i.e., $C_1$, $C_2$, $C_3$, or $C_4$) alkylnoic, $C_1$-$C_2$ perfluorinated alkyl, alkylamino, oxo, carboxy, acetyl, amido, vinyl, and $C_1$-$C_3$ (i.e., $C_1$, $C_2$, or $C_3$) alkoxy. If X is a bivalent substituted or unsubstituted $C_4$-$C_{12}$ conjugated cyclic hydrocarbon, X, in some embodiments, can be attached to the adjacent S and the adjacent $(CH_2)_n$ using any carbon on the conjugated cyclic hydrocarbon or, if substituted, using any carbon on any moiety that is substituting; X can be attached to the adjacent S and the adjacent $(CH_2)_n$ using the same carbon or using different carbons. In certain embodiments, X can influence the specificity of disulfide cleavage of Formula (I), by, for example, modulating (e.g., increasing or decreasing) the cleavage rate of the disulfide bond adjacent to X, modulating (e.g., increasing or decreasing) the cleavage rate cleavage of a disulfide bond adjacent to Z, or modulating (e.g., increasing or decreasing) the cleavage rate cleavage of the disulfide bond adjacent to X as relative to the cleavage rate cleavage of a disulfide bond adjacent to Z (e.g., by comparing absolute rates, relative rates, or percent change in rates). In some embodiments, X is a bivalent annulene (e.g., bivalent cyclobutadiene, bivalent benzene, bivalent cyclooctatetraene, bivalent cyclodecapentaene, or bivalent cyclododecahexaene). In some embodiments, X is an bivalent aromatic moiety (e.g., bivalent monocyclic moiety or bivalent polycyclic moiety, such as bivalent bicyclic moiety), such as but not limited to bivalent benzene, bivalent biphenyl, or bivalent napthalene. In still other embodiments, X is a bivalent benzene or is an unsubstituted $C_1$ (i.e., $R_3$ and $R_4$ are both hydrogen). In still other embodiments, X is an unsubstituted $C_1$ (i.e., $R_3$ and $R_4$ are both hydrogen) or is a substituted $C_1$, where (a) $R_3$ is H and $R_4$ is methyl, (b) $R_3$ is H and $R_4$ is ethyl, (c) $R_3$ is H and $R_4$ is propyl, (d) $R_3$ is methyl and $R_4$ is H, (e) $R_3$ is methyl and $R_4$ is methyl, (f) $R_3$ is methyl and $R_4$ is ethyl, (g) $R_3$ is methyl and $R_4$ is propyl, (h) $R_3$ is ethyl and $R_4$ is H, (i) $R_3$ is ethyl and $R_4$ is methyl, (j) $R_3$ is ethyl and $R_4$ is ethyl, (k) $R_3$ is ethyl and $R_4$ is propyl, (l) $R_3$ is propyl and $R_4$ is H, (m) $R_3$ is propyl and $R_4$ is methyl, (n) $R_3$ is propyl and $R_4$ is ethyl, or (o) $R_3$ is propyl and $R_4$ is propyl.

In some embodiments, n can be 0, 1, 2, 3, 4, or 5. In certain embodiments, n is 0 or n is 1.

In some embodiments, m can be 1, 2, 3, 4, 5, 6, 7, 8, 9, or 10. In certain embodiments, m is 1 or m is 2. In some embodiments, a solution comprising Formula (I) can have a mixture of formulas that have different values of m, resulting in a solution which can yield an average m value. In some examples, the solution averaged m-value can be, but is not limited to any rational number from 1 to 10, such as about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.5, about 4, about 4.5, about 5, about 5.5, about 6, about 6.5, about 7, about 7.5, about 8, about 8.5, about 9, about 9.5, or about 10.

In other embodiments, Y is an amino acid sequence comprising no more than about 30 amino acids. In certain embodiments, Y is attached to the adjacent carboxy of Formula (I) by a Y amino acid backbone atom (e.g., by a carbon, by an oxygen, by an N-terminus nitrogen, or by another nitrogen if a modified amino acid is used) or by a Y amino acid side chain atom (e.g., by a carbon, by an oxygen, or by a nitrogen on a side chain). In some embodiments, the amino acids of Y are D-amino acids, L-amino acids, or both. In other embodiments, the number of amino acids in the Y amino acid sequence can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, from about 2 to about 30, from about 4 to about 20, from about 5 to about 17, or from about 7 to about 15. In certain embodiments, the percentage of D-amino acids in the Y amino acid sequence can be at least about 25%, at least about 50%, at least about 75%, no more than about 25%, no more than about 50%, or no more than about 75%. In certain instances, the percentage of the Y amino acid sequence that are D-amino acids can be about 10%, about 20%, about 25%, about 30%, about 40%, about 50%, about 60%, about 70%, about 75%, about 80%, or about 90%. In certain embodiments, the percentage of L-amino acids in the Y amino acid sequence can be at least about 25%, at least about 50%, at least about 75%, no more than about 25%, no more than about 50%, or no more than about 75%. In certain instances, the percentage of the Y amino acid sequence that are L-amino acids can be about 10%, about 20%, about 25%, about 30%, about 40%, about 50%, about 60%, about 70%, about 75%, about 80%, or about 90%. In other embodiments, a portion of the Y amino acid sequence can have 2, 3, 4, or 5 successive L-amino acids. In some embodiments, the successive L-amino acids in the Y amino acid sequence can be the same or different. In other embodiments, a portion of the Y amino acid sequence can have 2, 3, 4, or 5 successive D-amino acids. In some embodiments, the successive D-amino acids in the Y amino acid sequence can be the same or different. In some embodiments, the same amino acid is alternated in its D- and L-form (e.g., DSer-Ser-DSer-Ser-DSer). In other embodiments, the Y amino acid sequence does not self assemble or have secondary structure.

In some embodiments, the amino acids in the amino acid sequence of Y can be Gly, L-Ala, L-Cys, L-Asp, L-Glu, L-Phe, L-His, L-Ile, L-Lys, L-Leu, L-Met, L-Asn, L-Pro, L-Gln, L-Arg, L-Ser, L-Thr, L-Val, L-Trp, L-Tyr, D-Ala, D-Cys, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, or D-Tyr. In some embodiments, the amino acids in the amino acid sequence of Y can be L-Cys, L-Asp, L-Glu, L-His, L-Lys, L-Asn, L-Gln, L-Arg, L-Ser, L-Thr, L-Tyr, D-Cys, D-Asp, D-Glu, D-His, D-Lys, D-Asn, D-Gln, D-Arg, D-Ser, D-Thr, or D-Tyr. In some embodiments, the amino acids in the amino acid sequence of Y can be L-Asp, L-Glu, L-His, L-Lys, L-Asn, L-Gln, L-Arg, L-Ser, L-Thr, L-Tyr, D-Asp, D-Glu, D-His, D-Lys, D-Asn, D-Gln, D-Arg, D-Ser, D-Thr, or D-Tyr. In some embodiments, the amino acids in the amino acid sequence of Y can be L-Asp, L-Glu, L-His, L-Lys, L-Arg, D-Asp, D-Glu, D-His, D-Lys, or D-Arg. In some embodiments, the amino acids in the amino acid sequence of Y can be L-Asp, L-Glu, L-Asn, L-Gln, L-Ser, L-Thr, D-Asp, D-Glu, D-Asn, D-Gln, D-Ser, or D-Thr. In other embodiments unusual amino acids (in their L- or D-form or any of their stereoisomers, as dictated by their structures) can be in the amino acid sequences.

In some embodiments, some of the amino acids in the Y amino acid sequence can be hydrophilic amino acids. Hydrophilic amino acids include but are not limited to L-Cys, L-Asp, L-Glu, L-His, L-Lys, L-Asn, L-Gln, L-Arg, L-Ser, L-Thr, L-Tyr, D-Cys, D-Asp, D-Glu, D-His, D-Lys, D-Asn, D-Gln, D-Arg, D-Ser, D-Thr, D-Tyr, Dbu, Des, Dpm, Dpr, or Ide. In certain embodiments, the percentage of hydrophilic amino acids in the Y amino acid sequence can be at least about 25%, at least about 50%, at least about 75%, no more than about 25%, no more than about 50%, or no more than about 75%. In certain instances, the percentage of the Y amino acid sequence that are hydrophilic amino acids can be about 10%, about 20%, about 25%, about 30%, about 40%, about 50%, about 60%, about 70%, about 75%, about 80%, or about 90%.

In certain embodiments, the Y amino acid sequence increases the solubility (e.g., in water) of Formula (I). In some embodiments, the Y amino acid sequence acts as a stereochemical spacer. In some embodiments, the Y amino acid sequence increases the efficiency of protein conjugation (e.g., by acting as a stereochemical spacer). In other embodiments, —$NH_2$ can be on the C-terminus of the Y amino acid sequence. In some embodiments, the Y amino acid sequence is DSer-Ser-DSer-Ser-DSer-Nle-DTyr-DSer-Cys-Phe-DTrp-Lys-Thr-Cys-Thr; DSer-Ser-Thr-Ser-DSer-Lys-DSer; DSer-Ser-Thr-Ser-DSer-Lys-DSer-Asp-DAsp-Asp-DAsp; or DAsp-Asp-DAsp-Asp-DSer-Ser-Thr-Ser-DSer-Lys-DSer. In other embodiments, the Y amino acid sequence is DSer-Ser-DSer-Ser-DSer-Nle-DTyr-DSer-Cys-Phe-DTrp-Lys-Thr-Cys-Thr-$NH_2$; DSer-Ser-Thr-Ser-DSer-Lys-DSer-$NH_2$; DSer-Ser-Thr-Ser-DSer-Lys-DSer-Asp-DAsp-Asp-DAsp-$NH_2$; or DAsp-Asp-DAsp-Asp-DSer-Ser-Thr-Ser-DSer-Lys-DSer-$NH_2$.

In some embodiments, Y can be
(a) DAsp-Asp-DAsp-Asp-DSer-Ser-Thr-Ser-DSer-Lys-DSer-NH$_2$, where Y can be attached to Z via reaction with the side group amine on the Lysine;
(b) DAsp-Asp-DAsp-Asp-DSer-Ser-Thr-Ser-DSer-Lys-DSer, where Y can be attached to Z via reaction with the side group or backbone of the C-terminal amino acid (here DSer);

(c)

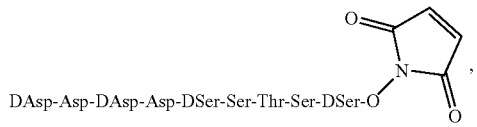

where Y can be attached to Z via reaction with the maleimide;

(d)

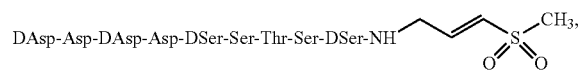

where Y can be attached to Z via reaction with the vinyl sulfone;

(e)

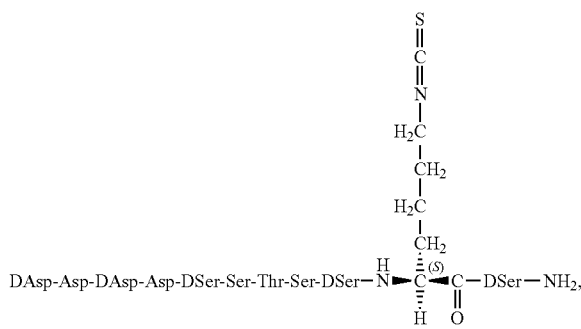

where Y can be attached to Z via reaction with the isothiocyanate;

(f)

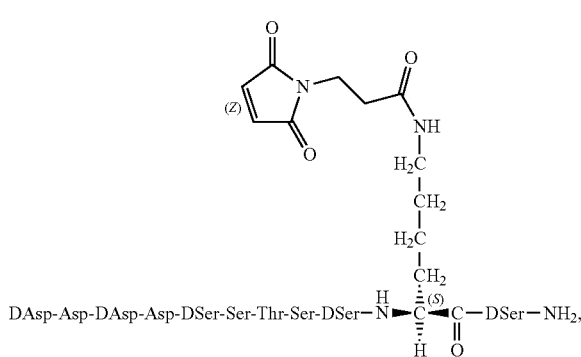

where Y can be attached to Z via reaction with the maleimide; or (g)

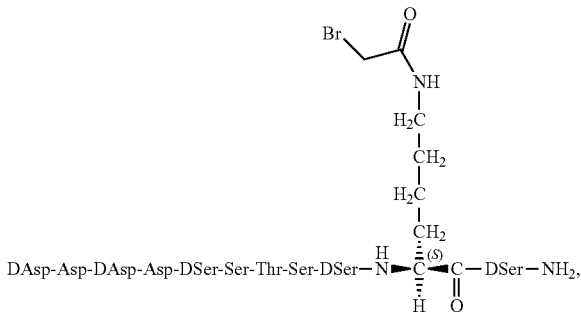

where Y can be attached to Z via reaction with the bromoacetamide. In other embodiments, the DAsp-Asp-DAsp-Asp-DSer-Ser-Thr-Ser-DSer- portion of (a)-(g) above, can be replaced by DSer-Ser-Thr-Ser-DSer-.

In some embodiments, Z is an amino acid sequence comprising no more than about 2500 amino acids, having a molecular mass of no more than about 300,000, or both. In certain embodiments, Z comprises no more than about 2000 amino acids, no more than about 1500 amino acids, no more than about 1000 amino acids, no more than about 500 amino acids, or no more than about 250 amino acids. In other embodiments, Z has a molecular mass no more than about 250,000, no more than about 200,000, no more than about 150,000, no more than about 100,000, or no more than about 50,000. Molecular mass can be determined using any suitable method including, for example, using sodium dodecyl sulfate polyacrylamide gel electrophoresis (SDS-PAGE), analytical ultracentrifugation, light scattering, or mass spectrometry (e.g., electrospray/ionization (ESI) and matrix-assisted laser desorption/ionization (MALDI)). Unless otherwise specified, molecular mass is determined using MALDI.

In certain embodiments, unusual amino acids (in their L- or D-form or any of their stereoisomers, as dictated by their structures) can be in the Z amino acid sequence.

In certain embodiments, Z is attached to Y using any suitable conjugation including but not limited to (a) a disulfide bond, (b) a thiol from Z attached to an unusual amino acid of Y, a modified side group of an amino acid of Y (e.g., serine, threonine, asparagine, glutamine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), a modified backbone of an amino acid of Y (e.g., serine, threonine, asparagine, glutamine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), or a combination thereof of Y, (c) a thiol from Y attached to an unusual amino acid of Z, a modified side group of an amino acid of Z (e.g., serine, threonine, asparagine, glutamine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), a modified backbone of an amino acid of Z (e.g., serine, threonine, asparagine, glutamine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), or a combination thereof of Z, (d) an unusual amino acid of Z, a modified side group of an amino acid of Z (e.g., serine, threonine, asparagine, glutamine, tyrosine, cysteine, lysine, ornithine, 2,4- diaminobutyric acid, 2,3-diaminopropionic acid, 2,2'-diaminopimelic acid, arginine, histidine, aspartic acid, or glutamic acid), a modified backbone of an amino acid of Z (e.g., serine, threonine, asparagine, glutamine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), or a combination thereof of Z attached to an unusual amino acid of Y, a modified side group of an amino acid of Y (e.g., serine, threonine, asparagine, glutamine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), a modified backbone of an amino acid of Y (e.g., serine, threonine, asparagine, glutamine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), or a combination thereof of Y. In certain embodiments, the amino acid that has modified side group is an amino acid that has an amino side group (e.g., lysine, ornithine, 2,4-diaminobutyric acid, 2,3-diaminopropionic acid, 2,2'-diaminopimelic acid, arginine, or histidine). In certain embodiments, the amino acid that has modified side group is lysine, ornithine, 2,4-diaminobutyric acid, 2,3-diaminopropionic acid, 2,2'-diaminopimelic acid, arginine, or histidine. In certain embodiments, the modified side group of an amino acid comprises a maleimide (e.g., lysine, ornithine, 2,4-diaminobutyric acid, 2,3-diaminopropionic acid, 2,2'-diaminopimelic acid, arginine, or histidine), acetate (via, for example, a bromoacetate addition to a hydroxy of an amino acid (e.g., serine, threonine, or tyrosine)), or carboxyl (e.g., aspartic acid or glutamic acid). Some examples of conjugation include but are not limited to a disulfide bond, a thiol of Z attached to a maleimide modified amino side group of an amino acid of Y, a thiol of Y attached to a maleimide modified amino side group of an amino acid of Z, a thiol of Z attached to a maleimide modified lysine of Y, a thiol of Y attached to a maleimide modified lysine of Z, a thiol of Z attached to a maleimide modified ornithine of Y, a thiol of Y attached to a maleimide modified ornithine of Z, a thiol of Z attached to a maleimide modified 2,4-diaminobutyric acid of Y, a thiol of Y attached to a maleimide modified 2,4-diaminobutyric acid of Z, a thiol of Z attached to a maleimide modified 2,3-diaminopropionic acid of Y, or a thiol of Y attached to a maleimide modified 2,3-diaminopropionic acid of Z. Some examples of conjugation include but are not limited to a disulfide bond, a thiol of Z attached to a maleimide modified lysine of Y, a thiol of Y attached to a maleimide modified lysine of Z, a thiol of Z attached to a maleimide modified ornithine of Y, a thiol of Y attached to a maleimide modified ornithine of Z, a thiol of Z attached to a maleimide modified 2,4-diaminobutyric acid of Y, a thiol of Y attached to a maleimide modified 2,4-diaminobutyric acid of Z, a thiol of Z attached to a maleimide modified 2,3-diaminopropionic acid of Y, or a thiol of Y attached to a maleimide modified 2,3-diaminopropionic acid of Z. Some examples of conjugation include but are not limited to a disulfide bond, a thiol of Z attached to a maleimide modified lysine of Y, or a thiol of Y attached to a maleimide modified lysine of Z.

In other embodiments, Z is attached to Y using any suitable conjugation including but not limited to, (a) where Y comprises a suitable amine-reactive group (e.g., isothiocyanates, isocyanates, acyl azides, N-hydroxysuccinimide esters, sulfonyl chlorides, vinyl sulfones, aldehydes, ketones, glyoxals, epoxides, oxiranes, carbonates, arylating agents (e.g., aryl halides), imidoesters, imidates, carbodiimides, anhydrides, haloacetyls (e.g., bromoacetamide), or maleimides) prior to being attached to Z via reaction with an amine on Z, (b) where Y comprises a suitable thiol-reactive group (e.g., haloacetyls (e.g., bromoacetamide), benzyl halides, alkyl halides, maleimides, aziridines, acryloyls, arylating agents, or thiol-disulfide exchange functional groups (e.g., pyridyl disulfides or 5-thio-2-nitrobenzoic acid)) prior to being attached to Z via reaction with a sulfhydryl on Z, (c) where Y comprises a suitable carboxylate-reactive group (e.g., diazoalkyls, diazoacetyls, diazoacetates, carbonyldiimidazoles (such as N,N'-carbonyl diimidazole via an N-acylimidazole), or carbodiimides) prior to being attached to Z via reaction with a carboxylate on Z, (d) where Y comprises a suitable hydroxyl-reactive group (e.g., epoxides, oxiranes, carbonyldiimidazoles, N,N'-disuccinimidyl carbonates, N-hydroxysuccinimidyl chloroformates, groups from peroxidate oxidation, groups from enzymatic oxidation, alkyl halogens, or isocyanates) prior to being attached to Z via reaction with a hydroxyl on Z, (e) where Y comprises a suitable aldehyde- or ketone-reactive group (e.g., hydrazine derivatives, Schiff base formation via amine, reductive amination via Schiff base, or Mannich condensation via amine) prior to being attached to Z via reaction with a aldehyde or a ketone on Z, or (f) where Y comprises a suitable hydrogen-reactive group (e.g., diazoniums or Mannich condensation via amine) prior to being attached to Z via reaction with a reactive hydrogen on Z.

In other embodiments, Y is attached to Z using any suitable conjugation including but not limited to, (a) where Z comprises a suitable amine-reactive group (e.g., isothiocyanates, isocyanates, acyl azides, N-hydroxysuccinimide esters, sulfonyl chlorides, vinyl sulfones, aldehydes, ketones, glyoxals, epoxides, oxiranes, carbonates, arylating agents (e.g., aryl halides), imidoesters, imidates, carbodiimides, anhydrides, haloacetyls (e.g., bromoacetamide), or maleimides) prior to being attached to Y via reaction with an amine on Y, (b) where Z comprises a suitable thiol-reactive group (e.g., haloacetyls (e.g., bromoacetamide), benzyl halides, alkyl halides, maleimides, aziridines, acryloyls, arylating agents, or thiol-disulfide exchange functional groups (e.g., pyridyl disulfides or 5-thio-2-nitrobenzoic acid)) prior to being attached to Y via reaction with a sulfhydryl on Y, (c) where Z comprises a suitable carboxylate-reactive group (e.g., diazoalkyls, diazoacetyls, diazoacetates, carbonyldiimidazoles (e.g., N,N'-carbonyl diimidazole via an N-acylimidazole), or carbodiimides) prior to being attached to Y via reaction with a carboxylate on Y, (d) where Z comprises a suitable hydroxyl-reactive group (e.g., epoxides, oxiranes, carbonyldiimidazoles, N,N'-disuccinimidyl carbonates, N-hydroxysuccinimidyl chloroformates, groups from peroxidate oxidation, groups from enzymatic oxidation, alkyl halogens, or isocyanates) prior to being attached to Y via reaction with a hydroxyl on Y, (e) where Z comprises a suitable aldehyde- or ketone-reactive group (e.g., hydrazine derivatives, Schiff base formation via amine, reductive amination via Schiff base, or Mannich condensation via amine) prior to being attached to Y via reaction with a aldehyde or a ketone on Y, or (f) where Z comprises a suitable hydrogen-reactive group (e.g., diazoniums or Mannich condensation via amine) prior to being attached to Y via reaction with a reactive hydrogen on Y.

In some embodiments, changing the pH of the conjugation reaction solution can alter the conjugation preference of the conjugation reaction. For example, haloacetyls (e.g., bromoacetamide) and/or maleimides can have a preference for reacting with thiols under certain pH conditions (e.g., a pH lower than that used to react with an amine, a pH of no more than about 7, or a pH of no more than about 6). In other examples, haloacetyls (e.g., bromoacetamide) and/or maleimides can have a preference for reacting with amines under certain pH conditions (e.g., a pH higher than that used to react with a thiol, a pH of at least about 7, or a pH of at least about 8).

In other embodiments, any suitable photoreactive chemical reaction can be used to attach Y to Z or Z to Y, including but not limited to processes that comprise chemical reactions that use UV light with certain chemicals including but not limited to, aryl azides, halogenated aryl azides, benzophenones, diazo compounds, or diazirines.

In other embodiments, Y is attached to Z using any suitable conjugation including but not limited to, where Y comprises a suitable group that is activated to react with a moiety (e.g., activated to react with carboxylate) prior to being attached to Z via reaction with that Z moiety (e.g., carboxylate). In certain embodiments, Y comprises an activated group (e.g., activated to react with carboxylate) prior to being attached to Z which includes but is not limited to an N-hydroxysuccinimide ester, an isocyanate, an isothiocyanate, a vinyl sulfone, an amine, a diazoalkyl, a diazoacetyl, a diazoacetate, a carbonyldiimidazole (e.g., N,N'-carbonyl diimidazole or N-acylimidazole), or a carbodiimide. When Y comprises an activated group (e.g., activated to react with carboxylate), the amino acid comprising the activated group can be a naturally occurring amino acid (e.g., lysine, arginine, histidine, tryptophan, glutamine, or asparagine), an unusual amino acid (e.g., ornithine, 2,4-diaminobutyric acid, 2,3-diaminopropionic acid, or 2,2'-diaminopimelic acid), a modified naturally occurring amino acid, or a modified unusual amino acid. The modification of the modified naturally occurring amino acid or of the modified unusual amino acid, can occur in the backbone, in the side group, or both. Y can comprise one or more activated groups (e.g., activated to react with carboxylates); none or one of the activated groups (e.g., activated to react with carboxylates) can be used to (but are not required to) attach Y to Z.

In other embodiments, Z is attached to Y using any suitable conjugation including but not limited to, where Z comprises a suitable group that is activated to react with a moiety (e.g., activated to react with carboxylate) prior to being attached to Y via reaction with that Y moiety (e.g., carboxylate). In certain embodiments, Z comprises an activated group (e.g., activated to react with carboxylate) prior to being attached to Y which includes but is not limited to an N-hydroxysuccinimide ester, an isocyanate, an isothiocyanate, a vinyl sulfone, an amine, a diazoalkyl, a diazoacetyl, a diazoacetate, a carbonyldiimidazole (e.g., N,N'-carbonyl diimidazole or N-acylimidazole), or a carbodiimide. When Y comprises an activated group (e.g., activated to react with carboxylate), the amino acid comprising the activated group can be a naturally occurring amino acid (e.g., lysine, arginine, histidine, tryptophan, glutamine, or asparagine), an unusual amino acid (e.g., ornithine, 2,4-diaminobutyric acid, 2,3-diaminopropionic acid, or 2,2'-diaminopimelic acid), a modified naturally occurring amino acid, or a modified unusual amino acid. The modification of the modified naturally occurring amino acid or of the modified unusual amino acid, can occur in the backbone, in the side group, or both. Z can comprise one or more activated groups (e.g., activated to react with carboxylates); none, one or more of the activated groups (e.g., activated to react with carboxylates) can be used to (but are not required to) attach Z to Y.

Nonlimiting examples of suitable attachments of Y to Z or Z to Y can be found, for example, in "Bioconjugate Techniques, Third Edition" by Greg T. Hermanson, Academic Press, 2013 (e.g., see Chapters 2 and 3) or "Bioconjugate Techniques" by Greg T. Hermanson, Academic Press, 1996 (e.g., see Chapter 2).

In some embodiments, Z can be attached to any suitable amino acid on Y, including but not limited to, the N-terminal amino acid of Y, the C-terminal amino acid of Y, the amino acid that is adjacent to the N-terminal amino acid of Y, the amino acid that is adjacent to the C-terminal amino acid of Y, the amino acid that is next to the amino acid adjacent to the N-terminal amino acid of Y, or the amino acid that is next to the amino acid adjacent to the C-terminal amino acid of Y.

In some embodiments, the Z amino acid sequence comprises a targeting amino acid sequence. Unless otherwise indicated, the term "to target" or "targeting" (or variations thereof) means that Z when not bonded to Formula (I) has affinity for, is directed to (directly or indirectly), or ends up at the target (e.g., a cell, tissue or organ); similarly when Formula (I) comprises Z "to target" or "targeting" (or variations thereof) means that Formula (I) has affinity for, is directed to (directly or indirectly), or ends up at the target (e.g., a cell, tissue or organ). The targeting amino acid sequence can be a protein, a mutated protein, a fragment of the protein or a fragment of the mutated protein.

The length of the fragment can be appropriately changed depending on one or more desired properties or functions (e.g., targeting a desired target). A mutant provides some degree of one or more desired properties or functions (e.g., in the targeting amino acid sequence a desired function can be but is not limited to targeting to the desired target). In some instances, a conservative substitution minimally disrupts (or can enhance) one or more desired properties or functions (e.g., targeting to the desired target).

In some embodiments, the targeting amino acid sequence can target, but is not limited to cells related to inflammation (e.g., cells in tissues or organs in an animal body), organs (e.g., kidney, heart, liver, small bowel, pancreas, lung, trachea, skin, cornea, bone marrow, or limb), or combinations thereof. In other embodiments, the target of the targeting amino acid sequence can be, but is not limited to T cells (e.g., cytotoxic or helper T cells), activated T-cells, differentiated T-cells, effector cells, transplanted organs (e.g., an allograft organ transplant, a xenograft organ transplant, a cloned organ transplant, or a 3D printed organ transplant), organs undergoing hyperacute rejection, organs undergoing acute rejection, organs undergoing chronic rejection, organs, tissues or cells associated with autoimmune diseases, organs, tissues or cells associated with inflammation, organs or tissues that are inflamed (e.g., due to an autoimmune disease, organ transplant, injury, or infection), or combinations thereof. Organs or tissues that are inflamed can include but are not limited to kidney, heart, liver, small bowel, pancreas, lung, trachea, skin, cornea, bone marrow, limb, joint (e.g., knee, hip, shoulder, wrist, or ankle), cartilage, synovial fibroblast, synovial membrane, or tissue or organ affected by autoimmune diseases. Autoimmune diseases that can result in targets for the targeting amino acid sequence can include but are not limited to Myocarditis, Postmyocardial infarction syndrome, Postpericardiotomy syndrome, Subacute bacterial endocarditis, Kidney, Anti-Glomerular Basement Membrane nephritis, Interstitial cystitis, Lupus nephritis, Autoimmune hepatitis, Primary biliary cirrhosis, Primary sclerosing cholangitis, Antisynthetase syndrome, Skin, Alopecia Areata, Autoimmune Angioedema, Autoimmune progesterone dermatitis, autoimmune urticaria, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease, Morphea, Pemphigus vulgaris, Pityriasis lichenoides et varioliformis acuta, Mucha-Habermann disease, Psoriasis, Systemic scleroderma, Vitiligo, Addison's disease, Autoimmune polyendocrine syndrome, Autoimmune polyendocrine syndrome type 3, Autoimmune pancreatitis, Diabetes mellitus type 1, Autoimmune thyroiditis, Ord's thyroiditis, Graves' disease, Autoimmune oophoritis, Endometriosis, Autoimmune orchitis, Sjogren's sysndrome, Autoimmune enteropathy, inflammatory bowel disease, Celiac disease, Crohn's disease, Microscopic colitis, Ulcerative colitis, Antiphospholipid syndrome, Aplastic anemia, Autoimmune hemolytic anemia, Autoimmune lymphoproliferative syndrome, Autoimmune neutropenia, Autoimmune thrombocytopenic purpura, Cold agglutinin disease, Essential mixed cryoglobulinemia, Evans syndrome, IgG4-related systemic disease, Paroxysmal nocturnal hemoglobinuria, Paroxysmal nocturnal hemoglobinuria, Pernicious anemia, Pure red cell aplasia, Thrombocytopenia, Adiposis dolorosa, Adult-onset Still's disease, Ankylosing Spondylitis, CREST syndrome, Drug-induced lupus, Enthesitis-related arthritis, osteoarthritis, Eosinophilic fasciitis, Felty syndrome, Juvenile arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Sarcoidosis, Schnitzler syndrome, Systemic Lupus Erythematosus, Undifferentiated connective tissue disease, Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis, Acute motor axonal neuropathy, Anti-N-Methyl-D-Aspartate Receptor Encephalitis, Balo concentric sclerosis, Bickerstaff's encephalitis, Chronic inflammatory demyelinating polyneuropathy, Guillain-Barré syndrome, Hashimoto's encephalopathy, Idiopathic inflammatory demyelinating diseases, Lamber-Eaton myasthenic syndrome, Multiple sclerosis, Pediatric Autoimmune Neuropsychiatric Disorder Associated with *Streptococcus*, Progressive inflammatory neuropathy, Restless leg syndrome, Stiff person syndrome, Sydenham chorea, Transverse myelitis, Autoimmune retinopathy, Autoimmune uveitis, Cogan syndrome, Graves ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, Tolosa-Hunt syndrome, Autoimmune inner ear disease, Ménière's disease, Anti-neutrophil cytoplasmic antibody-associated vasculitis, Behçet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, Polyarteritis nodosa, Polymyalgia rheumatica, Urticarial vasculitis, Vasculitis, Chronic fatigue syndrome, Complex regional pain syndrome, Eosinophilic esophagitis, Gastritis, POEMS syndrome, Raynaud phenomenon, Primary immunodeficiency, or Pyoderma gangrenosum. In other embodiments, autoimmune diseases that can result in targets of the targeting amino acid sequence can be arthritis, osteoarthritis, rheumatoid arthritis, or ulcerative colitis.

In certain embodiments, the targeting amino acid sequence can be somatostatin, a somatostatin analog, bombesin, a bombesin analog (e.g., neuromedin B, gastrin releasing peptide), an antibody (e.g., humanized or partially humanized from a non-human animal such as but not limited to canine, mouse, or rat), a polyclonal antibody (e.g., humanized or partially humanized from a non-human animal such as but not limited to canine, mouse or rat), a monoclonal antibody (e.g., humanized or partially humanized from a non-human animal such as but not limited to canine, mouse or rat), a polyclonal antibody that targets T-cells (e.g., humanized or partially humanized from a non-human animal such as but not limited to canine, mouse or rat), a monoclonal antibody that targets T-cells (e.g., humanized or partially humanized from a non-human animal such as but not limited to canine, mouse or rat), a polyclonal antibody that targets Vascular adhesion protein 1 (e.g., humanized or partially humanized from a non-human animal such as but not limited to canine, mouse or rat), a monoclonal antibody that targets Vascular adhesion protein 1 (e.g., humanized or partially humanized from a non-human animal such as but not limited to canine, mouse or rat), a peptide that targets inflamed endothelial cells (e.g., GGGGKGGGG (SEQ ID NO: 1) or CARLSLSWRGLTLCPSK (SEQ ID NO: 2)), a peptide that targets integrin $\alpha_v\beta_3$ (e.g., RGD-based peptides such as but not limited to RGD, $RGD_2$, $RGD_3$, $RGD_4$, $RGD_5$), murine-based antibodies (e.g., used at doses in humans that minimize induction of human antimurine antibodies), besilesomab, fanolesomab, sulesomab, antimicrobial peptides (e.g., human lactoferrin, ubiquicidin, the ubiquicidin 29-41 peptide fragment, human neutrophil peptide 1-3), annexin-V, IL-2, IL-12, monoclonal antibodies to TNFα (e.g., infliximab, adalimumab), monoclonal antibodies to CD4 (e.g., the EP 1645 fragment (Biotectid GmbH, Germany)), monoclonal antibodies to CD20 (e.g., rituximab), monoclonal antibodies to CD3 (e.g., muromonab, visilizumab), KJ1-26 monoclonal antibodies (e.g., cOVA-TCR-specific monoclonal antibodies and $F(ab')_2$ fragments thereof), transferrin, an albumin, human serum albumin (HSA), Domain I of HSA, Domain II of HSA, Domain III of HSA, bovine serum albumin (BSA), an engineered albumin (e.g., Veltis® from Novozymes), mutants thereof or fragments (e.g., $F(ab')_2$ fragments of antibodies) thereof (including fragments of mutants). In certain embodiments, the targeting amino acid sequence can be recombinantly made (e.g., in CHO cells) or can be purified from a natural source. In yet other embodiments, the targeting amino acid sequence can be BSA, HSA, or transferrin.

In some embodiments, the targeting amino acid sequence can be a somatostatin or a somatostatin analog. Somatostatin is Ala-Gly-Cys-Lys-Asn-Phe-Phe-Trp-Lys-Thr-Phe-Thr-Ser-Cys-$NH_2$ (SEQ ID NO: 3). In certain embodiments, a somatostatin analog can be a polypeptide that is similar in sequence to somatostatin, but still maintain one or more desired properties or functions (e.g., targeting or stability in circulation). In some instances, the somatostatin analog comprises one or more mutations of somatostatin. In some instances, the somatostatin analog comprises one or more conservative substitutions from somatostatin. In other instances, the somatostatin analog comprises at least 4, 5, 6, 7, 8, 9, 10, 11, 12, 13, or 14 amino acids that are the same (e.g., in the same relative position) as somatostatin. In some instances, the somatostatin analog comprises 5, 6, 7, 8, 9, 10, 11, 12, 13, 14, 15, 16, 17, 18, 19, 20, 21, 22, 23, 24, 25, 26, 27, 28, 29, or 30 amino acids. In certain embodiments, the somatostatin analog can be cyclic or comprises at least one cyclic structure; cyclization can occur, for example, by forming a disulfide bold between two cysteines. In some embodiments, the somatostatin analog can be octreotide, octreotate, lanreotide, or pasireotide.

In some embodiments, the targeting amino acid sequence can be a bombesin or a bombesin analog. Bombesin is Pyr-Gln-Arg-Leu-Gly-Asn-Gln-Trp-Ala-Val-Gly-His-Leu-Met-NH$_2$ (SEQ ID NO: 4). In certain embodiments, a bombesin analog can be a polypeptide that is similar in sequence to bombesin, but still maintain one or more desired properties or functions (e.g., targeting or stability in circulation). In some instances, the bombesin analog comprises one or more mutations of bombesin. In some instances, the bombesin analog comprises one or more conservative substitutions of bombesin. In other instances, the bombesin analog comprises at least 4, 5, 6, 7, 8, 9, 10, 11, 12, 13, or 14 amino acids that are the same (e.g., in the same relative position) as bombesin. In some instances, the bombesin analog comprises 5, 6, 7, 8, 9, 10, 11, 12, 13, 14, 15, 16, 17, 18, 19, 20, 21, 22, 23, 24, 25, 26, 27, 28, 29, or 30 amino acids. In certain embodiments, the bombesin analog can be cyclic or comprises at least one cyclic structure; cyclization can occur, for example, by forming a disulfide bold between two cysteines. In some embodiments, the bombesin analog can be a neuromedin B (e.g., TPFSWDL-PEPRSRASKIRVHPRGNLWATGHFM-NH$_2$, SEQ ID NO: 5), a neuromedin B 23-32 (e.g., GNLWATGHFM-NH$_2$, SEQ ID NO: 6), a gastrin-releasing peptide (e.g., VPL-PAGGGTVLTKMYPRGNHWAVGHLM-NH$_2$, SEQ ID NO: 7 or neuromedin C GSHWAVGHLM-NH$_2$, SEQ ID NO: 8), or GNHWAVGHLM-NH$_2$, SEQ ID NO: 9.

In other embodiments, the Z amino acid sequence comprises a stabilizing amino acid sequence that stabilizes the compound. In certain embodiments, the targeting amino acid sequence overlaps with the stabilizing amino acid sequence, encompasses the stabilizing amino acid sequence, is the same as the stabilizing amino acid sequence, or does not overlap with the stabilizing amino acid sequence. In some embodiments, the targeting amino acid sequence is fused with the stabilizing amino acid sequence or is conjugated to the stabilizing amino acid sequence. Stabilizing the compound can include, for example, maintaining or modulating (e.g., increasing or decreasing) any suitable desired property or function of the compound, including but not limited to water solubility (e.g., increasing), half-life in the blood (e.g., increasing), half-life in the body prior to reaching a target (e.g., increasing), stability in circulation prior to reaching a target (e.g., increasing), prevention of or decreased absorption by the kidney, or prevention of or decreased absorption by the brain.

The stabilizing amino acid sequence can, in certain embodiments, be a protein, a mutated protein, a fragment of a protein, or a fragment of a mutated protein. The length of the fragment can be appropriately changed depending on one or more desired properties or functions (e.g., stabilizing the compound). In some instances, mutations can comprise suitable modifications to the stabilizing amino acid sequence while retaining some degree (or enhancing) of one or more desired properties or functions, such as stabilizing the compound. In some instances, a conservative substitution minimally disrupts (or can enhance) one or more desired properties or functions (e.g., stabilizing the compound).

In some embodiments, the stabilizing amino acid sequence can be, but is not limited to, an albumin, human serum albumin (HSA), Domain I of HSA, Domain II of HSA, Domain III of HSA, bovine serum albumin (BSA), an engineered albumin (e.g., Veltis® from Novozymes), a casein, an insulin, a hemoglobin, a lysozyme, an α-2-macroglobulin, a fibronectin, a vitronectin, a fibrinonectin, a lipase, mutants thereof, or fragments thereof (including fragments of mutants). In certain embodiments, the stabilizing amino acid sequence can be recombinantly made (e.g., in CHO cells) or can be purified from a natural source.

In yet other embodiments, the stabilizing amino acid sequence can be BSA or HSA.

In some embodiments, combinations of $R_1$, $R_2$, X, n, and Y (i.e., where Z (e.g., HSA or BSA) is not yet attached), can include, for example:

(a) $R_1$ is allyl; $R_2$ is H; X is methyl; n is 1; Y is DAsp-Asp-DAsp-Asp-DSer-Ser-Thr-Ser-DSer-Lys-DSer-NH$_2$; and where Y can be attached to Z via reaction with the side group amine on the Lysine;

(b) $R_1$ is allyl; $R_2$ is H; X is dimethyl substituted $C_1$ (i.e., $R_3$ and $R_4$ are both methyl); n is 1; Y is DAsp-Asp-DAsp-Asp-DSer-Ser-Thr-Ser-DSer-Lys-DSer-NH$_2$; and where Y can be attached to Z via reaction with the side group amine on the Lysine;

(c) $R_1$ is allyl; $R_2$ is H; X is bivalent benzene; n is 1; Y is DAsp-Asp-DAsp-Asp-DSer-Ser-Thr-Ser-DSer-Lys-DSer-NH$_2$; and where Y can be attached to Z via reaction with the side group amine on the Lysine;

(d) $R_1$ is allyl; $R_2$ is H; X is methyl; n is 1; Y is

and where Y can be attached to Z via reaction with the maleimide;

(e) $R_1$ is allyl; $R_2$ is H; X is dimethyl substituted $C_1$ (i.e., $R_3$ and $R_4$ are both methyl); n is 1; Y is

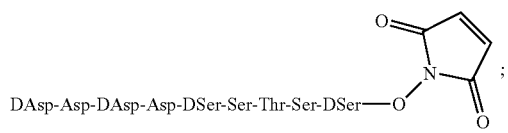

and where Y can be attached to Z via reaction with the maleimide;

(f) $R_1$ is allyl; $R_2$ is H; X is bivalent benzene; n is 1; Y is

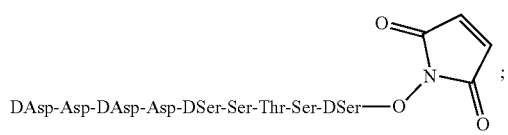

and where Y can be attached to Z via reaction with the maleimide;

(g) $R_1$ is allyl; $R_2$ is H; X is methyl; n is 1; Y is

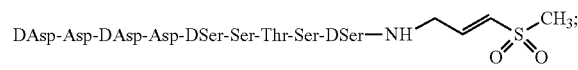

and where Y can be attached to Z via reaction with the vinyl sulfone;

(h) $R_1$ is allyl; $R_2$ is H; X is dimethyl substituted $C_1$ (i.e., $R_3$ and $R_4$ are both methyl); n is 1; Y is

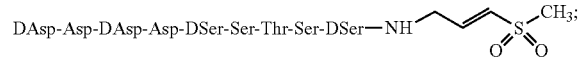

and where Y can be attached to Z via reaction with the vinyl sulfone;

(i) $R_1$ is allyl; $R_2$ is H; X is bivalent benzene; n is 1; Y is

DAsp-Asp-DAsp-Asp-DSer-Ser-Thr-Ser-DSer—NH and where Y can be attached to Z via reaction with the vinyl sulfone;

(j) $R_1$ is allyl; $R_2$ is H; X is methyl; n is 1; Y is

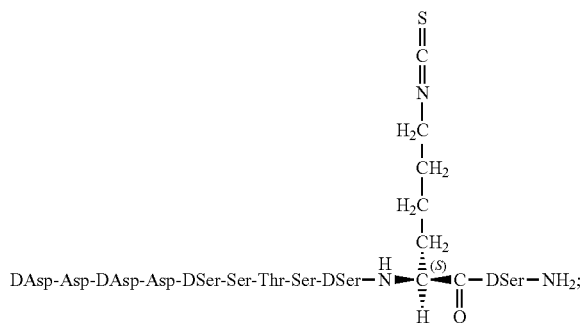

and where Y can be attached to Z via reaction with the isothiocyanate;

(k) $R_1$ is allyl; $R_2$ is H; X is dimethyl substituted $C_1$ (i.e., $R_3$ and $R_4$ are both methyl); n is 1; Y is

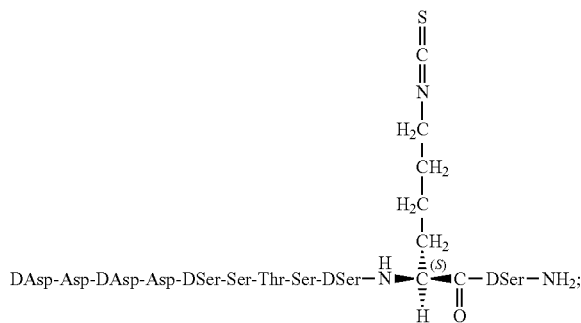

and where Y can be attached to Z via reaction with the isothiocyanate; or (l) $R_1$ is allyl; $R_2$ is H; X is bivalent benzene; n is 1; Y is

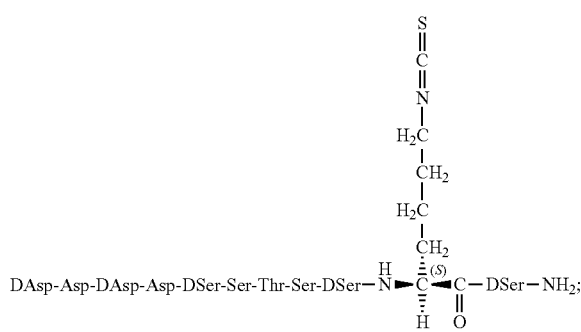

and where Y can be attached to Z via reaction with the isothiocyanate.

In some embodiments, Formula (I) can be, for example:

(a) $R_1$ is allyl; $R_2$ is methyl; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;

(b) $R_1$ is allyl; $R_2$ is methyl; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;

(c) $R_1$ is allyl; $R_2$ is methyl; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is somatostatin;

(d) $R_1$ is allyl; $R_2$ is methyl; X is bivalent benzene; n is 1; m is 1; Y is DSer-Ser-Thr-Ser-DSer-Lys-DSer-NH$_2$; and Z is BSA or HSA;

(e) $R_1$ is allyl; $R_2$ is methyl; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$;

(f) $R_1$ is allyl; $R_2$ is H; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;

(g) $R_1$ is allyl; $R_2$ is H; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;

(h) $R_1$ is allyl; $R_2$ is H; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is somatostatin;

(i) $R_1$ is allyl; $R_2$ is H; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is BSA or HSA;

(j) $R_1$ is allyl; $R_2$ is H; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$;

(k) $R_1$ is ethyl; $R_2$ is H; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;

(l) $R_1$ is ethyl; $R_2$ is H; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;

(m) $R_1$ is ethyl; $R_2$ is H; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is somatostatin;

(n) $R_1$ is ethyl; $R_2$ is H; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is BSA or HSA;

(o) $R_1$ is ethyl; $R_2$ is H; X is bivalent benzene; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$;

(p) $R_1$ is allyl; $R_2$ is methyl; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;

(q) $R_1$ is allyl; $R_2$ is methyl; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;

(r) $R_1$ is allyl; $R_2$ is methyl; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is somatostatin;

(s) $R_1$ is allyl; $R_2$ is methyl; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is BSA or HSA;

(t) $R_1$ is allyl; $R_2$ is methyl; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$;

(u) $R_1$ is allyl; $R_2$ is H; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;

(v) $R_1$ is allyl; $R_2$ is H; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;

(w) $R_1$ is allyl; $R_2$ is H; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is somatostatin;

(x) $R_1$ is allyl; $R_2$ is H; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is BSA or HSA;

(y) $R_1$ is allyl; $R_2$ is H; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$;

(z) $R_1$ is ethyl; $R_2$ is H; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;

(aa) $R_1$ is ethyl; $R_2$ is H; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;

(bb) $R_1$ is ethyl; $R_2$ is H; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is somatostatin;

(cc) $R_1$ is ethyl; $R_2$ is H; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is BSA or HSA; or (dd) $R_1$ is ethyl; $R_2$ is H; X is unsubstituted $C_1$; n is 1; m is 1; Y is DSer-Ser-Thr-Ser-DSer-Lys-DSer-NH$_2$, DSer-Ser-Thr-Ser-DSer-Lys-DSer-Asp-DAsp-Asp-DAsp-NH$_2$, or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$.

In still other embodiments, Formula (I) can be, for example:

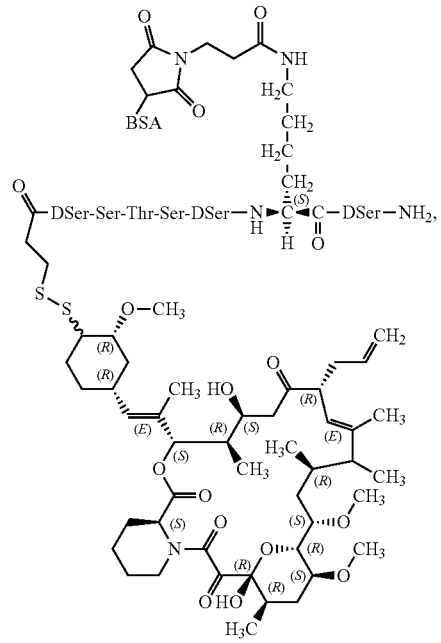

where the attachment to the BSA is via a BSA cysteine thiol or via a BSA amine;

37
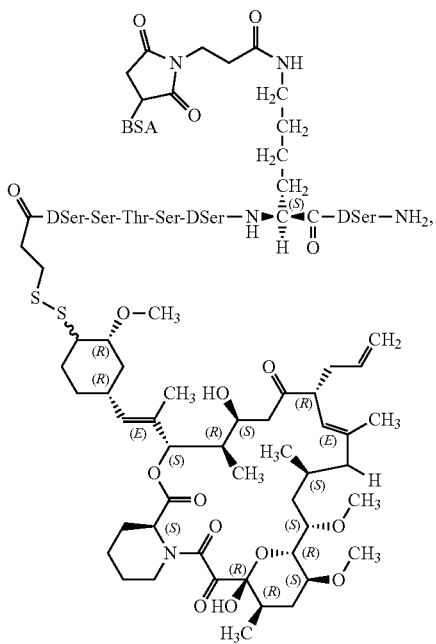
where the attachment to the BSA is via a BSA cysteine thiol or via a BSA amine;
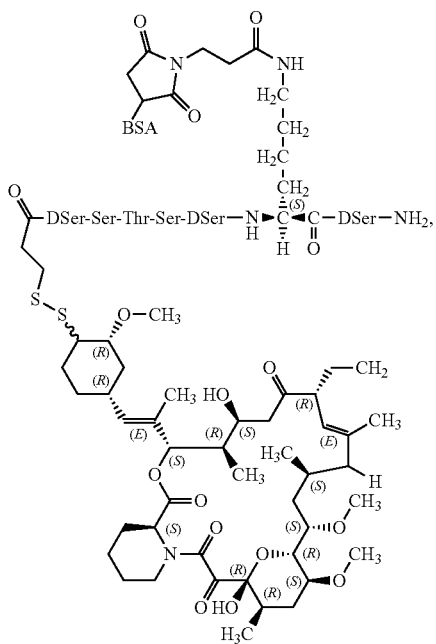
where the attachment to the BSA is via a BSA cysteine thiol or via a BSA amine;
38
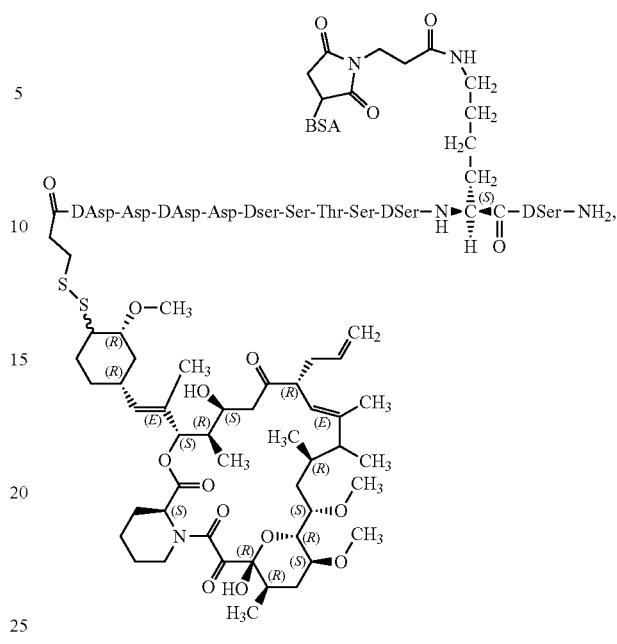
where the attachment to the BSA is via a BSA cysteine thiol or via a BSA amine;
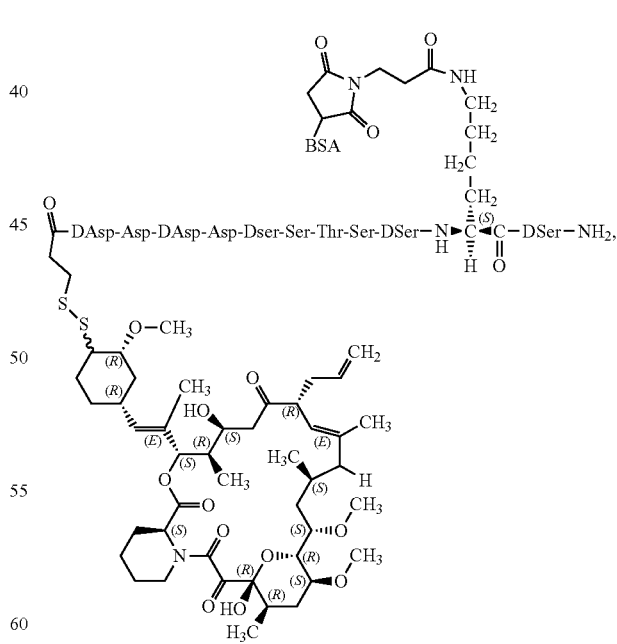
where the attachment to the BSA is via a BSA cysteine thiol or via a BSA amine;

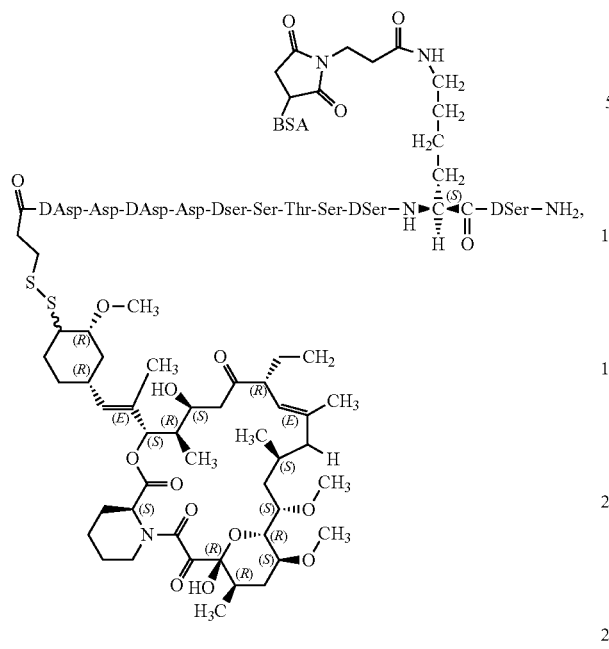
where the attachment to the BSA is via a BSA cysteine thiol or via a BSA amine;
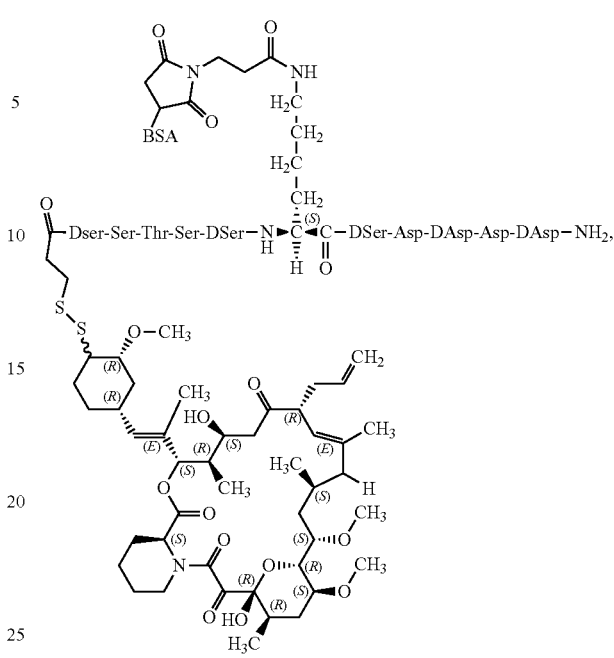
where the attachment to the BSA is via a BSA cysteine thiol or via a BSA amine;
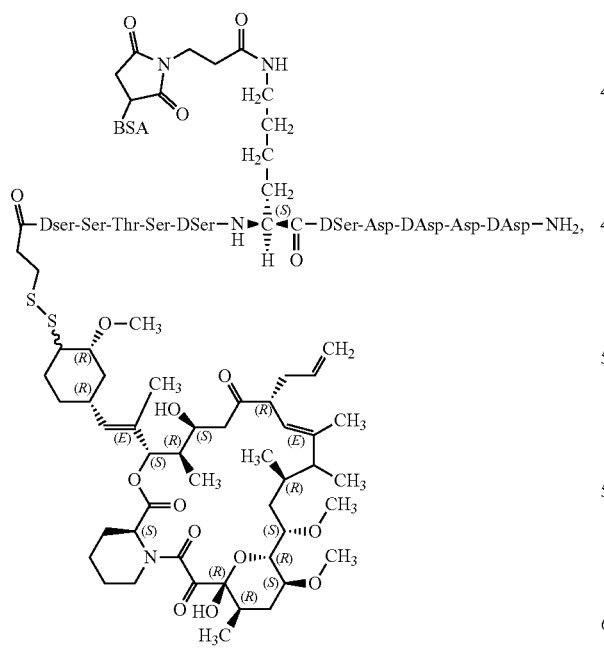
where the attachment to the BSA is via a BSA cysteine thiol or via a BSA amine;
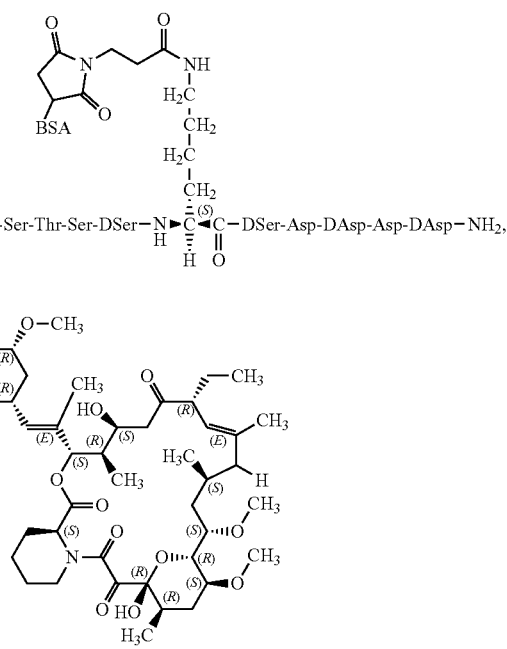
where the attachment to the BSA is via a BSA cysteine thiol or via a BSA amine;

41
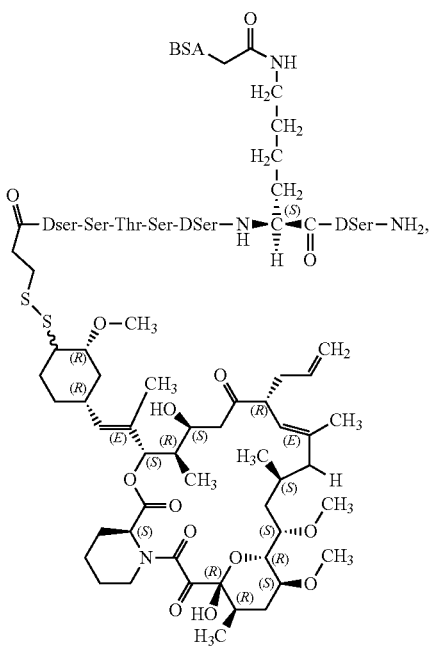
where the attachment to the BSA is via a BSA cysteine thiol or via a BSA amine;
42
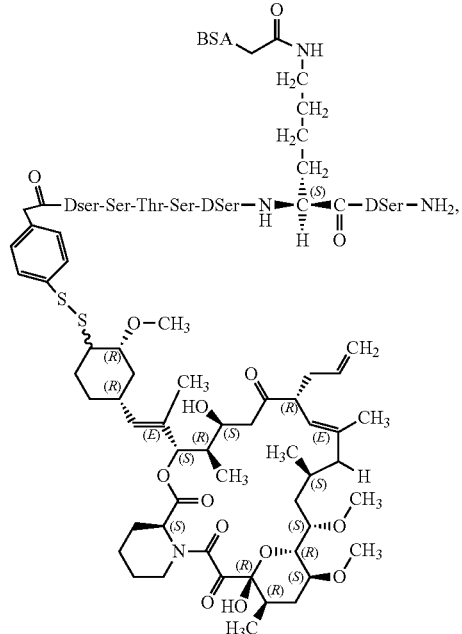
where the attachment to the BSA is via a BSA cysteine thiol or via a BSA amine;
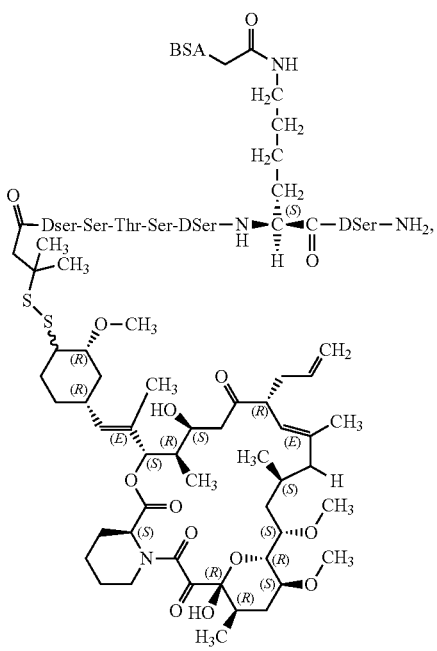
where the attachment to the BSA is via a BSA cysteine thiol or via a BSA amine;
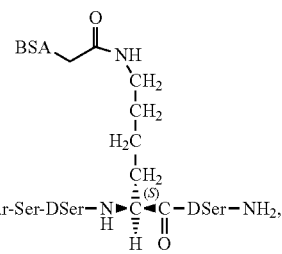
where the attachment to the BSA is via a BSA cysteine thiol or via a BSA amine;

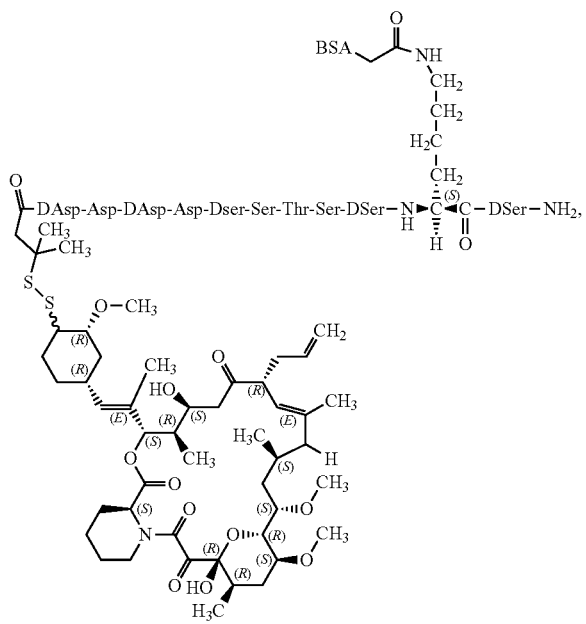

where the attachment to the BSA is via a BSA cysteine thiol or via a BSA amine; or

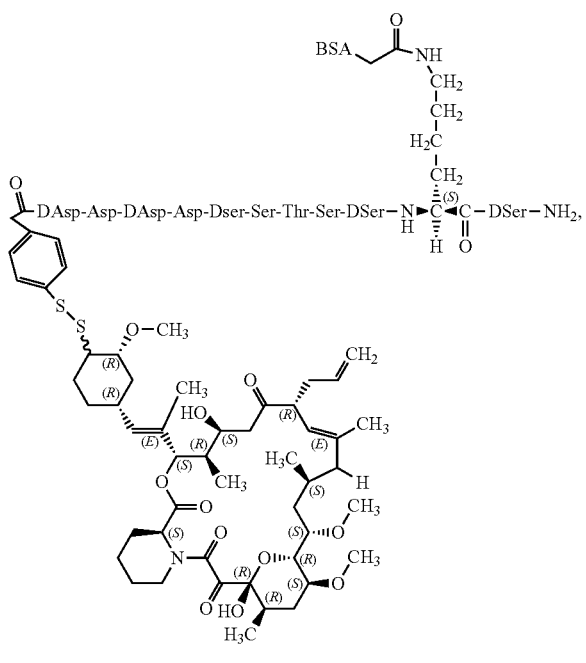

where the attachment to the BSA is via a BSA cysteine thiol or via a BSA amine.

In still other embodiments, Formula (I) can be, for example:

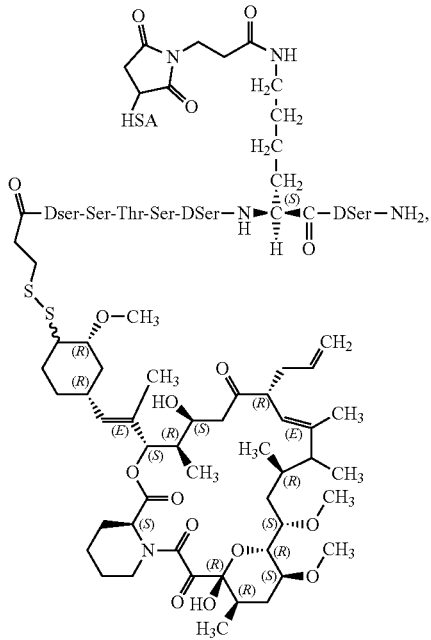

where the attachment to the HSA is via an HSA cysteine thiol or via an HSA amine;

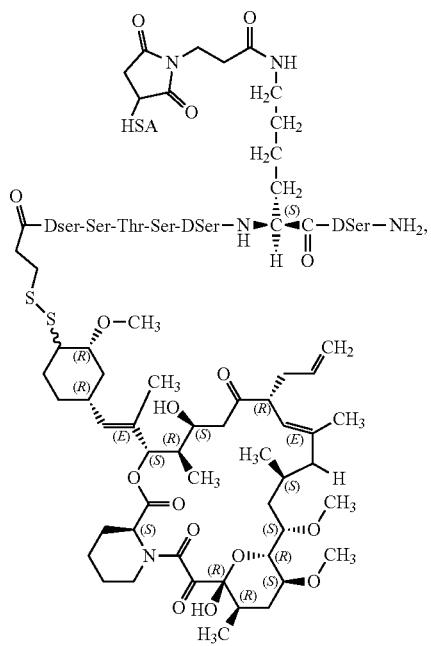

where the attachment to the HSA is via an HSA cysteine thiol or via an HSA amine;

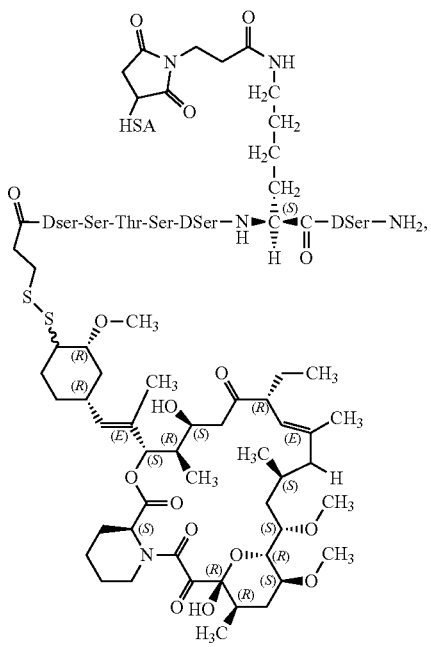
where the attachment to the HSA is via an HSA cysteine thiol or via an HSA amine;
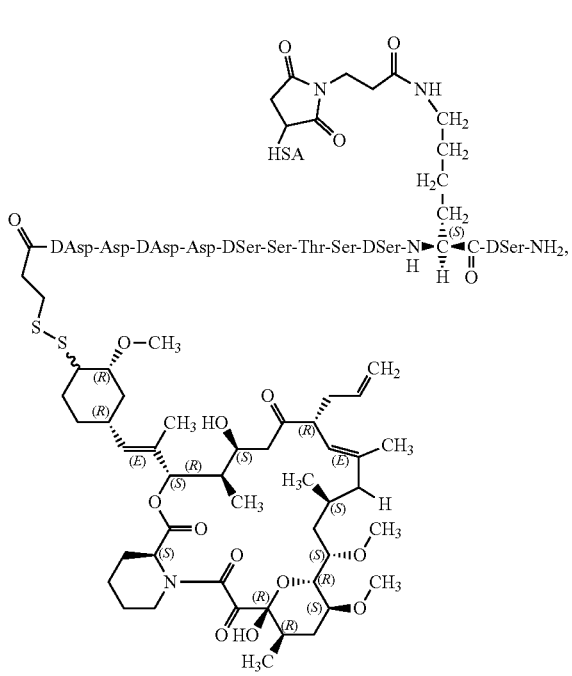
where the attachment to the HSA is via an HSA cysteine thiol or via an HSA amine;
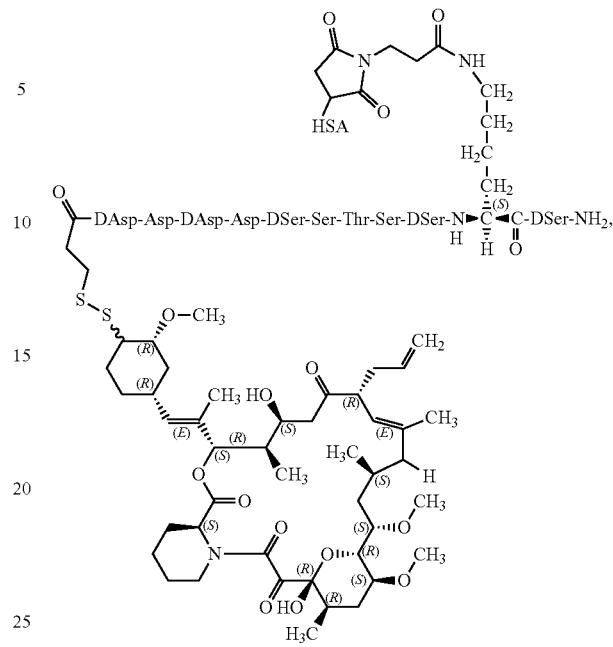
where the attachment to the HSA is via an HSA cysteine thiol or via an HSA amine;
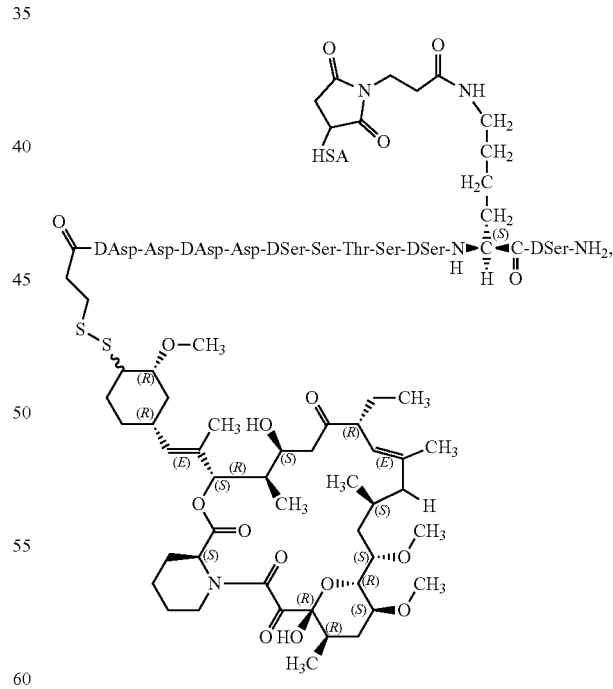
where the attachment to the HSA is via an HSA cysteine thiol or via an HSA amine;

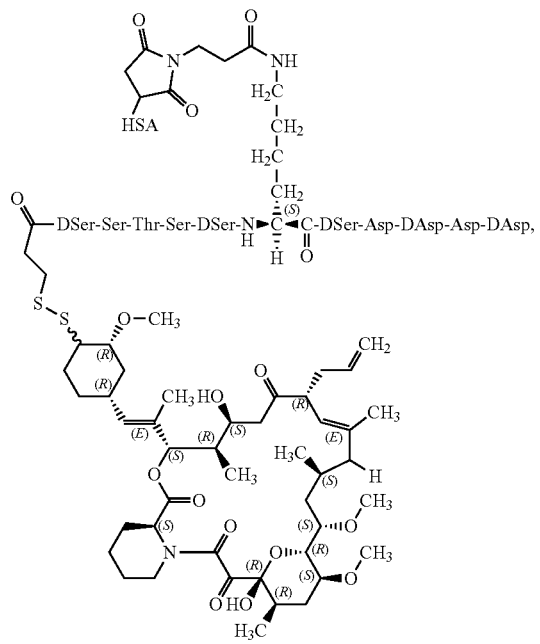
where the attachment to the HSA is via an HSA cysteine thiol or via an HSA amine;
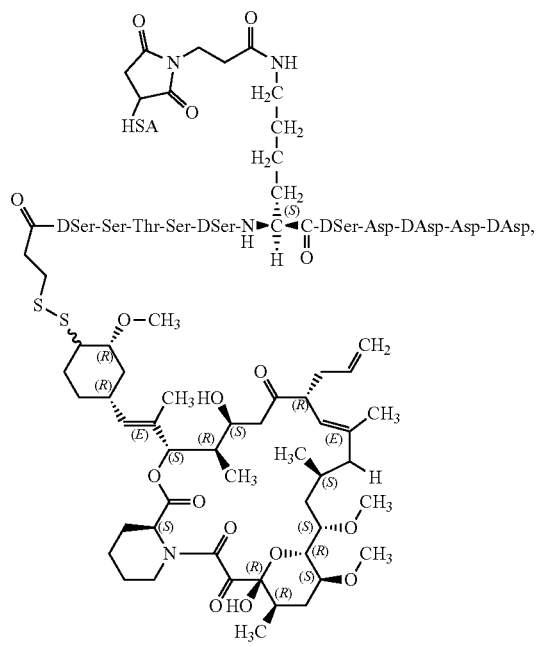
where the attachment to the HSA is via an HSA cysteine thiol or via an HSA amine;
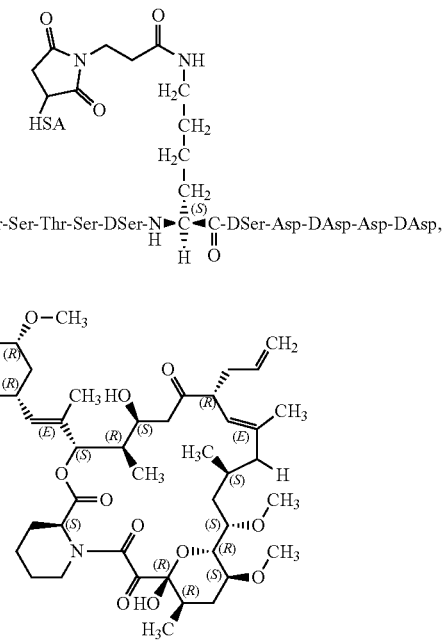
where the attachment to the HSA is via an HSA cysteine thiol or via an HSA amine;
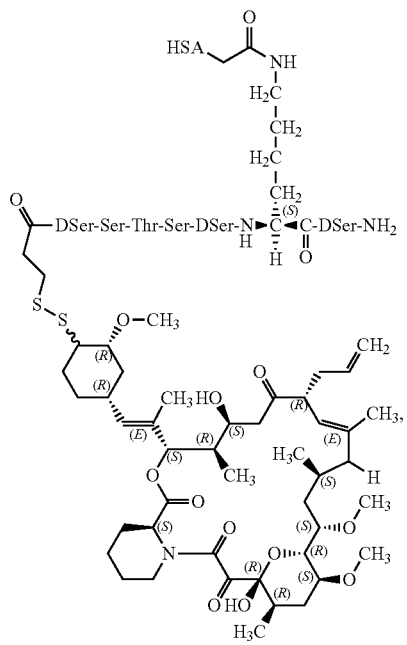
where the attachment to the HSA is via an HSA cysteine thiol or via an HSA amine;

49
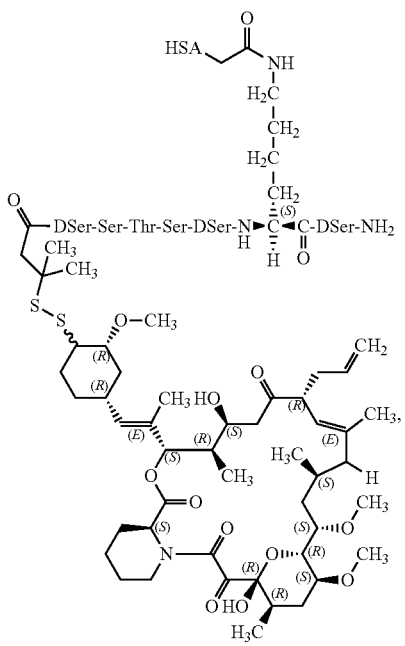
where the attachment to the HSA is via an HSA cysteine thiol or via an HSA amine;
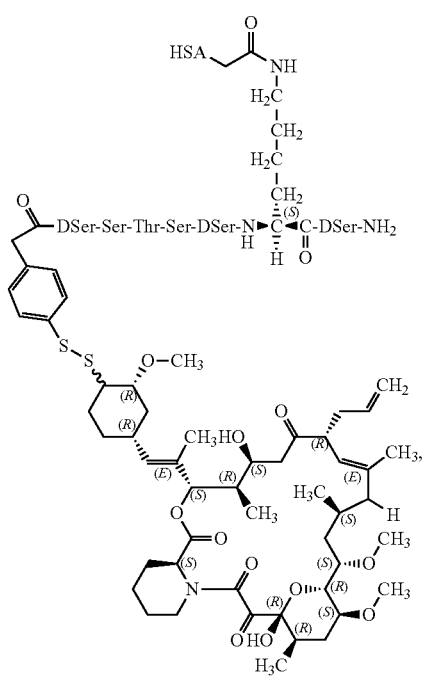
where the attachment to the HSA is via an HSA cysteine thiol or via an HSA amine;
50
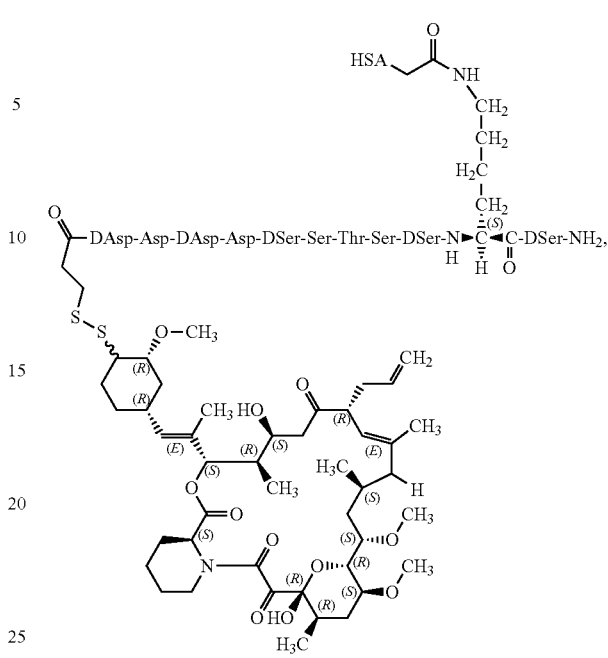
where the attachment to the HSA is via an HSA cysteine thiol or via an HSA amine;
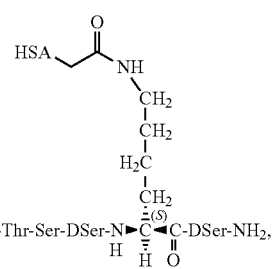
where the attachment to the HSA is via an HSA cysteine thiol or via an HSA amine;

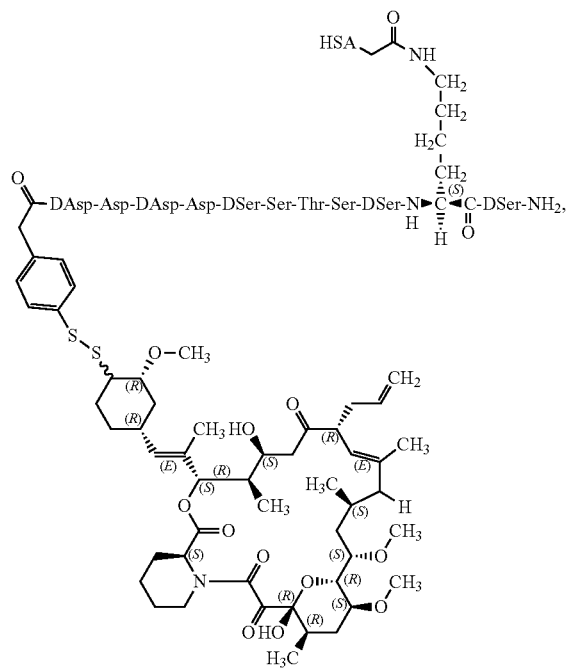
where the attachment to the HSA is via an HSA cysteine thiol or via an HSA amine;
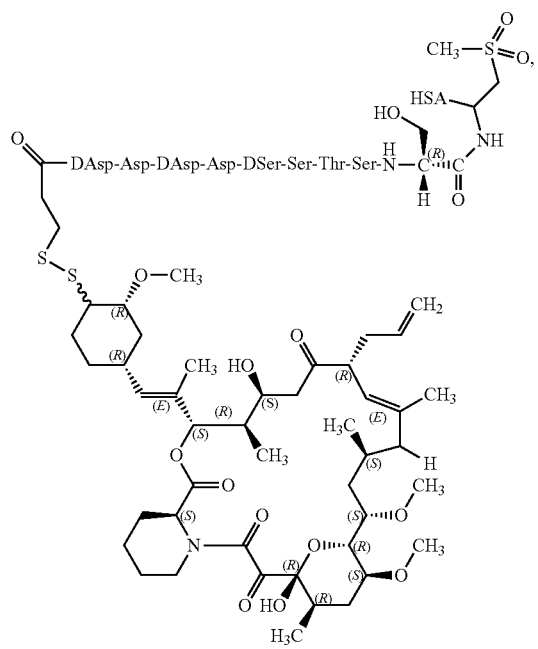
where the attachment to the HSA is via an HSA cysteine thiol or via an HSA amine; or
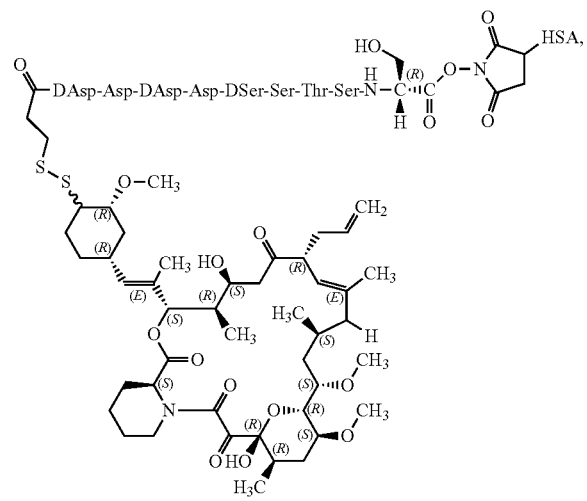
where the attachment to the HSA is via an HSA cysteine thiol or via an HSA amine;
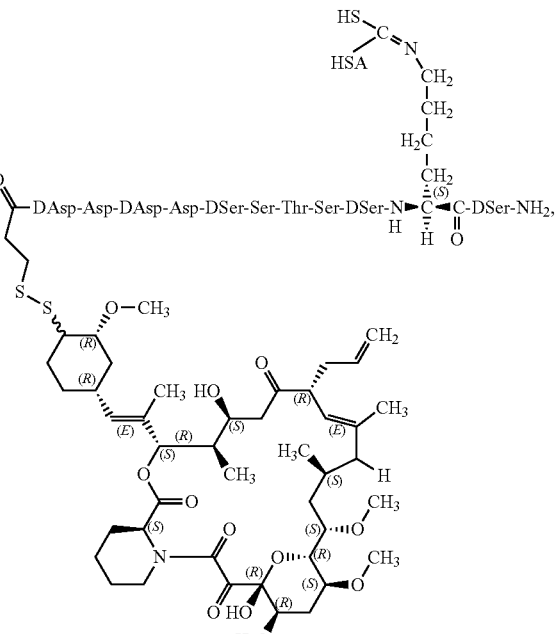
where the attachment to the HSA is via an HSA cysteine thiol or via an HSA amine.

Compositions Including Pharmaceutical Compositions

One or more compounds of Formula (I) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

One or more compounds of Formula (I) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising compounds of Formula (I). In certain embodiments, the composition is a pharmaceutical composition, such as compositions that are suitable for administration to animals (e.g., mammals, primates, monkeys, humans, canine, feline, porcine, mice, rabbits, or rats). In some instances, the pharmaceutical composition is non-toxic, does not cause side effects, or both. In some embodiments, there may be inherent side effects (e.g., it may harm the patient or may be toxic or harmful to some degree in some patients).

In some embodiments, compounds of Formula (I) can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, for the organ, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or *arachis* oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release the active ingredient (e.g., one or more compounds of Formula (I)) substantially immediately upon the administration or any substantially predetermined time or time after administration. Such formulations can include, for example, controlled release formulations such as various controlled release compositions and coatings.

Other formulations (e.g., formulations of a pharmaceutical composition) can, in certain embodiments, include those incorporating the drug (or control release formulation) into food, food stuffs, feed, or drink.

Other embodiments of the invention can include methods of administering or treating an animal (e.g., human or canine), which can involve treatment with an amount of at least one compound of Formula (I) that is effective to treat an autoimmune disease or organ rejection that the animal has, or is suspected of having, or is susceptible to, or to bring about a desired physiological effect. In some embodiments, the composition or pharmaceutical composition comprises at least one compound of Formula (I) which can be administered to an animal (e.g., mammals, primates, monkeys, or humans) in an amount of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, some animals (e.g., mammals, mice, rabbits, feline, porcine, or canine) can be administered a dosage of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the compounds of the invention can be administered in combination with one or more other therapeutic agents for a given autoimmune disease or organ rejection.

In some embodiments, the compositions can include a dose (e.g., unit dose) of one or more compounds of Formula (I) in combination with a pharmaceutically acceptable carrier and, in addition, can include other medicinal agents, pharmaceutical agents, carriers, adjuvants, diluents, excipients, or combinations thereof. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

Parenteral administration, if used, is generally characterized by injection. Sterile injectables can be prepared in conventional forms, either as liquid solutions or suspensions, solid forms suitable for solution or suspension in liquid prior to injection, or as emulsions.

Methods for Administering and for Treatment

The compounds of Formula (I) can be administered to animals by any number of suitable administration routes or formulations. The compounds of Formula (I) can also be used to treat animals for a variety of autoimmune diseases or organ rejections. Animals include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject" refers to both human and animal subjects.

The route of administration of the compounds of Formula (I) of the invention can be of any suitable route. Administration routes can be, but are not limited to the oral route, the parenteral route, the cutaneous route, the nasal route, the rectal route, the vaginal route, and the ocular route. In other embodiments, administration routes can be parenteral administration, a mucosal administration, intravenous administration, subcutaneous administration, topical administration, intradermal administration, oral administration, sublingual administration, intranasal administration, or intramuscular administration. The choice of administration route can depend, for example, on the identity of the compound of Formula (I) (e.g., the physical and chemical properties of the compound of Formula (I)) as well as the age and weight of the animal, the transplant organ, the amount of time past after organ transplant, the particular disease, and the severity of the disease. Of course, combinations of administration routes can be administered, as desired.

Some embodiments of the invention include methods for providing a subject with a composition comprising a compound of Formula (I) described herein (e.g., a pharmaceutical composition) which comprises one or more administrations of one or more such compositions; the compositions may be the same or different if there is more than one administration and the routes of administration may be the same or different if there is more than one administration.

Some embodiments of the invention include methods for treating a subject with a composition comprising a compound of Formula (I) described herein (e.g., a pharmaceutical composition) which comprises one or more administrations of one or more such compositions; the compositions may be the same or different if there is more than one administration and the routes of administration may be the same or different if there is more than one administration.

Animals that can be treated include but are not limited to mammals, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. A subject susceptible to an autoimmune disease or to an organ rejection can be a human subject or an animal subject. In some instances, the animal (e.g., human or canine) is in need of the treatment (e.g., a prophylactic treatment) for an autoimmune disease or for an organ rejection (e.g., a prophylactic treatment prior to transplant).

As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. As used herein, reference to "treating" an animal includes but is not limited to prophylactic treatment and therapeutic treatment. Any of the compositions (e.g., pharmaceutical compositions) described herein can be used to treat an animal (e.g., human or canine). In some embodiments, the treatment comprises suppressing the immune system, suppressing IL-2 production, or both.

Diseases that can be treated in an animal (e.g., mammals, porcine, canine, avian (e.g., chicken), bovine, feline, primates, monkeys, rabbits, and humans) using the compounds of Formula (I) include, but are not limited to autoimmune diseases and organ rejection (e.g., an allograft organ transplant, a xenograft organ transplant, a cloned organ transplant, or a 3D printed organ transplant). Autoimmune diseases that can be treated using the compounds of Formula (I) include but are not limited to Myocarditis, Postmyocardial infarction syndrome, Postpericardiotomy syndrome, Subacute bacterial endocarditis, Kidney, Anti-Glomerular Basement Membrane nephritis, Interstitial cystitis, Lupus nephritis, Autoimmune hepatitis, Primary biliary cirrhosis, Primary sclerosing cholangitis, Antisynthetase syndrome, Skin, Alopecia Areata, Autoimmune Angioedema, Autoimmune progesterone dermatitis, autoimmune urticaria, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease, Morphea, Pemphigus vulgaris, Pityriasis lichenoides et varioliformis acuta, Mucha-Habermann disease, Psoriasis, Systemic scleroderma, Vitiligo, Addison's disease, Autoimmune polyendocrine syndrome, Autoimmune polyendocrine syndrome type 3, Autoimmune pancreatitis, Diabetes mellitus type 1, Autoimmune thyroiditis, Ord's thyroiditis, Graves' disease, Autoimmune oophoritis, Endometriosis, Autoimmune orchitis, Sjogren's sysndrome, Autoimmune enteropathy, inflammatory bowel disease, Celiac disease, Crohn's disease, Microscopic colitis, Ulcerative colitis, Antiphospholipid syndrome, Aplastic anemia, Autoimmune hemolytic anemia, Autoimmune lymphoproliferative syndrome, Autoimmune neutropenia, Autoimmune thrombocytopenic purpura, Cold agglutinin disease, Essential mixed cryoglobulinemia, Evans syndrome, IgG4-related systemic disease, Paroxysmal nocturnal hemoglobinuria, Paroxysmal nocturnal hemoglobinuria, Pernicious anemia, Pure red cell aplasia, Thrombocytopenia, Adiposis dolorosa, Adult-onset Still's disease, Ankylosing Spondylitis, CREST syndrome, Drug-induced lupus, Enthesitis-related arthritis, osteoarthritis, Eosinophilic fasciitis, Felty syndrome, Juvenile arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Sarcoidosis, Schnitzler syndrome, Systemic Lupus Erythematosus, Undifferentiated connective tissue disease, Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis, Acute motor axonal neuropathy, Anti-N-Methyl-D-Aspartate Receptor Encephalitis, Balo concentric sclerosis, Bickerstaff's encephalitis, Chronic inflammatory demyelinating polyneuropathy, Guillain-Barré syndrome, Hashimoto's encephalopathy, Idiopathic inflammatory demyelinating diseases, Lamber-Eaton myasthenic syndrome, Multiple sclerosis, Pediatric Autoimmune Neuropsychiatric Disorder Associated with *Streptococcus*, Progressive inflammatory neuropathy, Restless leg syndrome, Stiff person syndrome, Sydenham chorea, Transverse myelitis, Autoimmune retinopathy, Autoimmune uveitis, Cogan syndrome, Graves ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, Tolosa-Hunt syndrome, Autoimmune inner ear disease, Meniere's disease, Anti-neutrophil cytoplasmic antibody-associated vasculitis, Behçet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, Polyarteritis nodosa, Polymyalgia rheumatica, Urticarial vasculitis, Vasculitis, Chronic fatigue syndrome, Complex regional pain syndrome, Eosinophilic esophagitis, Gastritis, POEMS syndrome, Raynaud phenomenon, Primary immunodeficiency, or Pyoderma gangrenosum. In some embodiments, autoimmune diseases that can be treated using the compounds of Formula (I) are ulcerative colitis, inflammatory bowel disease, Crohn's disease, arthritis, osteoarthritis, or rheumatoid arthritis.

Diseases, as defined herein, include organ rejection (e.g., an allograft organ transplant or a xenograft organ transplant). Allograft organ transplant can be from a cadaver, a living related donor, or a living unrelated donor. Organ rejection that can be treated using the compounds of Formula (I) can be, for example, hyperacute rejection, acute rejection, or chronic rejection. Organ rejection that can be treated using the compounds of Formula (I) can occur when any organ is transplanted (e.g., an allograft organ transplant or a xenograft organ transplant), including but not limited to kidney, liver, heart, small bowel, pancreas, lung, trachea, skin, cornea, bone marrow, or limb transplants. In some embodiments, organ rejection that can be treated using the compounds of Formula (I) can occur when any organ is transplanted (e.g., an allograft organ transplant or a xenograft organ transplant) and are kidney, liver, or heart.

As related to treating an autoimmune disease, treating can include but is not limited to prophylactic treatment (e.g., preventing or ameliorating future disease) and therapeutic treatment. As such, treatment can include, but is not limited to: conferring protection against an autoimmune disease; preventing an autoimmune disease; reducing the risk of an autoimmune disease; ameliorating or relieving symptoms of an autoimmune disease; reducing the activity of an animal's immune system; inhibiting the development or progression of an autoimmune disease; inhibiting or preventing the onset of symptoms associated with an autoimmune disease; reducing the severity of an autoimmune disease; causing a regression of an autoimmune disease or one or more of the symptoms associated with an autoimmune disease; or combinations thereof. In some embodiments, treating does not include prophylactic treatment (e.g., preventing or ameliorating future disease).

Symptoms associated with an autoimmune disease are known to those of ordinary skill in the art and can include, without limitation, those described herein and known to those of ordinary skill in the art. The presence of an autoimmune disease can be assessed using any suitable method, including those known to those of ordinary skill in the art. In some cases, the presence of an autoimmune disease can be determined using any suitable method including those methods currently known to those of ordinary skill in the art.

As related to treating an organ rejection, treating can include but is not limited to prophylactic treatment (e.g., preventing or ameliorating future organ rejection) and therapeutic treatment. Organ rejection is also referred to as graft rejection, tissue rejection, or transplant rejection. Treatment can include, but is not limited to: conferring protection against organ rejection prior to transplant or after transplant; preventing organ rejection prior to transplant or after transplant; reducing the risk of an organ rejection prior to transplant or after transplant; ameliorating or relieving symptoms of an organ rejection; reducing the activity of an animal's immune system; inhibiting the development or progression of an organ rejection; inhibiting or preventing the onset of symptoms associated with organ rejection prior to transplant or after transplant; reducing the severity of organ rejection; causing a regression of an organ rejection prior after transplant or one or more of the symptoms associated with organ rejection; or combinations thereof. In some embodiments, treating does not include prophylactic treatment (e.g., preventing or ameliorating future organ rejection).

Symptoms associated with an organ rejection are known to those of ordinary skill in the art and can include, without limitation, those described herein and known to those of ordinary skill in the art. The presence of an organ rejection can be assessed using any suitable method, including those known to those of ordinary skill in the art. For example, organ rejection can be assessed by changes in organ function (e.g., a decrease in function), general discomfort of the animal, flu-like symptoms (e.g., chills, body aches, nausea, cough, or shortness of breath), high blood sugar (e.g., for a pancreas transplant), less urine released (e.g., for a kidney transplant), shortness of breath (e.g., a heart transplant), less ability to exercise (e.g., a heart transplant), yellow skin (e.g., liver transplant), easy bleeding (e.g., liver transplant), by biopsy of the transplanted organ, or combinations thereof.

Treatment of an animal can occur using any suitable administration method (such as those disclosed herein) and using any suitable amount of using the compounds of Formula (I) (such as those disclosed herein). In some embodiments, methods of treatment comprise treating an animal (e.g., human or canine) for an autoimmune disease, for symptoms of an autoimmune disease, for an organ rejection, for symptoms of an organ rejection, or combinations thereof. Some embodiments of the invention include a method for treating a subject (e.g., an animal such as a human or primate) with a composition comprising any of the compounds of Formula (I) described herein (e.g., a pharmaceutical composition) which comprises one or more administrations of one or more such compositions; the compositions may be the same or different if there is more than one administration, and in some instances, the treatment can occur about once per day, about twice per day, about three times per day, about four times per day, about five times per day, about six times per day, about eight times per day, about twelve times per day, about five times per week, about three times per week, about twice per week, or about once per week. In certain embodiments, treatment occurs before organ transplant, during organ transplant, after organ transplant, or combinations thereof; the compositions may be the same or different if there is more than one administration and the composition (e.g., dosage and one or more active ingredients) can, in some instances, vary depending on the amount of time before or after organ transplant. In some embodiments, treatment may occur for the rest of the animal's (e.g., human's or canine's) life, although that treatment can sometimes stay the same or it may vary throughout the lifetime of the animal.

In some embodiments, the method of treatment includes administering an effective amount of a composition comprising a compound of Formula (I). As used herein, the term "effective amount" refers to a dosage or a series of dosages sufficient to affect treatment (e.g., to treat an autoimmune disease or to treat organ rejection) in an animal. In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular additional therapies being used (if applicable), administration protocol, time after organ transplant, the transplant organ type, the transplant organ source, the specific autoimmune disease, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of at least one compound of Formula (I) (which can be administered to an animal such as mammals, primates, monkeys or humans) can be an amount of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, an effective amount of at least one compound of Formula (I) (which can be administered to an animal such as mammals, mice, rabbits, feline, porcine, or canine) can be an amount of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg.

"Therapeutically effective amount" means an amount effective to achieve a desired and/or beneficial effect. An effective amount can be administered in one or more administrations. For some purposes of this invention, a therapeutically effective amount is an amount appropriate to treat an indication, such as but not limited to lowering the activity of the immune system in an animal (e.g., to lower the risk of organ rejection or to treat an autoimmune disease). By treating an indication is meant achieving any desirable effect, such as one or more of palliate, ameliorate, stabilize, reverse, slow, or delay disease or organ rejection progression, increase the quality of life, or to prolong life. Such achievement can be measured by any suitable method.

In some embodiments, the treatments disclosed herein can comprise use of other drugs (e.g., antibiotics) or therapies for treating an autoimmune disease or for treating organ rejection (e.g., an allograft organ transplant, a xenograft organ transplant, a cloned organ transplant, or a 3D printed organ transplant). For example, antibiotics can be used to treat infections and can be combined with a compound of Formula (I) for treating an autoimmune disease or for treating organ rejection (e.g., an allograft organ transplant, a xenograft organ transplant, a cloned organ transplant, or a 3D printed organ transplant). In other embodiments, one or more of immunosuppressive drugs (e.g., azathioprine), steroids (e.g., corticosteroids, adrenal corticosteroid, or glucocorticoids), mycophenolates (e.g., mycophenolate mofetil), and IL-2 receptor inhibitors (e.g., daclizumab or basiliximab) can be used as part of the treatment regime (i.e., in addition to administration of one or more compounds of Formula (I)) for treating an autoimmune disease or for treating an organ rejection (e.g., an allograft organ transplant, a xenograft organ transplant, a cloned organ transplant, or a 3D printed organ transplant). In other embodiments, a drug or therapy or additional treatment can be used to modulate (e.g, increase, decrease, or alter) the intended target, upregulate the intended target, increase the number of the intended targets, or otherwise modulate the ability to target the intended target of one or more compounds of Formula (I).

Method for Preparing Compounds of Formula (I)

Some embodiments of the present invention include methods for the preparation of compounds of Formula (I). In certain embodiments, a compound of Formula (I) can be prepared comprising reacting a compound of Formula (II)

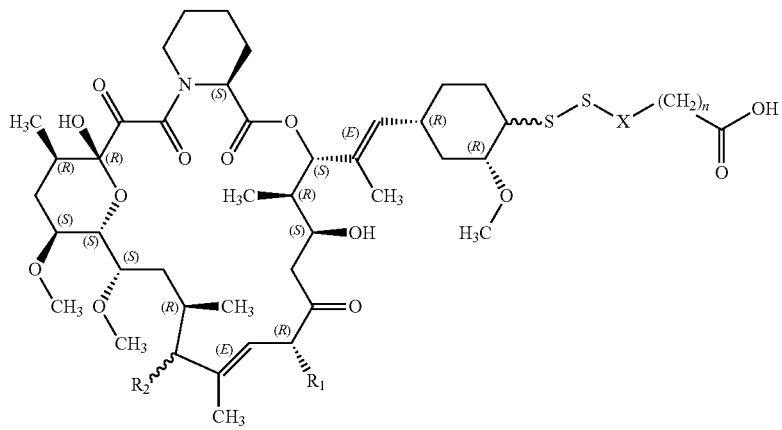

(II)

with a W amino acid sequence attached to a solid support (e.g., via the C-terminal amino acid of W or the carboxylic acid of the C-terminal amino acid of W). $R_1$, $R_2$, X, and n are that same as that defined for Formula (I). Formula (II) can be prepared using any suitable method, including, but not limited to those found in the Examples. Any suitable reaction conditions can be used to react a compound of Formula (II) to W attached to a solid support, including but not limited to: mixing W-solid support with 0.16 mmol of Formula (II), DIC (0.48 mmol; 3 equiv) and HBOt (0.48 mmol; 3 equiv) in N-methyl pyrolidone and allowing to react overnight, and optionally followed by dichloromethane wash.

In certain embodiments, one or more of the amino acids of W can comprise one or more protecting groups (e.g., a protecting group attached to a side chain of the amino acid). In some embodiments, the W amino acid sequence without its one or more protecting groups (i.e., if W has any protecting groups) can be identical to (1) a Y' amino acid sequence, which is a pre-modified Y amino acid sequence (i.e., prior to an amino acid modification to result in Y, such as, for example if one or more modifications are needed to attach Y to Z), (2) a Y amino acid sequence, (3) a (Y—Z)' amino acid sequence, which is a pre-modified Y—Z amino acid sequence (e.g., fused or conjugated)(i.e., prior to an amino acid modification of Y or Z, to result in Y—Z), or (4) a Y—Z amino acid sequence (e.g., fused or conjugated). Y and Z are the same as that defined for Formula (I).

Protecting groups include but are not limited to N-terminal protecting groups, C-terminal protecting groups, or side chain protecting groups. In some embodiments, protecting groups can be t-Boc protecting groups, Fmoc protecting groups, benzyloxy-carbonyl protecting groups, allyloxycarbonyl protecting groups, lithographic protecting groups, benzyl protecting groups, tert-butyl protecting groups, protecting groups specific to one or more side chains, protecting groups specific to one or more amino acid modifications (e.g., where the amino acid modification is a maleimide modification of the Lys side chain or a bromoacetamide modification of the Lys side chain), 4-Methyltrityl (Mtt), or combinations thereof. In other embodiments, protecting groups can be chosen based upon the synthetic method (e.g., Fmoc method or tBoc method), the amino acid sequence (e.g., the other amino acids in the amino acid sequence), the other protecting groups used, the ability to withstand multiple cycles during amino acid synthesis, the ability to withstand the reaction of Formula (II) with W, the ability to withstand treatment with weak acid, the ability to be removed by treatment with strong acid, the ability to be removed under the one or more desired conditions (e.g., solution conditions such as but not limited to acidic pH), or a combination thereof. In some embodiments, the protecting group can be Fmoc, tert-butyl protecting groups, 4-Methyltrityl (Mtt), or combinations thereof.

The solid support (also referred to as resin) can be, but is not limited to, a gel-type support (e.g., polystyrene, styrene cross-linked with 1-2% divinylbenzene, polyacrylamide, polyethylene glycol (PEG), polystyrene with PEG chains attached, crosslinked PEG (e.g., CHEMMATRIX®), PEG-polypropylene glycol network, PEG with polyamide, or PEG with polystyrene), a surface-type support (e.g., pore glass, cellulose fibers, or highly cross-linked polystyrene), a composite (e.g., gel-type polymers supported by rigid matrices), or a combination thereof. In some embodiments, the solid support is a polystyrene resin.

In other embodiments, the carboxyl group (i.e., attached to $(CH_2)_n$) of Formula (II) is activated. Activation of the carboxyl group can occur by reaction with one or more activating compounds. In some embodiments, the activating compounds can speed up the reaction of Formula (II) with W. In some embodiments, the activating compound can be but is not limited to a carbodiimide (e.g., dicyclohexylcarbodiimide (DCC) or diisopropylcarbodiimide (DIC)), a triazol (e.g., 1-hydroxy-benzotriazole (HOBt), 1-hydroxy-7-aza-benzotriazole (HOAt), ethyl 2-cyano-2-(hydroxyimino) acetate (e.g., Oxyma Pure), uronium or phosphonium salt of a non-nucleophilic anion (e.g., tetrafluoroborate or hexafluorophosphate), 2-(1H-benzotriazol-1-yl)-1,1,3,3-tetramethyluronium hexafluorophosphate (HBTU), 1-[Bis(dimethylamino)methylene]-1H-1,2,3-triazolo[4,5-b]pyridinium 3-oxid hexafluorophosphate (HATU), 1H-benzotriazolium 1-[bis(dimethylamino)methylene]-5-chlorohexafluorophosphate (1-),3-oxide (HCTU), O-(Benzotriazol-1-yl)-N,N,N', N'-tetramethyluronium tetrafluoroborate (TBTU), benzotriazol-1-yl-oxytripyrrolidinophosphonium hexafluorophosphate (PyBOP), (1-Cyano-2-ethoxy-2-oxoethylidenaminooxy)dimethylamino-morpholino-carbenium hexafluorophosphate (COMU), or [[(1-cyano-2-ethoxy-2-oxoethylidene)amino]oxy-(dimethylamino)methylidene]-dimethylazanium (TOTU)), a pentafluorophenyl ester (e.g., pentafluorophenyl diphenylphosphinate (FDPP) or 2,2,3,3, 3-Pentafluoro-1-propanol (PFPOH)), or Bis(2-oxo-3-oxazolidinyl)phosphinic chloride (BOP-Cl). In certain embodiments, the activating compound can be DIC, HOBt, or combinations thereof.

The reaction of Formula (II) with the W amino acid sequence results in Formula (III)

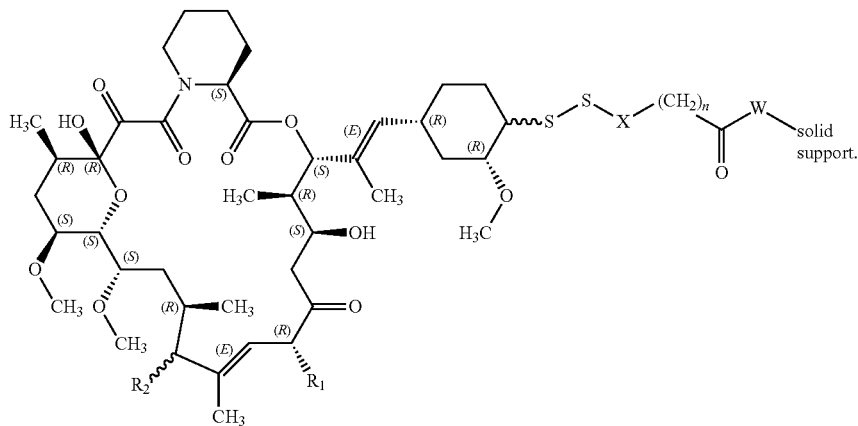

(III)

In some embodiments, Formula (III) is reacted to remove a protecting group from an amino acid (e.g., Lys or an amino acid side chain of Lys) in W (e.g., when W without any protecting groups is identical to Y' or (Y—Z)'). For the sake of simplicity, W with a removed protected group is referred to as W. The reaction conditions for removing a protecting group can be any suitable conditions including but not limited to: for removing an Mtt group on Lys, washing Formula (III) ten times with 1.9% solution of trifluoroacetic acid in dichloromethane, optionally followed by washing five times with N-methylpyrolidone.

In some embodiments, a deprotected group is removed from an amino acid of W (e.g., serine, threonine, asparagine, glutamine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), a backbone of an amino acid of W (e.g., serine, threonine, asparagine, glutamine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), a side group of an amino acid of W (e.g., serine, threonine, asparagine, glutamine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), or a combination thereof. In certain embodiments, an amino acid that has been deprotected is an amino acid that has an amino side group (e.g., lysine, ornithine, 2,4-diaminobutyric acid, 2,3-diaminopropionic acid, 2,2'-diaminopimelic acid, arginine, or histidine). In certain embodiments, the deprotected amino acid is lysine, ornithine, 2,4-diaminobutyric acid, 2,3-diaminopropionic acid, 2,2'-diaminopimelic acid, arginine, or histidine. In certain embodiments, a deprotected side group of an amino acid comprises a maleimide (e.g., lysine, ornithine, 2,4-diaminobutyric acid, 2,3-diaminopropionic acid, 2,2'-diaminopimelic acid, arginine, or histidine), acetate (via, for example, a bromoacetate addition to a hydroxy of an amino acid (e.g., serine, threonine, or tyrosine)), or carboxyl (e.g., aspartic acid or glutamic acid).

In some embodiments, modifications can be made to the deprotected group of the amino acid of W (e.g., serine, threonine, asparagine, glutamine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), to the backbone of the deprotected amino acid of W (e.g., serine, threonine, asparagine, gluta- mine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), to the side group of the deprotected amino acid of W (e.g., serine, threonine, asparagine, glutamine, tyrosine, cysteine, lysine, ornithine, 2,4-diaminobutyric acid, 2,3-diaminopropionic acid, 2,2'-diaminopimelic acid, arginine, histidine, aspartic acid, or glutamic acid), or a combination thereof. In certain embodiments, a modification is made to a deprotected amino acid that has an amino side group (e.g., lysine, ornithine, 2,4-diaminobutyric acid, 2,3-diaminopropionic acid, 2,2'-diaminopimelic acid, arginine, or histidine). In certain embodiments, a modification is made to a deprotected amino acid that is lysine, ornithine, 2,4-diaminobutyric acid, 2,3-diaminopropionic acid, 2,2'-diaminopimelic acid, arginine, or histidine. In certain embodiments, a modification is made to the deprotected side group of the amino acid that is lysine, ornithine, 2,4-diaminobutyric acid, 2,3-diaminopropionic acid, 2,2'-diaminopimelic acid, arginine, or histidine. In certain embodiments, a modification that is made to a deprotected side group of an amino acid comprises a maleimide (e.g., lysine, ornithine, 2,4-diaminobutyric acid, 2,3-diaminopropionic acid, 2,2'-diaminopimelic acid, arginine, or histidine), acetate (via, for example, a bromoacetate addition to a hydroxy of an amino acid (e.g., serine, threonine, or tyrosine)), or carboxyl (e.g., aspartic acid or glutamic acid).

Where W without any protecting groups is identical to Y', a removed protecting group (also referred to as a deprotected group) can then, in some instances, be modified to provide a moiety used to attach Y to Z.

For the sake of simplicity, W with a removed protected group and then modified is referred to as W. The reaction conditions for modifying a deprotected group can be any suitable conditions including but not limited to (a) for adding a maleimide group to a lysine side chain amino, reacting deprotected Formula (III) with 3-fold excess of N-maleoyl-beta-alanine using an equivalent amount of diisopropylcarbodiimide/HOBt for three hours, optionally followed by washing with dichloromethane or (b) for adding a bromoacetemide group to a lysine side chain amino, reacting deprotected Formula (III) with 3-fold excess of bromoacetic acid in dichloromethane using an equivalent amount of diisopropylcarbodiimide for three hours, optionally followed by washing with dichloromethane and methanol.

The solid support is then removed from the C-terminal of W to result in Formula (IV)

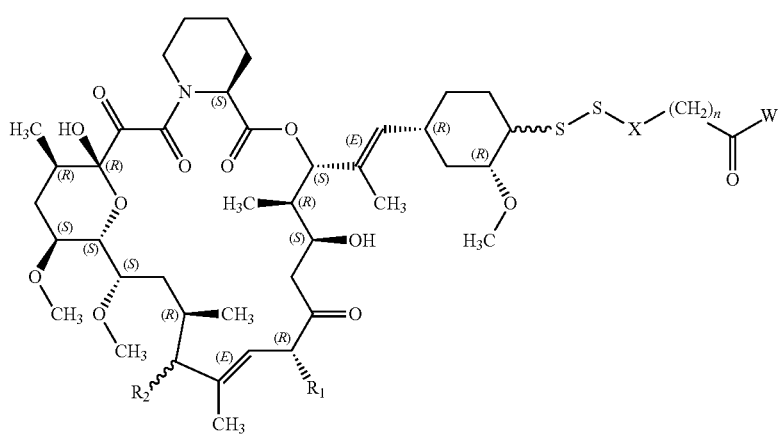

(IV)

Removal of the solid support from W can occur using any suitable method including but not limited to: exposing Formula (IV) to 10 mL of a mixture of DCM:trifluoroacetic acid:1,3 dimethoxybenzene:triisopropylsilane (6.75:2.5:0.5:0.25).

In certain embodiments, all protecting groups are removed from Formula (IV). Removal of the protecting groups can be performed using any suitable method including but not limited to: exposing Formula (IV) to 10 mL of a mixture of DCM:trifluoroacetic acid:1,3 dimethoxybenzene:triisopropylsilane (6.75:2.5:0.5:0.25). In some embodiments, removal from the solid support is performed in same step (e.g., in the same pot) as the removal of the protecting groups, and this step can be accomplished by any suitable method, including, for example those discussed above for removal of the solid support and those discussed above for removal of the protecting groups. The removal of the protecting groups and the removal from the solid support results in (1) Formula (I), if W (without its protecting groups) is (Y—Z)' or Y—Z or (2) Formula (V), if W (without its protecting groups) is Y' or Y.

In some instances, recovered Formula (V) or unrecovered Formula (V) is then attached to Z (e.g., using any suitable conjugation as described herein) to produce Formula (I). In some embodiments, Formula (I) can then be recovered.

Any suitable method can be used to attached Formula (V) to Z including but not limited to adding 2 equivalents of Formula (V) to one equivalent of Z in PBS at pH 7 and incubated at 37° C. for any suitable amount of time such as, for about 30 minutes, about one hour, about overnight, or about 24 hours. The number of equivalents of Formula (V) to one equivalent of Z can be any suitable number, for example, it can vary from less than about equivalent to about 20 equivalents (e.g., about 0.1, about 0.5, about 1, about 2, about 3, about 4, about 5, about 6, about 7, about 8, about 9, about 10, about 11, about 12, about 13, about 14, about 15, about 16, about 17, about 18, about 19, or about 20 equivalents) of Formula (V) to one equivalent of Z.

Recovery can occur using any suitable method including but not limited to HPLC (e.g., reverse phase), LC, precipitation, centrifugation, column chromatography (e.g., size exclusion chromatography or ion exchange chromatography), use of silica gel, or combinations thereof.

The presently-disclosed subject matter is further illustrated by the following specific but non-limiting examples.

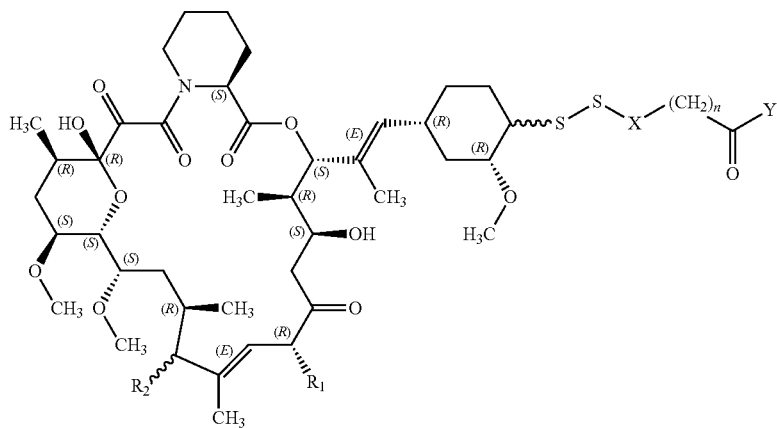

(V)

In some embodiments, Formula (V) or Formula (I) can be recovered.

The following examples may include compilations of data that are representative of data gathered at various times

EXAMPLES

Example 1: Synthesis of Tacrolimus-32-Triflate

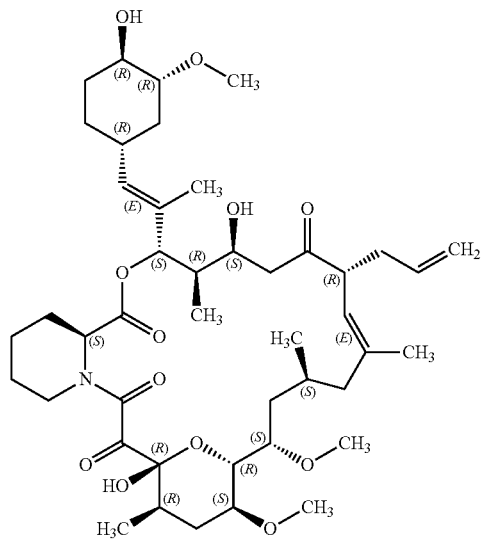

Chemical Formula: $C_{44}H_{69}NO_{12}$
Molecular Weight: 804.02

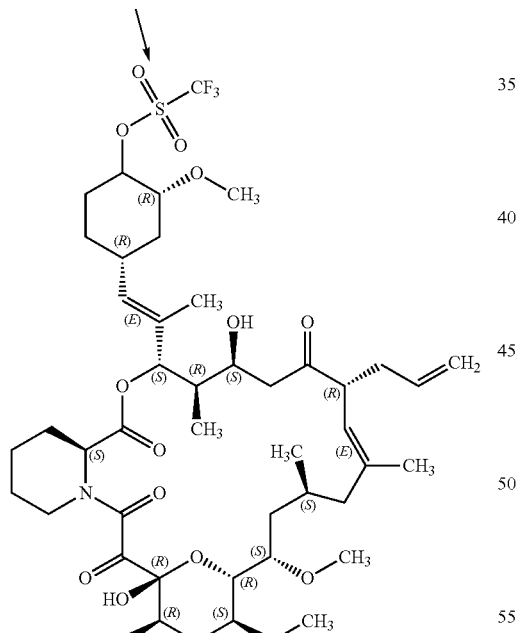

Chemical Formula: $C_{45}H_{68}F_3NO_{14}S$
Molecular Weight: 936.08

Tacrolimus containing a triflate group on the hydroxyl group in position 32 was synthesized. Tacrolimus powder was rigorously dried at 40° C. under high vacuum to remove water. Two g (2.4 mmol) of dried tacrolimus was dissolved in dry dichloromethane (DCM) under argon and then 35 μL (2.49 mmol) of dry 2,6-Lutidine was added. The mixture was cooled to −80° C. and 439 μL (2.49 mmol) of trifluoromethanesulfonic anhydride was added. The reaction was allowed to proceed for about 1 hour at −80° C. The solution was then diluted with ether and washed several times with 10% $KHSO_4$ and dried over $MgSO_4$. The solution was evaporated to dryness and further dried under high vacuum. The resulting powder was used immediately for the next reaction.

Example 2: Synthesis of Tacrolimus-32-Thiol

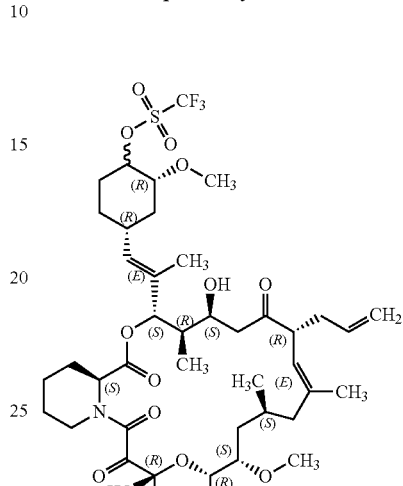

Chemical Formula: $C_{45}H_{68}F_3NO_{14}S$
Molecular Weight: 936.08

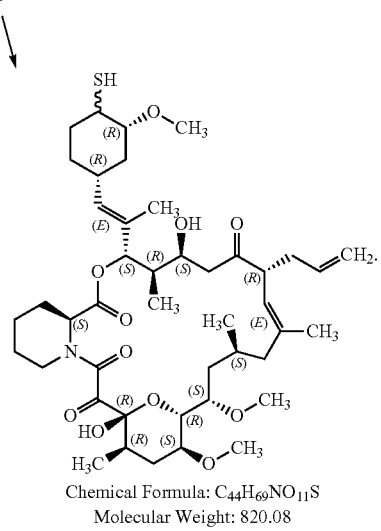

Chemical Formula: $C_{44}H_{69}NO_{11}S$
Molecular Weight: 820.08

The powder from example 1 was dissolved in dry tetrahydrofuran (THF). Then 630 μL (2.49 mmol) of hexamethyldisilathiane in dry THF under argon gas was added to a dry dropping funnel. The solution in the round bottom flask was cooled to −80° C. and the whole reaction vessel was placed in the dark. Then 863 mg (2.49 mmol) of pre-dissolved tetrabutylammonium fluoride hydrate (TBAF) was quickly added to the hexamethyldisilathiane in the dropping funnel and together were added dropwise to the FK506 triflate. The solution mixed overnight at room temperature under argon in the dark.

Thin Layer Chromatography (TLC) the next morning showed complete conversion to the desired product (data not shown). The solution was dried in vacuo, dissolved in ethyl acetate, washed with KHSO₄ and NaCl, and dried over MgSO₄. It was then purified on a silica gel column using 1:1 ethyl acetate:hexane for elution. Fractions containing pure tacrolimus thiol, were pooled and dried and re-dissolved in 7% H₂O in tert-butanol and lyophilized to yield 1 g of tacrolimus-32-thiol. FIG. 1 shows the mass spectrometry data of the isolated tacrolimus-32-thiol.

Example 3: Synthesis of the Methoxycarbonylsulfenyl Derivative of Mercaptopropionic Acid

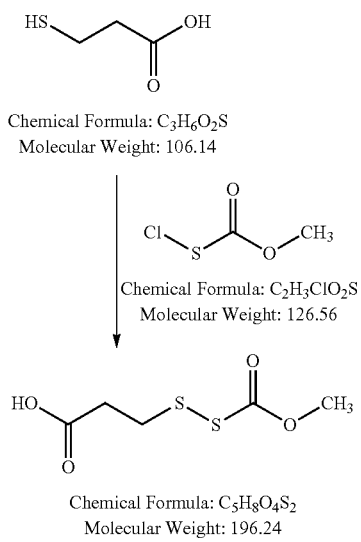

All glassware was dried in the oven overnight. One g (9.42 mmol) of 3-mercaptopropionic acid in dry DCM was added dropwise to methoxycarbonylsulfenyl chloride (937 µl, 9.42 mmol) in 30 ml of dry DCM under argon gas at 0° C. The mixture was stirred overnight at room temperature and solvents removed in vacuo. Further volatiles were removed under high vacuum and gave a residual oil in quantitative yield and 99% purity as judged by proton NMR (data not shown).

Example 4: Synthesis of the Methoxycarbonylsulfenyl Derivative of 4-Mercaptophenylacetic Acid

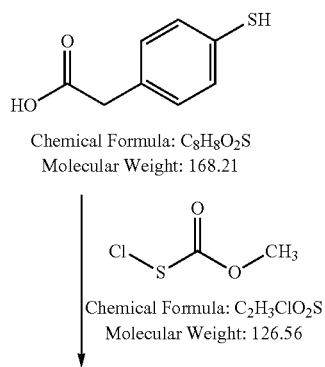

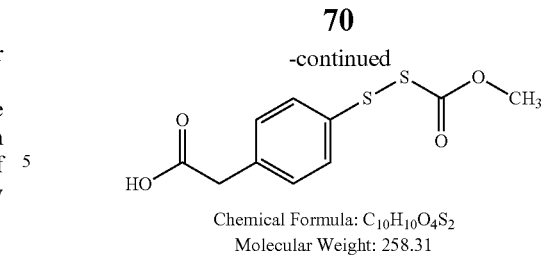

Chemical Formula: C₁₀H₁₀O₄S₂
Molecular Weight: 258.31

All glassware was dried in the oven overnight. One equivalent of 4-mercaptophenylacetic acid in dry DCM was added dropwise to methoxycarbonylsulfenyl chloride (1.1 equivalent) in 30 ml of dry DCM under argon gas at 0° C. The mixture was stirred overnight at room temperature and solvents removed in vacuo. Further volatiles were removed under high vacuum to yield stable crystals in quantitative yield and 99% purity as judged by proton NMR (data not shown).

Example 5: Synthesis of the Methoxycarbonylsulfenyl Derivative of 2-Thiolactic Acid

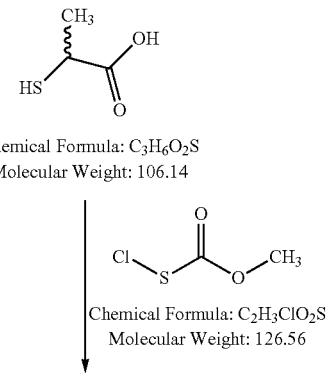

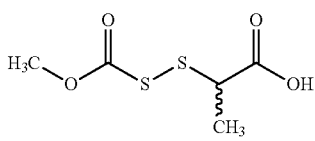

Chemical Formula: C₅H₈O₄S₂
Molecular Weight: 196.24

All glassware was dried in the oven overnight. One equivalent of 4-mercaptophenylacetic acid in dry DCM was added dropwise to methoxycarbonylsulfenyl chloride (1.1 equivalent) in 30 ml of dry DCM under argon gas at 0° C. The mixture was stirred overnight at room temperature and solvents removed in vacuo. Further volatiles were removed under high vacuum to yield stable crystals in quantitative yield and 99% purity as judged by proton NMR (data not shown).

Example 6: Synthesis of Tacrolimus-32-Thiol-Mercaptopropionic Acid Disulfide

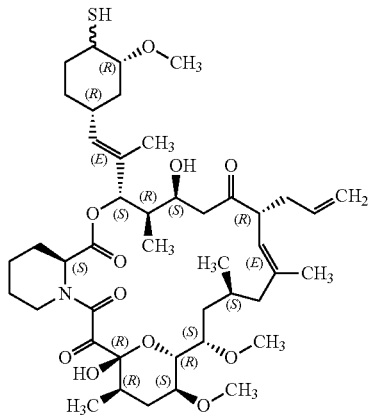

Chemical Formula: $C_{44}H_{69}NO_{11}S$
Molecular Weight: 820.08

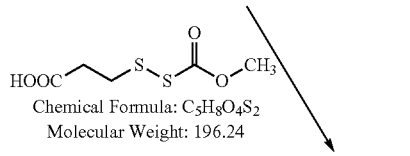

Chemical Formula: $C_5H_8O_4S_2$
Molecular Weight: 196.24

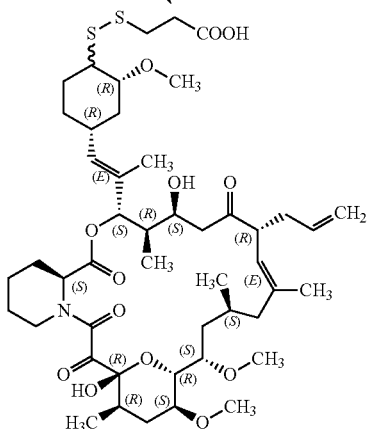

Chemical Formula: $C_{47}H_{73}NO_{13}S_2$
Molecular Weight: 924.21

Tacrolimus-32-thiol prepared in Example 2 (537 mg, 0.66 mmol) was dissolved in methanol (10 ml) to which was added 154 mg (0.66 mmol) of methoxycarbonylsulfenyl-mercaptopropionic acid described in Example 3 and dissolved in methanol (30 ml) in a dry 100 mL round bottom flask under argon at room temperature and 2 drops of triethylamine were added. The solution was stirred overnight at room temperature whereupon a further 50 mg of the methoxycarbonylsulfenylmercaptopropionic acid was added to drive the reaction to completion. The reaction was monitored using TLC, (silica gel, 1:1 ethyl acetate:hexane). When the reaction was observed to be complete, the reaction solution was added to 200 mL of 10% $KHSO_4$ whereupon the disulfide precipitated and was extracted into ethyl acetate and dried over $MgSO_4$. After removal of the solvent, the crude material was purified by elution on a $SiO_2$ column using ethyl acetate (EtOAc):hexane (1:1), followed by methanol:DCM (10:90). Tubes judged to contain pure material by TLC were pooled and evaporated to yield pure tacrolimus-32-thiol-mercaptopropionic acid disulfide. MALDI MS gave a MW of 950.0 (+Na salt) (calc. 924.21).

Example 7: Synthesis of Tacrolimus-32-Thiol-Thiolactic Acid Disulfide

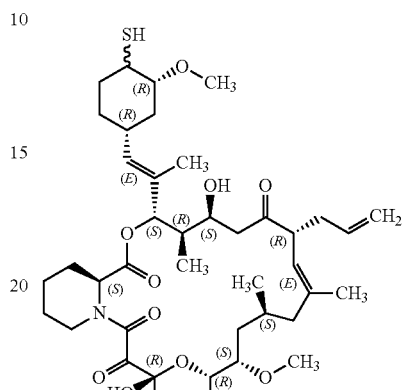

Chemical Formula: $C_{44}H_{69}NO_{11}S$
Molecular Weight: 820.08

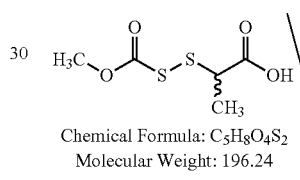

Chemical Formula: $C_5H_8O_4S_2$
Molecular Weight: 196.24

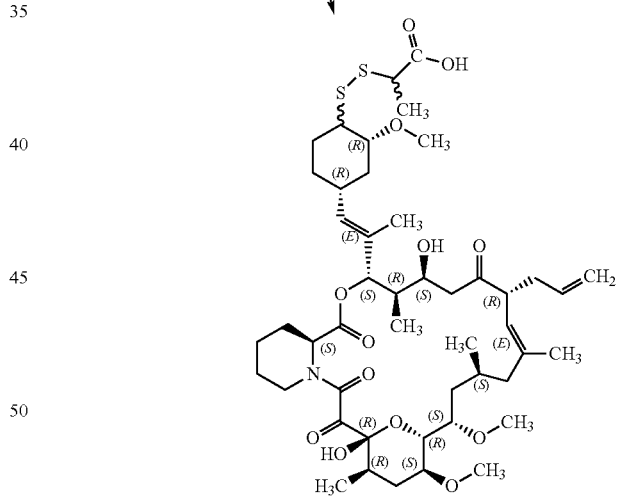

Chemical Formula: $C_{47}H_{73}NO_{13}S_2$
Molecular Weight: 924.21

Tacrolimus-32-thiol prepared in Example 2 (537 mg, 0.61 mmol) was dissolved in methanol (10 ml) to which was added 143 mg (0.73 mmol) methoxycarbonylsulfenylthiolactic acid described in Example 5 and dissolved in methanol (30 ml) in a dry 100 mL RB flask under argon at room temperature followed by addition of 2 drops of triethylamine. The reaction was monitored by SiO2 tlc (1:1 ethyl acetate:hexane. After complete reaction was observed, the reaction solution was added to 200 mL of 10% $KHSO_4$ whereupon the disulfide precipitated and was extracted into ethyl acetate and dried over MgSO$_4$. After removal of the solvent the crude material was purified by elution on a SiO$_2$ column using EtOAc:hexane (1:1), followed by methanol:DCM (10:90). Tubes judged to contain pure material by TLC were pooled and evaporated to yield pure tacrolimus-32-thiol-thiolactic acid disulfide. MALDI MS gave a MW of 947.0 (+Na salt) (calc. 924.2).

Theoretical MW 924.21, Actual+Sodium salt=947.

Example 8: Synthesis of Tacrolimus-32-Thiol-4-Mercaptophenylacetic Acid Disulfide

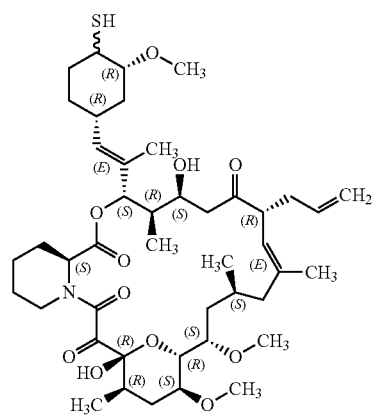

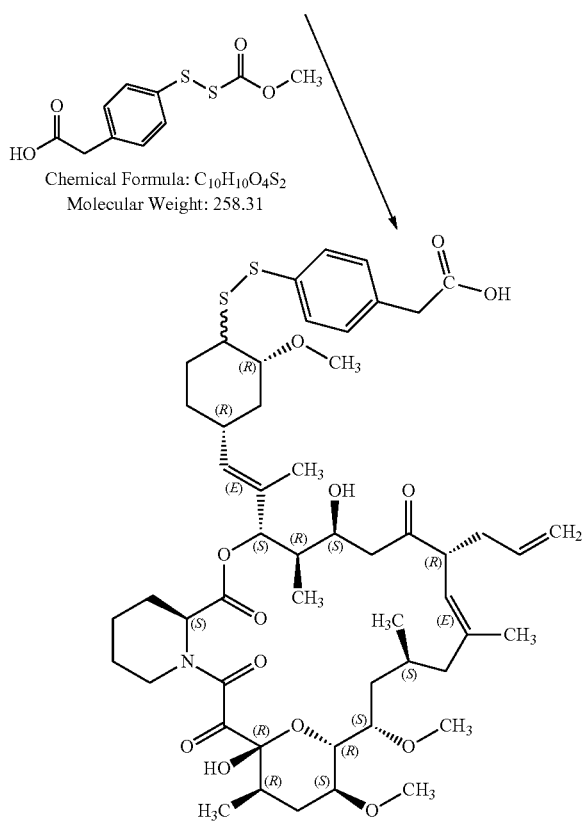

Tacrolimus-32-thiol as prepared in Example 2 (100 mg, 0.12 mmol) was dissolved in methanol (10 ml) to which was added 31.5 mg (0.12 mmol) methoxycarbonylsulfenyl-4-mercaptophenylacetic acid as prepared in Example 5 and dissolved in methanol (30 ml) in a dry 100 mL RB flask under argon at room temperature and 2 drops of triethylamine were added. The reaction was monitored using SiO$_2$ TLC (1:1 ethyl acetate:hexane). When the reaction was complete, the reaction solution was added to 200 mL of 10% KHSO$_4$, whereupon the disulfide precipitated and was extracted into ethyl acetate and dried over MgSO4. After removal of the solvent the crude material was purified by elution on a SiO$_2$ column using EtOAc:hexane (1:1), followed by methanol:DCM (10:90). Tubes judged to contain pure material by TLC were pooled and evaporated to yield pure tacrolimus-32-thiol-thiolactic acid disulfide. MALDI MS gave a MW of 1009.5 (+Na salt) (calc. 986.28).

Example 9: Synthesis of DSer(Trt)-Ser(Trt)-DSer(Trt)-Ser(Trt)-DSer(Trt)-Nle-DTyr(Trt)-Cys(Trt)-Phe-DTrp(Boc)-Lys(Boc)-Thr(Trt)-Cys(Trt)-Thr(Trt)-Rink Amide Resin Commercially available Rink amide polystyrene resin (1 g, 0.5 mmol) was placed in the reaction vessel of a CS Biosystems (CA) automatic peptide synthesizer programmed to perform the following reaction cycle: (a) wash with dimethylformamide (DMF), (b) remove the Fmoc protecting group by mixing with 20% piperidine in DMF (20 min), and (c) couple (18 h) a protected amino acid (1.5 mmole) to the deprotected resin using diisopropylcarbodiimide (DIC) (1.5 mmole) and hydroxybenzotriazole (HOBt) (3.00 mmole) in N-methylpyrolidone, beginning with the C-terminal amino acid. The following protected amino acids were coupled: Fmoc-Thr(Trt), Fmoc-Cys(Trt), Fmoc-Thr(Trt), Fmoc-Lys(Boc), Fmoc-DTrp(Boc), Fmoc-Phe, Fmoc-Cys(Trt), Fmoc-DTyr(Trt), Fmoc-Nle, Fmoc-D-Ser(Trt), Fmoc-Ser(Trt), Fmoc-DSer(Trt), Fmoc-Ser(Trt), Fmoc-D-Ser(Trt). At each stage the Fmoc group on the growing protected peptide chain was removed by mixing with 20% piperidine in DMF (20 min).

Example 10: Synthesis of Tacrolimus-32-Thiol Linked by a Disulfide Bond to the Somatostatin Analog Resin Described in Example 9

The protected peptide resin described in Example 9 (395 mg/$\frac{1}{16}$ mmol) was mixed with tacrolimus-32-thiol-4-mercaptophenylacetic acid disulfide (260 mg, 0.28 mmol), DIC (3 equiv) and HOBt (3 equiv), and allowed to couple to the free peptide resin amino group overnight. After washing with dichloromethane and NMP, the tacrolimus peptide was cleaved from the resin and all protecting groups were removed from amino acid side chains by treatment (2 hours) with 10 ml of a mixture of DCM:trifluoroacetic acid:1,3-dimethoxybenzene:triisopropylsilane (6.75:2.5:0.5:0.25). The resin was filtered and washed with DCM and the filtrate was triturated with ethyl ether and spun down 3 times washing with ethyl ether each time. The white solid was dissolved in 10% acetic acid (250 ml) and titrated with dilute iodine solution until a permanent brown color persisted, indicating disulfide cyclization of the peptide via its 2 Cys residues. The solution was lyophilized and the crude tacrolimus somatostatin conjugate was purified by reverse phase HPLC on a column of C18 silica using a gradient of acetonitrile/0.1% trifluoroacetic acid. Fractions containing pure compound were collected and lyophilized to yield a white powder. MALDI MS gave a MW of 2652 (calc. 2652).

Figure 2:
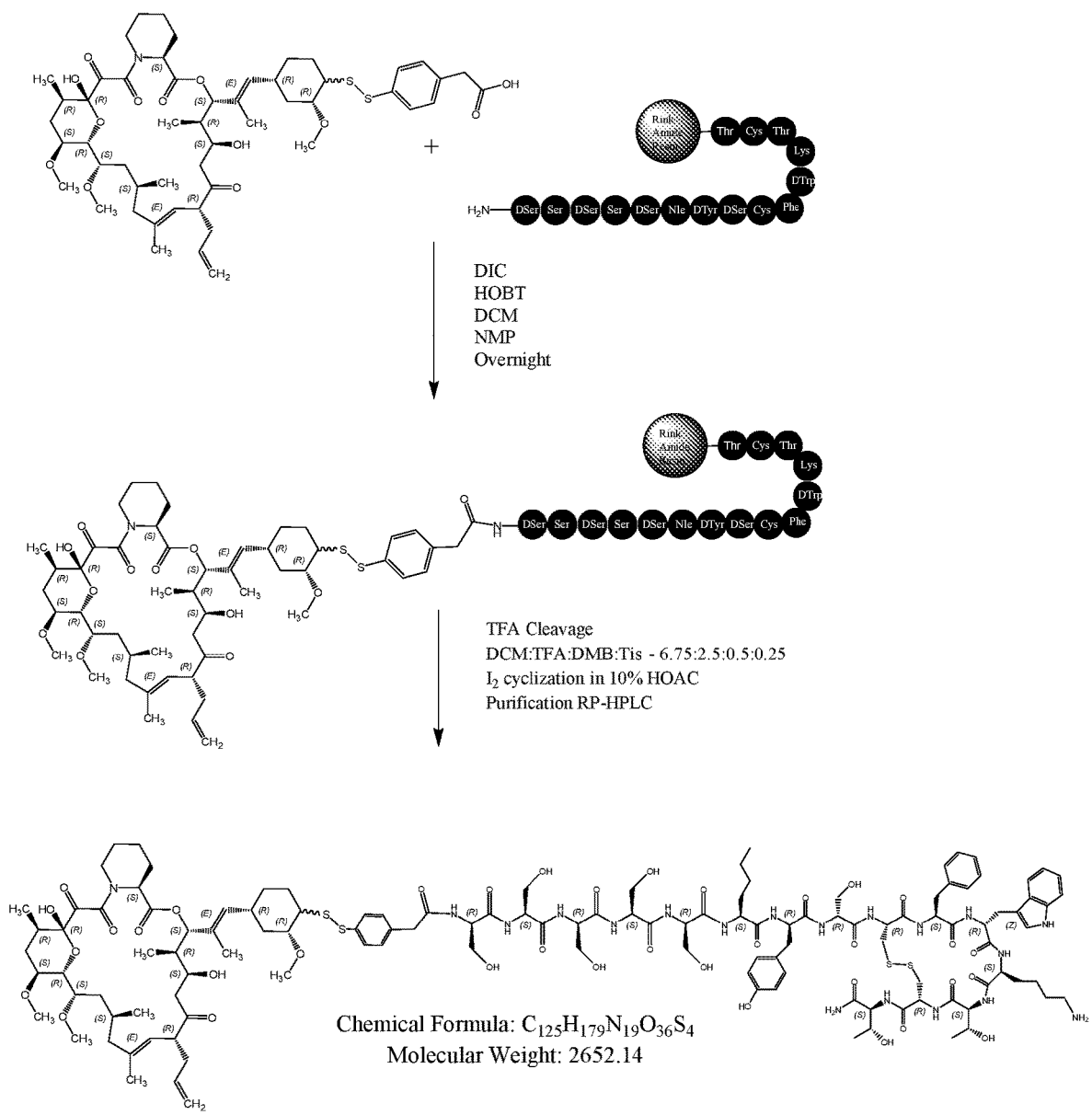
FIG. 2. The synthesis of tacrolimus-32-thiol linked by a disulfide bond to a somatostatin analog resin is illustrated; see also Example 10.

The above described synthesis is illustrated in FIG. 2. CL Example 11: Synthesis of Tacrolimus Disulfide Linked to the Hydrophilic Peptide Sequence DSer-Ser-Thr-Ser-DSer-Lys-DSer-NH$_2$ Incorporating a Bifunctional Maleimide Moiety on it Epsilon Amino Group Suitable for Conjugation to Proteins and Peptides Containing Free Thiol Groups Commercially available Rink amide polystyrene resin (265 mg, ¹⁄₁₆ mmol) was placed in the reaction vessel of a CS Biosystems (CA) automatic peptide synthesizer programmed to perform the following reaction cycle: (a) wash with dimethylformamide (DMF), (b) remove the Fmoc protecting group by mixing with 20% piperidine in DMF (20 min)), and (c) couple (4 h) a protected amino acid (1.5 mmole) to the deprotected resin using diisopropylcarbodiimide (DIC) (1.5 mmole) and hydroxybenzotriazole (HOBt) (3.00 mmole) in N-methylpyrolidone, beginning with the C-terminal amino acid. The following protected amino acids were coupled: Fmoc-DSer(Trt), Fmoc-Lys (Mtt), Fmoc-DSer(Trt), Fmoc-Ser(Trt), Fmoc-Thr(Trt), Fmoc-Ser(Trt), Fmoc-DSer(Trt). At each stage the Fmoc group on the growing protected peptide chain was removed by mixing with 20% piperidine in DMF (20 min). The protected peptide resin containing a free N-terminal amino group was mixed with tacrolimus-32-thiol-3-mercaptoprionic acid disulfide (150 mg, 0.16 mmol), DIC (3 equiv), and HOBt (3 equiv), and allowed to react overnight and then washed with dichloromethane.

Figure 4:
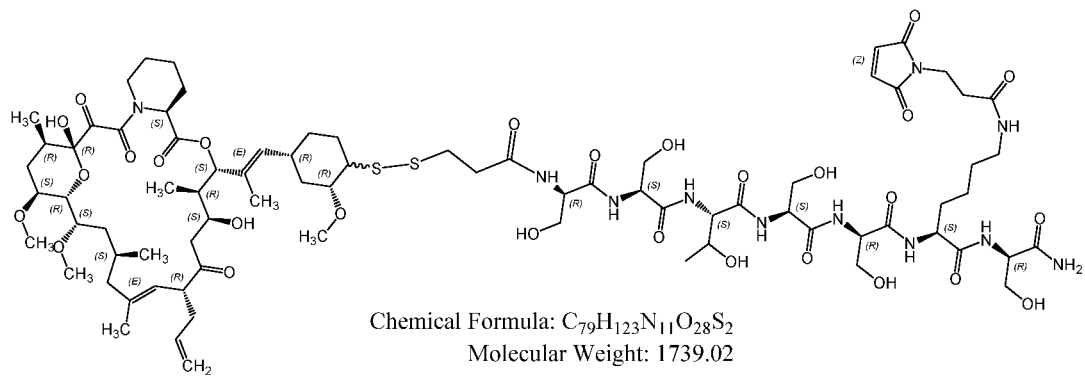
FIG. 4. Structures of tacrolimus-32-SH conjugated to a hydrophilic, water soluble peptide via a cleavable disulfide bond. (A) A heptapeptide is derivatized with a SH reactive maleimide group on the epsilon amino group of a Lys residue. See Examples 11-13. (B) A heptapeptide is derivatized with a SH reactive bromoacetamide group on the epsilon amino group of a Lys residue. See Example 14. (C) An 11-mer peptide is derivatized with a SH reactive maleimide group on the epsilon amino group of a Lys residue. See Example 16. (D) An 11-mer peptide is derivatized with a SH reactive bromoacetamide group on the epsilon amino group of a Lys residue. See Example 17.
Figure 4:
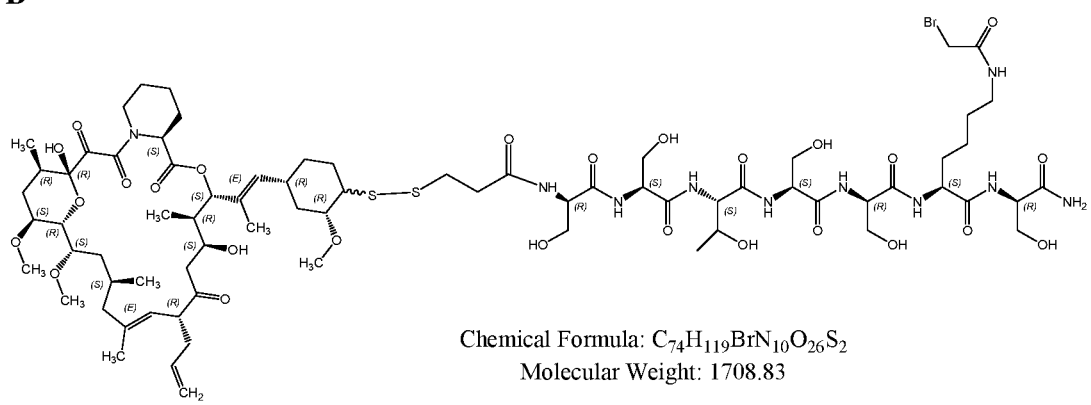
Figure 4:
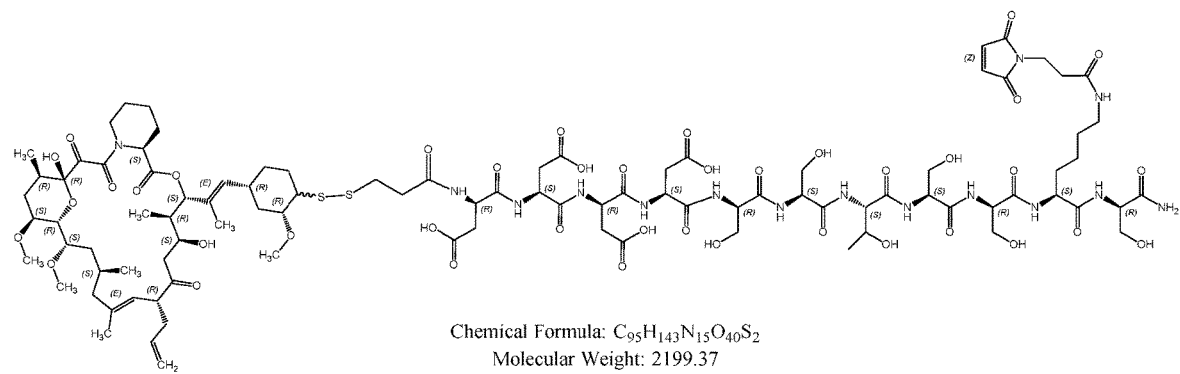
Figure 4:
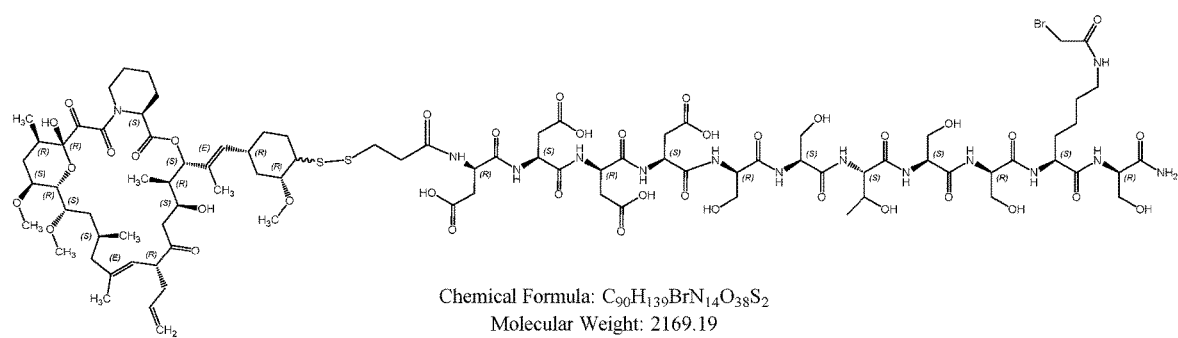

The Mtt group on the epsilon amino group of the Lys residue was removed selectively by washing 10 times with a 1.9% solution of trifluoroacetic acid in dichloromethane followed by washing 5 times with N-methylpyrolidone. The resin was then reacted (3 h) with a 3-fold excess of N-maleoyl-beta-alanine using an equivalent amount of diisopropylcarbodiimide/HOBT. After washing with dichloromethane, the tacrolimus maleimide peptide was cleaved from the resin and all protecting groups were removed from amino acid side chains by treatment (2 hours) with 10 ml of a mixture of DCM:trifluoroacetic acid:1,3-dimethoxybenzene:triisopropylsilane (6.75:2.5:0.5:0.25). The peptide conjugate was precipitated 3 times with ethyl ether and spun down on centrifuge (3000 rpm). The crude tacrolimus peptide maleimide was purified by a combination of reverse phase HPLC on a column of C18 silica using a gradient of acetonitrile/0.1% trifluoroacetic acid followed by purification on silica gel using BAW 4:1:1 (butanol:acetic acid: water). Fractions containing pure compound were collected and lyophilized to yield a white powder. MALDI MS gave a MW of 1761 (+Na salt) (calc. 1739); see FIG. 4A.

Figure 3:
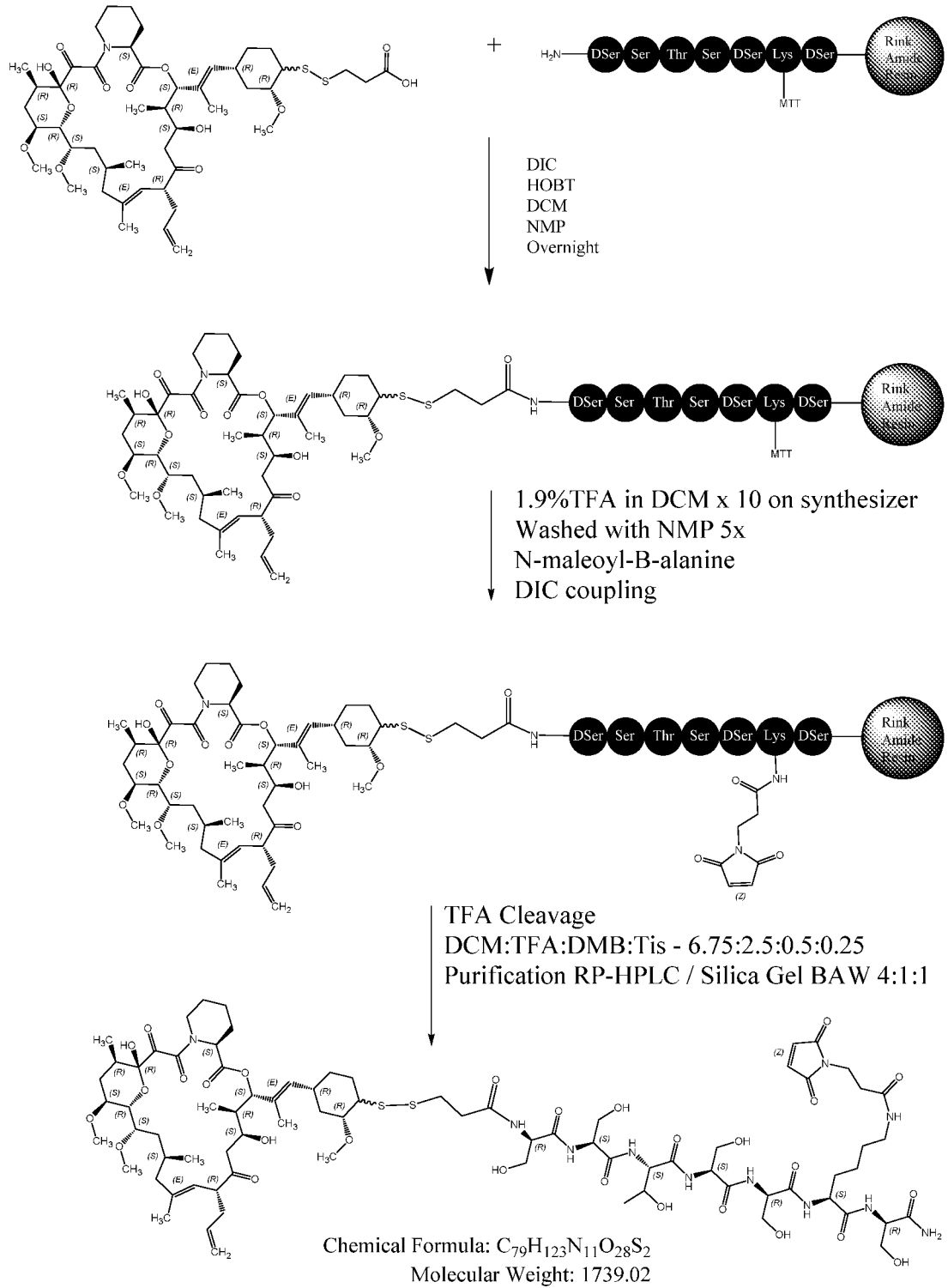
FIG. 3. The synthesis of tacrolimus disulfide linked to a hydrophilic peptide sequence DSer-Ser-Thr-Ser-DSer-Lys-DSer incorporating a maleimide moiety is illustrated; see also Example 11.

The above described synthesis is illustrated in FIG. 3.

Example 12: Water Soluble Tacrolimus Disulfide Hydrophilic Peptide Maleimide Conjugation to the Single Free SH Group Present in Bovine Serum Albumin The tacrolimus disulfide peptide maleimide described in Example 11 (10 mg, ~2 equiv; see FIG. 4A) was added to a solution of bovine serum albumin (200 mg, 3×10⁻⁶ mol) dissolved in 250 microliters of PBS at pH 7 and incubated at 37° C. (overnight). The mixture was applied to a size exclusion column consisting of Sephadex G25 (1.5×100 cm) and eluted with purified water. Fractions were monitored at 280 nm and the peak emerging in the void volume was collected and lyophilized (wt). Analytical HPLC/MS revealed 2 elution peaks; the first peak had an average mass of 66,598 (unconjugated BSA) and the second peak had a mass of 68,491 (conjugated), in roughly equal amounts.

Figure 5:
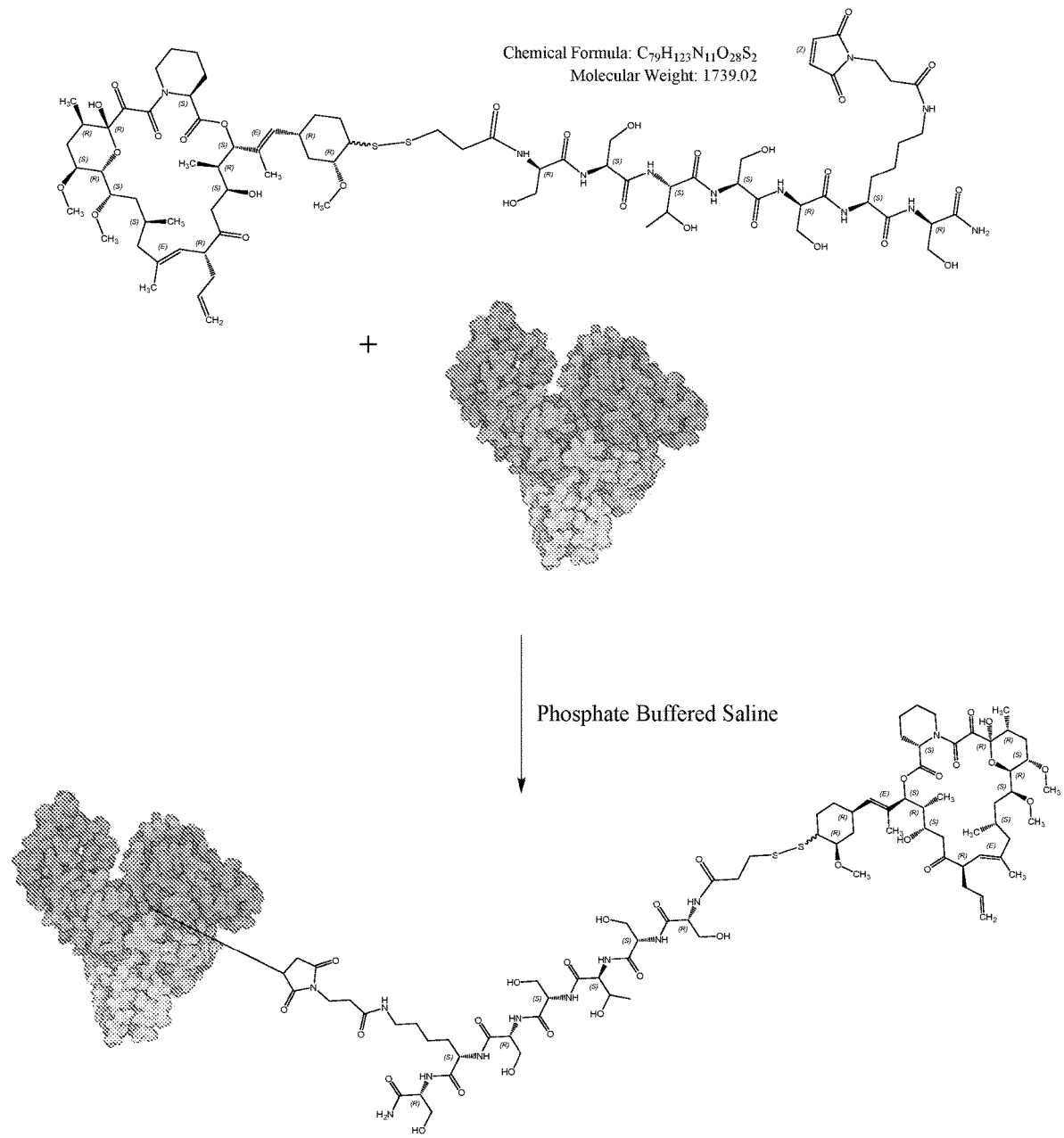
FIG. 5. The conjugation of tacrolimus-disulfide-peptide-maleimide to bovine serum albumin is illustrated; see also Example 13.

The above described synthesis is illustrated in FIG. 5.

Example 13: Separation of Soluble Tacrolimus Disulfide Hydrophilic Peptide Maleimide BSA Conjugate from Unreacted BSA The lyophilized powder described in Example 12 was dissolved employing sonication in 10 ml of a buffer comprising 750 mM ammonium sulfate dissolved in 10 mM phosphate-buffered saline containing 5 mM valeric acid at pH 7.4 (buffer A) and applied to a column (1.5 cm×33 cm) of butyl Sepharose. This was then eluted with a linear gradient of buffer A to buffer B (10 mM phosphate buffered saline containing 5 mM valeric acid). Unconjugated BSA eluted almost immediately followed by the widely separated tacrolimus peptide BSA conjugate. The latter peak was collected, lyophilized, and desalted on a column of Sephadex G25 by elution with 0.1 M ammonium acetate followed by repeated lyophilisation to remove water and ammonium acetate. Mass Spectrometry and analytical HPLC on a C8 reversed phase column using a linear gradient demonstrated the complete removal of free BSA from the conjugate. This tacrolimus peptide BSA conjugate is designated JF-19-42.

Other suitable methods for purifying the conjugate can be used, including but are not limited to those found U.S. Pat. No. 7,307,148 (which is herein incorporated by reference in it entirety).

Example 14: Synthesis of Tacrolimus Disulfide Linked to a Hydrophilic Peptide Sequence DSer-Ser-Thr-Ser-DSer-Lys-DSer-NH$_2$ Incorporating a Bifunctional Bromoacetamide Moiety Suitable for Conjugation to Proteins and Peptides Containing Free Thiol Groups Commercially available Rink amide polystyrene resin (265 mg, ¹⁄₁₆ mmol) was placed in the reaction vessel of a CS Biosystems (CA) automatic peptide synthesizer programmed to perform the following reaction cycle: (a) wash with dimethylformamide (DMF), (b) remove the Fmoc protecting group by mixing with 20% piperidine in DMF (20 min)), and (c) couple (4 h) a protected amino acid (1.5 mmole) to the deprotected resin using diisopropylcarbodiimide (DIC) (1.5 mmole) and hydroxybenzotriazole (HOBt) (3.00 mmole) in N-methylpyrolidone, beginning with the C-terminal amino acid. The following protected amino acids were coupled: Fmoc-DSer(Trt), Fmoc-Lys (Mtt), Fmoc-DSer(Trt), Fmoc-Ser(Trt), Fmoc-Thr(Trt), Fmoc-Ser(Trt), Fmoc-DSer(Trt). At each stage the Fmoc group on the growing protected peptide chain was removed by mixing with 20% piperidine in DMF (20 min). The protected peptide resin containing a free N-terminal amino group was mixed with tacrolimus-32-thiol-3-mercaptoprionic acid disulfide (150 mg, 0.16 mmol), DIC (3 equiv), and HOBt (3 equiv), and allowed to react overnight and then washed with dichloromethane.

The Mtt group on the epsilon amino group of the Lys residue was removed selectively by washing 10 times with a 1.9% solution of trifluoroacetic acid in dichloromethane followed by washing 5 times with N-methylpyrolidone. The resin was then reacted (3 h) with a 3-fold excess of bromoacetic acid in dichloromethane using an equivalent amount of diisopropylcarbodiimide. After washing with dichloromethane and methanol, the tacrolimus bromoacetamide peptide was cleaved from the resin and all protecting groups were removed from amino acid side chains by treatment (2 hours) with 10 ml of a mixture of DCM:trifluoroacetic acid:1,3-dimethoxybenzene:triisopropylsilane (6.75:2.5:0.5:0.25). The peptide conjugate was precipitated 3 times with ethyl ether and spun down on centrifuge (3000 rpm). The crude tacrolimus peptide bromoacetamide was purified by purification on silica gel using BAW 4:1:1 (butanol:acetic acid:water). Fractions containing pure compound were collected and lyophilized to yield a deliquescent white powder. MALDI MS gave a MW of 1708 (JF-19-19; see FIG. 4B).

Example 15: Synthesis of Tacrolimus-Peptide-Bromoacetamide-Human Serum Albumin Conjugate A stock solution (100 mg/ml) of human serum albumin was purchased from Sigma Aldrich. 100 µL of this were added to an Eppendorf tube (0.5 mL). Separately, 1.5 mg of the tacrolimus-peptide-bromoacetamide described in Example 14 was dissolved in 100 µL PBS in a culture tube with gentle heating to provide a still turbid solution, which was added to the HSA solution and incubated in a 37° C. water bath overnight. Aliquots were taken at 3 hours and overnight and assayed on HPLC and MALDI. Reaction progress was judged to be <10% after overnight incubation. After 3 days of incubation little change was noted. This of tacrolimus-peptide-bromoacetamide-human serum albumin conjugate is designated JF-19-51.

Example 16: Synthesis of the More Hydrophilic Tacrolimus-Peptide Conjugate Sequence DAsp-Asp-DAsp-Asp-DSer-Ser-Thr-Ser-DSer-Lys-DSer-NH$_2$ Incorporating a Bifunctional Maleimide Moiety Suitable for Conjugation to Proteins and Peptides Containing Free Thiol Groups Commercially available Rink amide polystyrene resin (265 mg, 1/16 mmol) was placed in the reaction vessel of a CS Biosystems (CA) automatic peptide synthesizer programmed to perform the following reaction cycle: (a) wash with dimethylformamide (DMF), (b) remove the Fmoc protecting group by mixing with 20% piperidine in DMF (20 min)), and (c) couple (4 h) a protected amino acid (1.5 mmole) to the deprotected resin using diisopropylcarbodiimide (DIC) (1.5 mmole) and hydroxybenzotriazole (HOBt) (3.00 mmole) in N-methylpyrolidone, beginning with the C-terminal amino acid. The following protected amino acids were coupled: Fmoc-DSer(Trt), Fmoc-Lys (Mtt), Fmoc-DSer(Trt), Fmoc-Ser(Trt), Fmoc-Thr(Trt), Fmoc-Ser(Trt), Fmoc-DSer(Trt), Fmoc-Asp(tBu), Fmoc-DAsp(tBu), Fmoc-Asp(tBu), Fmoc-DAsp(tBu). At each stage the Fmoc group on the growing protected peptide chain was removed by mixing with 20% piperidine in DMF (20 min). The protected peptide resin containing a free N-terminal amino group was mixed with tacrolimus-32-thiol-3-mercaptoproprionic acid disulfide (150 mg, 0.16 mmol), DIC (3 equiv), and HOBt (3 equiv), and allowed to react overnight and then washed with dichloromethane.

The Mtt group on the epsilon amino group of the Lys residue was removed selectively by washing 10 times with a 1.9% solution of trifluoroacetic acid in dichloromethane followed by washing 5 times with N-methylpyrolidone. The resin was then reacted (3 h) with a 3-fold excess of N-maleoyl-b-alanine using an equivalent amount of diisopropyl-carbodiimide/HOBT. After washing with dichloromethane, the tacrolimus maleimide peptide was cleaved from the resin and all protecting groups were removed from amino acid side chains by treatment (2 hours) with 10 ml of a mixture of DCM:trifluoroacetic acid:1,3-dimethoxybenzene:triisopropylsilane (6.75:2.5:0.5:0.25). The peptide conjugate was precipitated 3 times with ethyl ether and spun down on centrifuge (3000 rpm). The crude tacrolimus peptide maleimide was purified on silica gel using BAW 4:1:1 (butanol:acetic acid:water). Fractions containing pure compound were collected and lyophilized to yield a white powder. MALDI MS gave a MW of 2199 (see FIG. 4C).

Example 17: Synthesis of the More Hydrophilic Tacrolimus-Peptide Conjugate Sequence DAsp-Asp-DAsp-Asp-DSer-Ser-Thr-Ser-DSer-Lys-DSer-NH$_2$ Incorporating a Bifunctional Bromoacetamide Moiety Suitable for Conjugation to Proteins and Peptides Containing Free Thiol Groups Commercially available Rink amide polystyrene resin (265 mg, 1/16 mmol) was placed in the reaction vessel of a CS Biosystems (CA) automatic peptide synthesizer programmed to perform the following reaction cycle: (a) wash with dimethylformamide (DMF), (b) remove the Fmoc protecting group by mixing with 20% piperidine in DMF (20 min)), and (c) couple (4 h) a protected amino acid (1.5 mmole) to the deprotected resin using diisopropylcarbodiimide (DIC) (1.5 mmole) and hydroxybenzotriazole (HOBt) (3.00 mmole) in N-methylpyrolidone, beginning with the C-terminal amino acid. The following protected amino acids were coupled: Fmoc-DSer(Trt), Fmoc-Lys (Mtt), Fmoc-DSer(Trt), Fmoc-Ser(Trt), Fmoc-Thr(Trt), Fmoc-Ser(Trt), Fmoc-DSer(Trt), Fmoc-Asp(tBu), Fmoc-DAsp(tBu), Fmoc-Asp(tBu), Fmoc-DAsp(tBu). At each stage the Fmoc group on the growing protected peptide chain was removed by mixing with 20% piperidine in DMF (20 min). The protected peptide resin containing a free N-terminal amino group was mixed with tacrolimus-32-thiol-3-mercaptoproprionic acid disulfide (150 mg, 0.16 mmol), DIC (3 equiv), and HOBt (3 equiv), and allowed to react overnight and then washed with dichloromethane.

The Mtt group on the epsilon amino group of the Lys residue was removed selectively by washing 10 times with a 1.9% solution of trifluoroacetic acid in dichloromethane followed by washing 5 times with N-methylpyrolidone. The resin was then reacted (3 h) with a 3-fold excess of bromoacetic acid using an equivalent amount of diisopropylcarbodiimide in DCM. After washing with dichloromethane, the tacrolimus bromoacetamide peptide was cleaved from the resin and all protecting groups were removed from amino acid side chains by treatment (2 hours) with 10 ml of a mixture of DCM:trifluoroacetic acid:1,3-dimethoxybenzene:triisopropylsilane (6.75:2.5:0.5:0.25). The peptide conjugate was precipitated 3 times with ethyl ether and spun down on centrifuge (3000 rpm). The crude tacrolimus peptide bromoacetamide was purified on silica gel using BAW 4:1:1 (butanol:acetic acid:water). Fractions containing pure compound were collected and lyophilized to yield a white powder. MALDI MS gave a MW of 2169 (JF-19-52; see FIG. 4D).

Example 18: Conjugation of the More Hydrophilic Asp-Containing Tacrolimus-Disulfide-Peptide-Bromoacetamide to Bovine Serum Albumin A stock solution (0.5 ml) (100 mg BSA/ml) of bovine serum albumin was prepared. Separately, 3 mg of the tacrolimus-peptide-bromoacetamide described in Example 17 (JF-19-52) was dissolved in 100 µL PBS. This tacrolimus peptide bromoacetamide solution was added to the BSA solution and incubated in a 37° C. water bath overnight. Aliquots were taken at 3 hours and overnight and analyzed on HPLC and MALDI and showed >80% BSA conjugation overnight. This tacrolimus-disulfide-peptide-acetamide conjugated to BSA is designated JF-19-53. This Example also demonstrates the effects that the hydrophilicity of the linking peptide has on conjugation yields.

Example 19: Ability of Tacrolimus, tacrolimusSH and its Conjugates to Inhibit IL-2 Release from a Culture of Activated Human T-Cells (Jurkat)

Cells were harvested, washed twice, and re-suspended in serum-free medium at a cell density of $4 \times 10^6$ cells/ml. Fifty µl of cell suspension was then added to each well of 96-well plates followed by 50 µl of tested compounds at different concentration (4×) for 1 hour at 37° C. The cells were stimulated to release IL-2 by adding 50 µl of lectin in PBS (10 µg/ml) and 50 µl of Phorbol in DMSO (100 ng/ml) to each well and continuing overnight incubation. The plates were centrifuged for 10 min at 1500 rpm and supernatants harvested for IL-2 assay using kits purchased from R&D Systems (Minneapolis, Minn.) and following the experimental directions provided.

Figure 6:
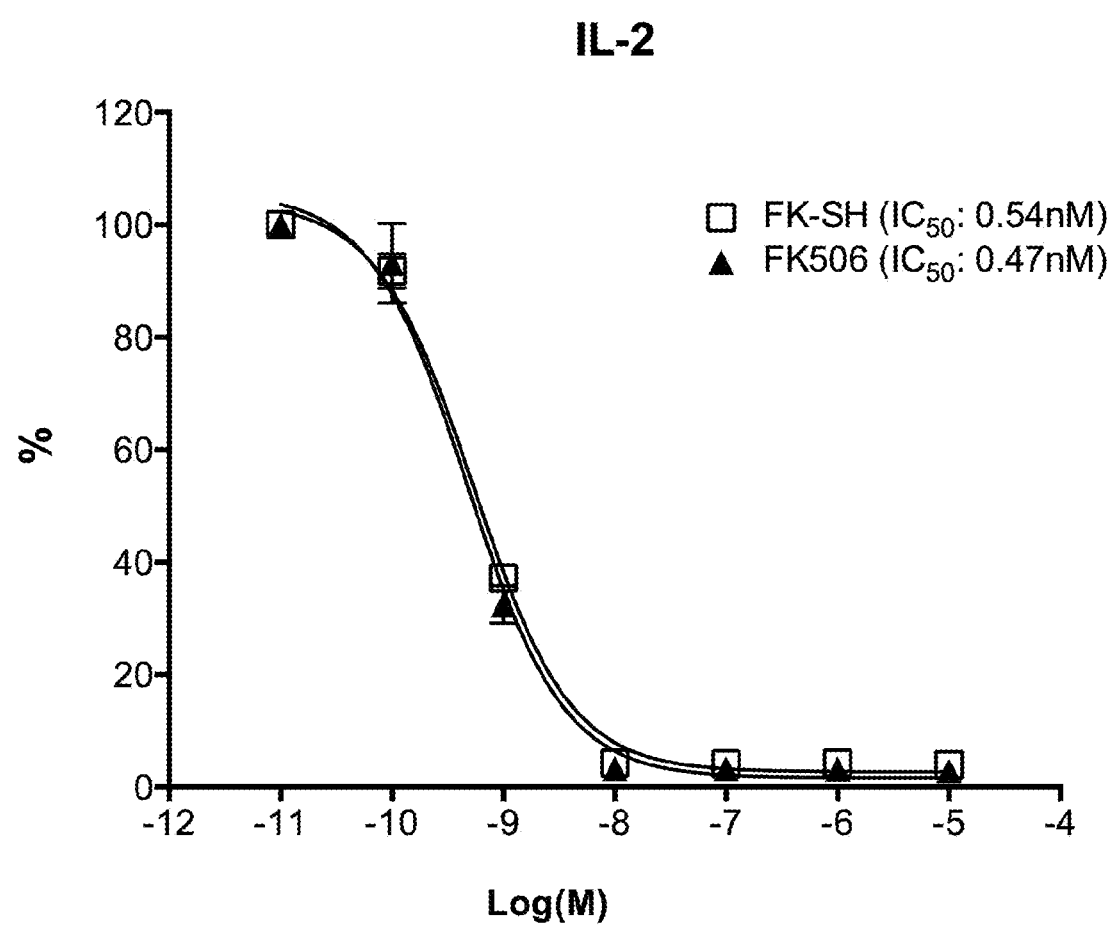
FIG. 6. Inhibition of IL-2 release from human activated T-cells (Jurkat cells)—comparison of FK-506 and tacrolimus-32-SH (FK-SH), which demonstrates equivalent potencies for inhibiting IL-2 release.
Figure 7:
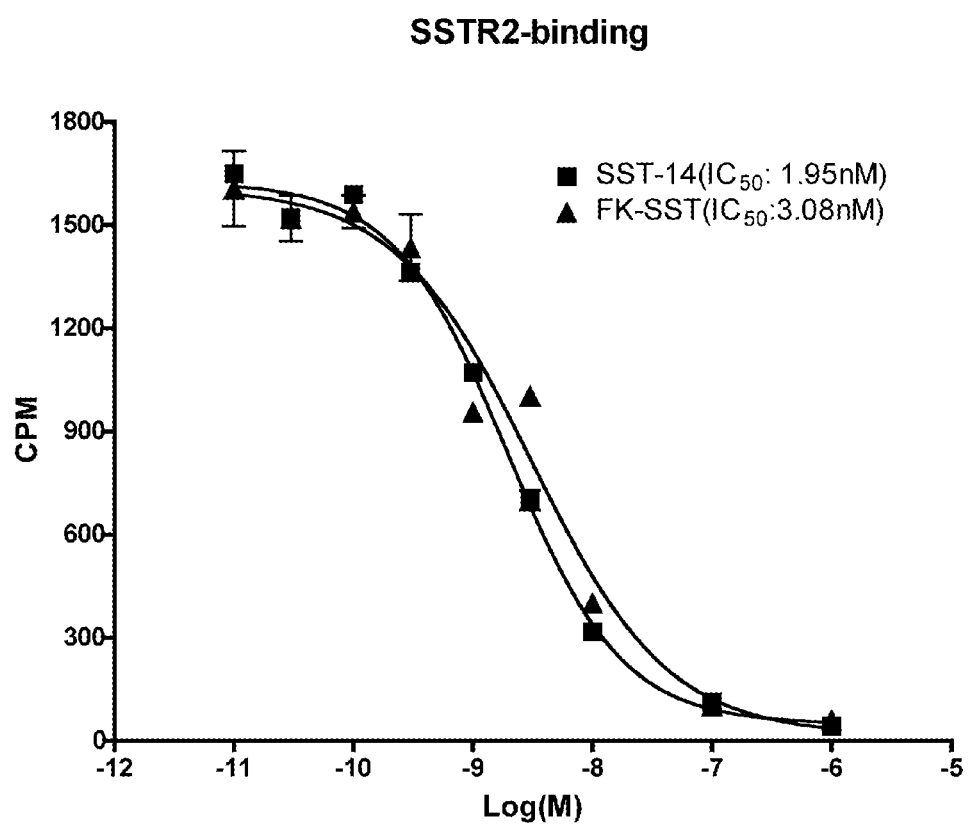
FIG. 7. Comparison of a tacrolimus-SH-somatostatin conjugate with somatostatin itself for binding to somatostatin type 2 receptors which demonstrates equivalent affinities.
Figure 8:
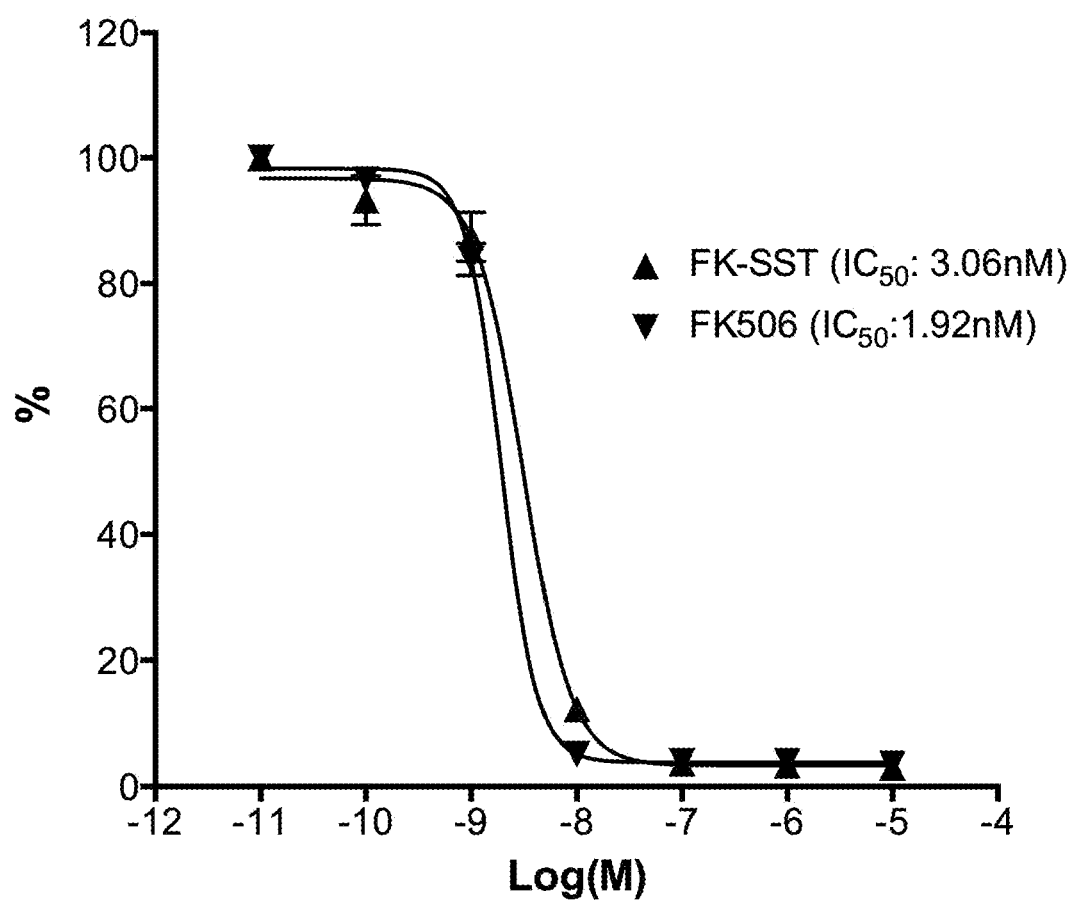
FIG. 8. Inhibition of IL-2 release from human activated T cells—comparison of tacrolimus (FK-506) and tacrolimus-SH-somatostatin conjugate potencies which demonstrates similar potencies.
Figure 9:
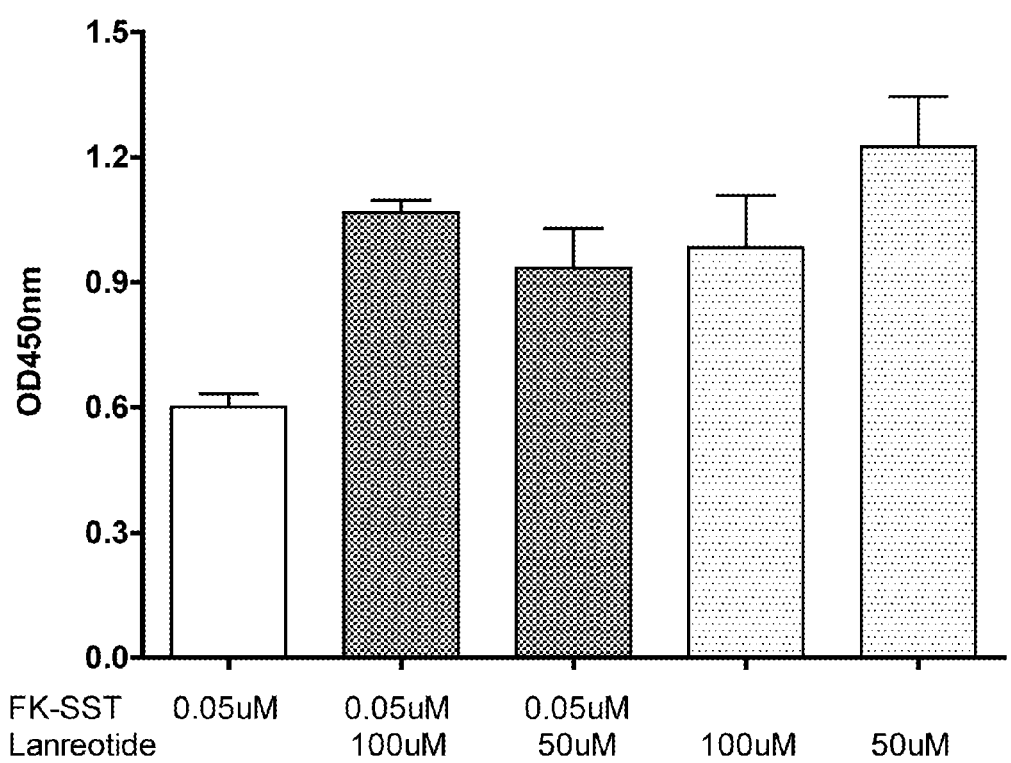
FIG. 9. Blockade of biological activity of tacrolimus-32-SH-somatostatin with a large excess of the somatostatin type 2 agonist, lanreotide, which demonstrates inhibition of drug internalization and stability of the conjugate in cell growth medium.
Figure 10:
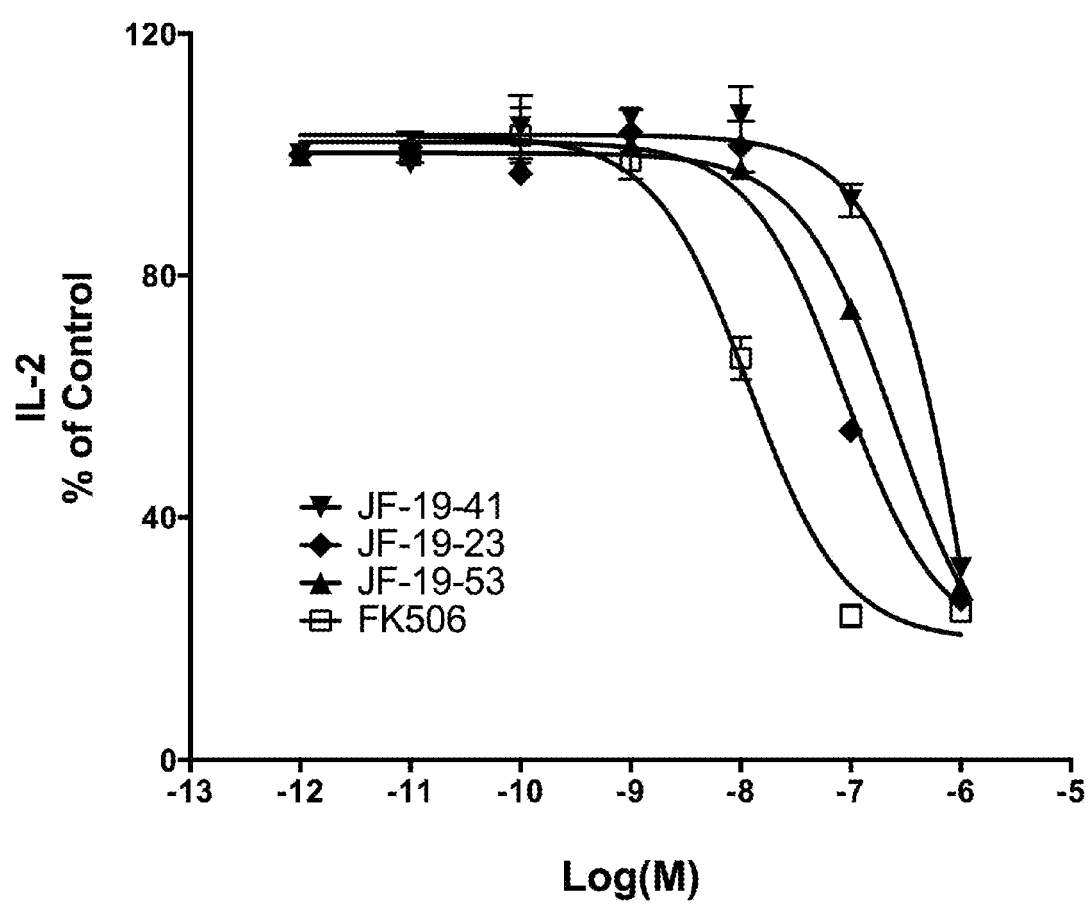
FIG. 10. Inhibition of IL-2 release from human activated T cells—comparison of 3 tacrolimus (FK-506) and tacrolimus-32-SH-hydrophilic peptide-S-albumin conjugates. JF-19-23 is the tacrolimus-S—S-hydrophilic peptide maleonyl BSA conjugate made from the tacrolimus-peptide conjugate described in Example 16. JF-19-42 is the tacrolimus-S—S-hydrophilic peptide maleonyl BSA conjugate described in Example 13. JF-19-53 is the tacrolimus-S—S-hydrophilic peptide alpha-acetyl-BSA conjugate described in Example 18.

Tacrolimus (FK-506) can be a potent inhibitor of release of several important cytokines including IL-2 as demonstrated in FIG. 6. The 32-thiol analog of tacrolimus was virtually equipotent with the parent compound in inhibiting IL-2 release from the cultures of activated T-cells. Activated T-cells have been shown to express internalizing somatostatin type 2 receptors so the binding of the tacrolimus-32-disulfide somatostatin conjugate described in Example 10 was compared to somatostatin itself and was found to have virtually equal affinity to the native peptide (FIG. 7). The tacrolimus disulfide somatostatin conjugate described in Example 10 was compared with tacrolimus itself for the ability to inhibit IL-2 release from activated T-cells and was found to be virtually equipotent (FIG. 8). To demonstrate that the potency of the conjugate was not due to decomposition of the conjugate resulting in the undesirable release of free tacrolimus in buffer, its effect on IL-2 release in the presence of increasing amounts of a potent type 2 receptor analog, lanreotide, was examined (FIG. 9). Large excesses of lanreotide blocked the IL-2 release inhibiting capability of the conjugate thus demonstrating that its inhibitory activity appeared to be mediated via internalizing somatostatrin type 2 receptors. Three of the tacrolimus-32-disulfide-protein conjugates, JF-19-23 (tacrolimus-S—S-hydrophilic peptide maleonyl BSA conjugate made from the tacrolimus-peptide conjugate described in Example 16), JF-19-42 (tacrolimus-S—S-hydrophilic peptide maleonyl BSA conjugate described in Example 13), and JF-19-53 (tacrolimus-S—S-hydrophilic peptide alpha-acetyl-BSA conjugate described in Example 18) were examined for their ability to inhibit IL-2 release from the activated T-cells in culture (FIG. 10) and were found to be more effective at inhibiting IL-2 release relative to tacrolimus (FK-506) itself.

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

In certain instances, sequences disclosed herein are included in publicly-available databases, such as GEN-BANK® and SWISSPROT. Unless otherwise indicated or apparent the references to such publicly-available databases are references to the most recent version of the database as of the filing date of this application.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties or functions sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner Indeed, various modifications of the invention in addition to those described herein will become apparent to those skilled in the art from the foregoing description and the accompanying figures. Such modifications are intended to fall within the scope of the appended claims.

The invention claimed is:

1. A compound of Formula (I)

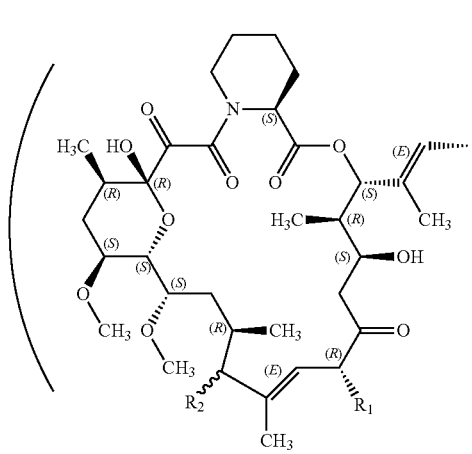
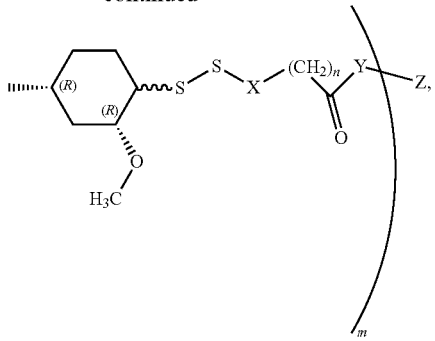

(I)

salts, optical isomers, salts of isomers thereof,
wherein $R_1$ is H, allyl, vinyl, hydroxyl, Cl, Br, F, I, thiol, amino, nitro, cyano, branched or unbranched $C_1$-$C_4$, alkyl, branched or unbranched $C_1$-$C_4$ alkylnoic, phenyl, $C_1$-$C_2$ perfluorinated alkyl, alkyl amino, oxo, carboxy, acetyl, amido, or $C_1$-$C_3$ akloxy;

$R_2$ is H, allyl, vinyl, hydroxyl, Cl, Br, F, I, thiol, amino, nitro, cyano, branched or unbranched $C_1$-$C_4$ alkyl, branched or unbranched $C_1$-$C_4$ alkylnoic, phenyl, $C_1$-$C_2$ perfluorinated alkyl, alkyl amino, oxo, carboxy, acetyl, amido, or $C_1$-$C_3$ akloxy;

X is a substituted or unsubstituted $C_4$-$C_{12}$ conjugated cyclic hydrocarbon or

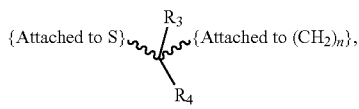

where $R_3$ and $R_4$ can be the same or different and are H or a substituted or unsubstituted, branched or unbranched bivalent $C_1$-$C_{11}$ alkyl;

n is 0, 1, 2, 3, 4, or 5;

m is 1, 2, 3, 4, or 5;

Y is an amino acid sequence of no more than about 30 amino acids; and

Z is targeting amino acid sequence, a stabilizing amino acid sequence, or both.

2. The compound of claim 1, wherein, $R_1$ is H, allyl, ethyl, methyl, or OH.

3. The compound of claim 1, wherein, $R_2$ is H, allyl, ethyl, methyl, or OH.

4. The compound of claim 1, wherein X is a bivalent benzene or a bivalent substituted or unsubstituted $C_4$-$C_{12}$ conjugated cyclic hydrocarbon.

5. The compound of claim 1, wherein X is an unsubstituted $C_1$ or

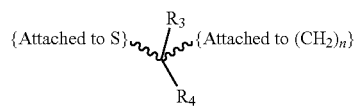

and $R_3$ and $R_4$ can be the same or different and are H or an unsubstituted, branched or unbranched $C_1$-$C_3$ alkyl.

6. The compound of claim 1, wherein n is 0 or 1.

7. The compound of claim 1, wherein m is 1 or 2.

8. The compound of claim 1, wherein the number of amino acids in Y is from about 2 to about 30, from about 4 to about 20, from about 5 to about 17, or from about 7 to about 15.

9. The compound of claim 1, wherein the percentage of D-amino acids in Y is at least about 25%, at least about 50%, at least about 75%, no more than about 25%, no more than about 50%, or no more than about 75%.

10. The compound of claim 1, wherein the percentage of L-amino acids in Y can be at least about 25%, at least about 50%, at least about 75%, no more than about 25%, no more than about 50%, or no more than about 75%.

11. The compound of claim 1, wherein Y has 2, 3, 4, or 5 successive L-amino acids, or has 2, 3, 4, or 5 successive D-amino acids.

12. The compound of claim 1, wherein at least some successive amino acids in Y alternate D-forms and L-forms.

13. The compound of claim 1, wherein Y does not self assemble or have secondary structure.

14. The compound of claim 1, wherein Y is DAsp-Asp-DAsp-Asp-DSer-Ser-Thr-Ser-DSer-Lys-DSer-NH$_2$, DSer-Ser-DSer-Ser-DSer-Nle-DTyr-DSer-Cys-Phe-DTrp-Lys-Thr-Cys-Thr-NH$_2$, or DSer-Ser-Thr-Ser-DSer-Lys-DSer-NH$_2$.

15. The compound of claim 1, wherein Z is no more than about 2500 amino acids, Z has a molecular mass of no more than about 300,000, or both.

16. The compound of claim 1, wherein Z is a protein, a mutated protein, a fragment of the protein or a fragment of the mutated protein.

17. The compound of claim 1, wherein Z targets cells related to inflammation, organs, or combinations thereof.

18. The compound of claim 1, wherein Z targets T cells, cytotoxic T cells, helper T cells, activated T-cells, differentiated T-cells, effector cells, transplanted organs, organs undergoing hyperacute rejection, organs undergoing acute rejection, organs undergoing chronic rejection, organs, tissues or cells associated with autoimmune diseases, organs, tissues or cells associated with inflammation, organs or tissues that are inflamed, or combinations thereof.

19. The compound of claim 1, wherein Z targets transplanted organs, organs undergoing hyperacute rejection, organs undergoing acute rejection, organs undergoing chronic rejection, or combinations thereof.

20. The compound of claim 1, wherein Z targets organs, tissues or cells associated with autoimmune diseases or combinations thereof.

21. The compound of claim 1, wherein Z targets organs, tissues or cells associated with autoimmune diseases or combinations thereof, and the autoimmune disease is arthritis, osteoarthritis, or rheumatoid arthritis.

22. The compound of claim 1, wherein Z is a somatostatin, a somatostatin analog, a bombesin, a bombesin analog, an antibody, a polyclonal antibody, a monoclonal antibody, a polyclonal antibody that targets T-cells, a monoclonal antibody that targets T-cells, a polyclonal antibody that targets Vascular adhesion protein 1, a monoclonal antibody that targets Vascular adhesion protein 1, a peptide that targets inflamed endothelial cells, a peptide that targets integrin $\alpha_v\beta_3$, murine-based antibodies, besilesomab, fanolesomab, sulesomab, antimicrobial peptides, human lactoferrin, ubiquicidin, the ubiquicidin 29-41 peptide fragment, human neutrophil peptide 1-3, annexin-V, IL-2, IL-12, monoclonal antibodies to TNFα, infliximab, adalimumab, monoclonal antibodies to CD4, monoclonal antibodies to CD20, monoclonal antibodies to CD3, KJ1-26 monoclonal antibodies, transferrin, an albumin, human serum albumin (HSA), Domain I of HSA, Domain II of HSA, Domain III of HSA, bovine serum albumin (BSA), an engineered albumin, mutants thereof or fragments thereof.

23. The compound of claim 1, wherein Z is BSA, HSA, or transferrin.

24. The compound of claim 1, wherein Z comprises a stabilizing amino acid sequence.

25. The compound of claim 1, wherein the targeting amino acid sequence overlaps with the stabilizing amino acid sequence, the targeting amino acid sequence encompasses the stabilizing amino acid sequence, the targeting amino acid sequence is the same as the stabilizing amino acid sequence, or the targeting amino acid sequence does not overlap with the stabilizing amino acid sequence.

26. The compound of claim 1, wherein the stabilizing amino acid sequence is an albumin, human serum albumin (HSA), Domain I of HSA, Domain II of HSA, Domain III of HSA, bovine serum albumin (BSA), an engineered albumin, a casein, an insulin, a hemoglobin, a lysozyme, an α-2-macroglobin, a fibronectin, a vitronectin, a fibrinonectin, a lipase, mutants thereof, or fragments thereof.

27. The compound of claim 1, wherein the stabilizing amino acid sequence is BSA or HSA.

28. The compound of claim 1, wherein
(a) $R_1$ is allyl; $R_2$ is methyl; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;
(b) $R_1$ is allyl; $R_2$ is methyl; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;
(c) $R_1$ is allyl; $R_2$ is methyl; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is somatostatin;
(d) $R_1$ is allyl; $R_2$ is methyl; X is bivalent benzene; n is 1; m is 1; Y is DSer-Ser-Thr-Ser-DSer-Lys-DSer-NH$_2$; and Z is BSA or HSA;
(e) $R_1$ is allyl; $R_2$ is methyl; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$;
(f) $R_1$ is allyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;
(g) $R_1$ is allyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;
(h) $R_1$ is allyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is somatostatin;
(i) $R_1$ is allyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is BSA or HSA;
(j) $R_1$ is allyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$;
(k) $R_1$ is ethyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;
(l) $R_1$ is ethyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;
(m) $R_1$ is ethyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is somatostatin;
(n) $R_1$ is ethyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is BSA or HSA;
(o) $R_1$ is ethyl; $R_2$ is H; X is bivalent benzene; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$;
(p) $R_1$ is allyl; $R_2$ is methyl; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;
(q) $R_1$ is allyl; $R_2$ is methyl; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;
(r) $R_1$ is allyl; $R_2$ is methyl; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is somatostatin;
(s) $R_1$ is allyl; $R_2$ is methyl; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is BSA or HSA;
(t) $R_1$ is allyl; $R_2$ is methyl; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$;
(u) $R_1$ is allyl; $R_2$ is H; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;
(v) $R_1$ is allyl; $R_2$ is H; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;
(w) $R_1$ is allyl; $R_2$ is H; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is somatostatin;
(x) $R_1$ is allyl; $R_2$ is H; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is BSA or HSA;
(y) $R_1$ is allyl; $R_2$ is H; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is DSer-Ser-DSer-Ser-DSer-Nle-DTyr-DSer-Cys-Phe-DTrp-Lys-Thr-Cys-Thr-NH$_2$;
(z) $R_1$ is ethyl; $R_2$ is H; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a maleimide; and Z is BSA or HSA;
(aa) $R_1$ is ethyl; $R_2$ is H; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$, where the side-chain amino of Lys in Y is modified with a bromoacetamide; and Z is BSA or HSA;
(bb) $R_1$ is ethyl; $R_2$ is H; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH$_2$; and Z is somatostatin;
(cc) $R_1$ is ethyl; $R_2$ is H; X is unsubstituted $C_1$; n is 1; m is 1; Y is DSer-Ser-Thr-Ser-DSer-Lys-DSer-NH$_2$ or DAsp-Asp-DAsp-Asp-DSer-Ser-Thr-Ser-DSer-Lys-DSer-NH₂; and Z is BSA or HSA; or (dd) R₁ is ethyl; R₂ is H; X is unsubstituted C₁; n is 1; m is 1; Y is DSer-Ser-Thr-Ser-DSer-Lys-DSer-NH₂ or DAsp-Asp-DAsp-Asp-DSer-Ser-Thr-Ser-DSer-Lys-DSer-NH₂; and Z is DSer-Ser-DSer-Ser-DSer-Nle-DTyr-DSer-Cys-Phe-DTrp-Lys-Thr-Cys-Thr-NH₂;

or the compound is

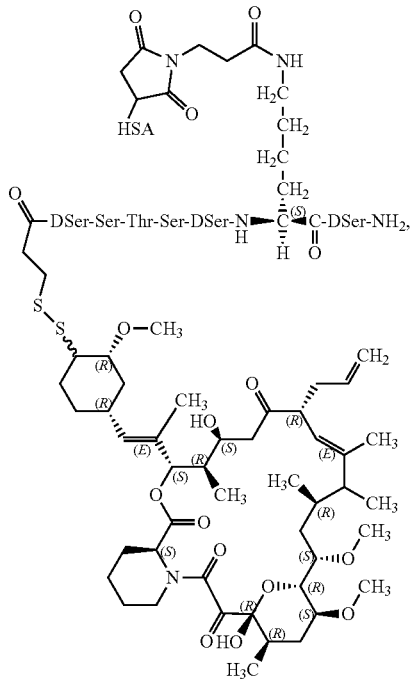

where the attachment to the HSA is via an HSA cysteine thiol or via an HSA amine;

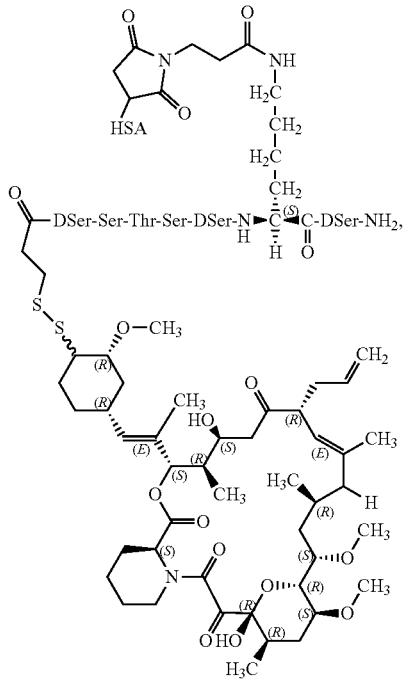

where the attachment to the HSA is via an HSA cysteine thiol or via an HSA amine;

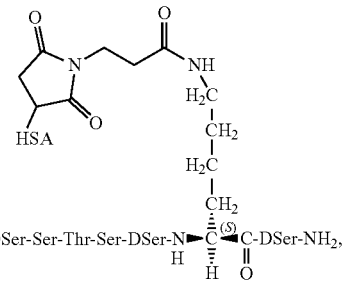

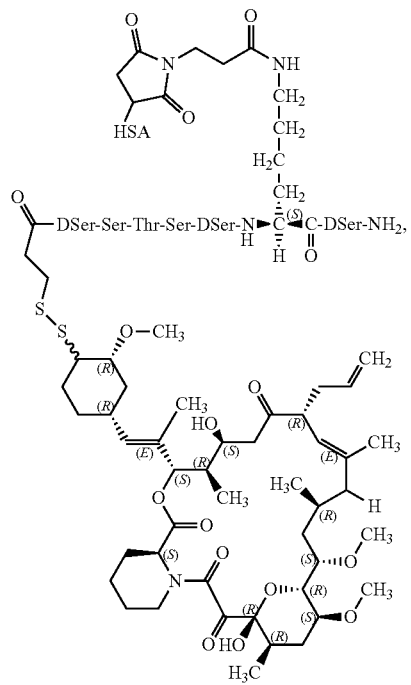

where the attachment to the HSA is via an HSA cysteine thiol or via an HSA amine;

where the attachment to the HSA is via an HSA cysteine thiol or via an HSA amine;

91
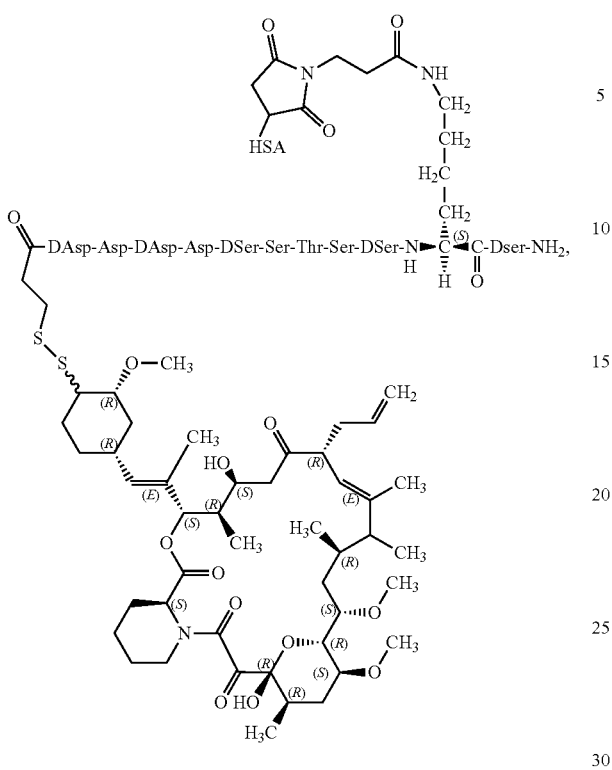
where the attachment to the HSA is via an HSA cysteine thiol or via an HSA amine;
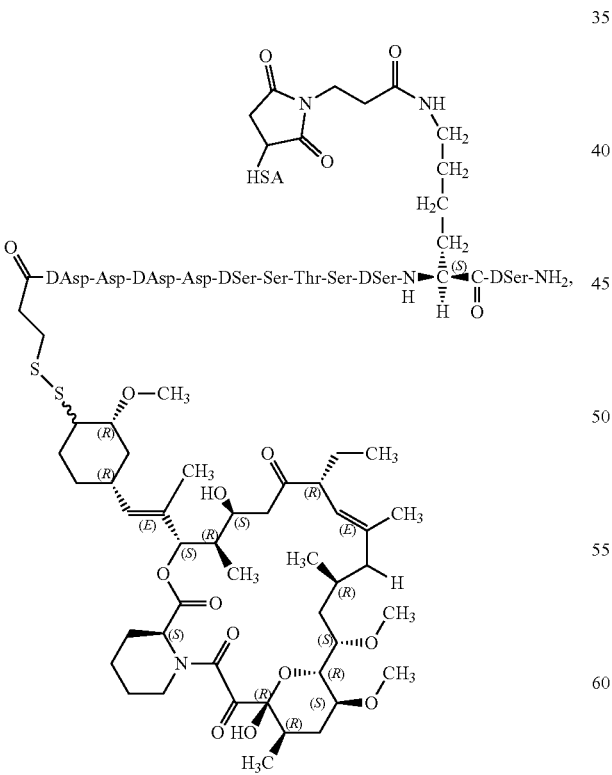
where the attachment to the HSA is via an HSA cysteine thiol or via an HSA amine;
92
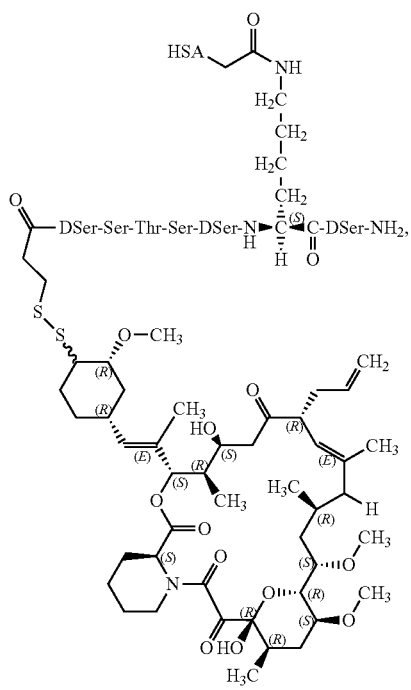
where the attachment to the HSA is via an HSA cysteine thiol or via an HSA amine;
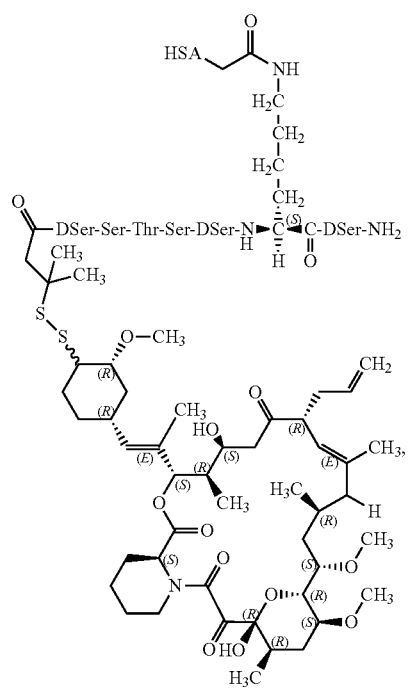
where the attachment to the HSA is via an HSA cysteine thiol or via an HSA amine;

93
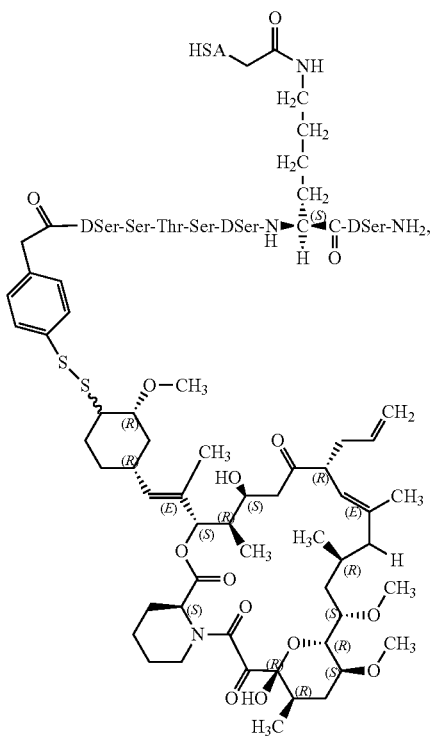
where the attachment to the HSA is via an HSA cysteine thiol or via an HSA amine;
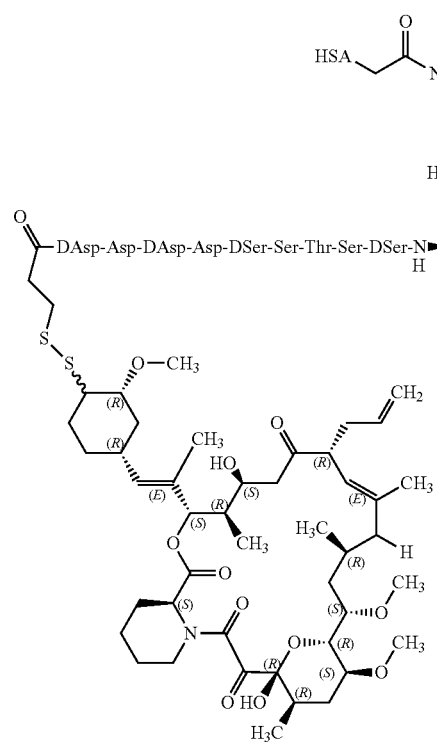
where the attachment to the HSA is via an HSA cysteine thiol or via an HSA amine;
94
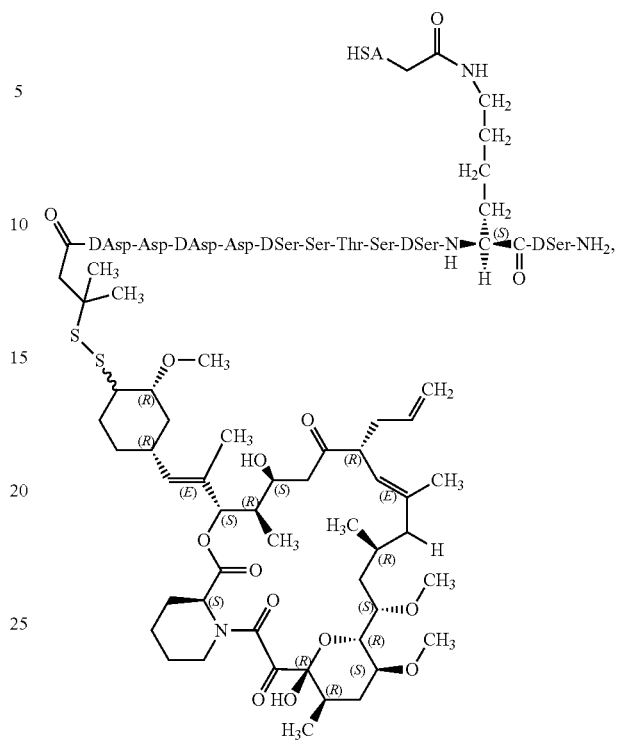
where the attachment to the HSA is via an HSA cysteine thiol or via an HSA amine;
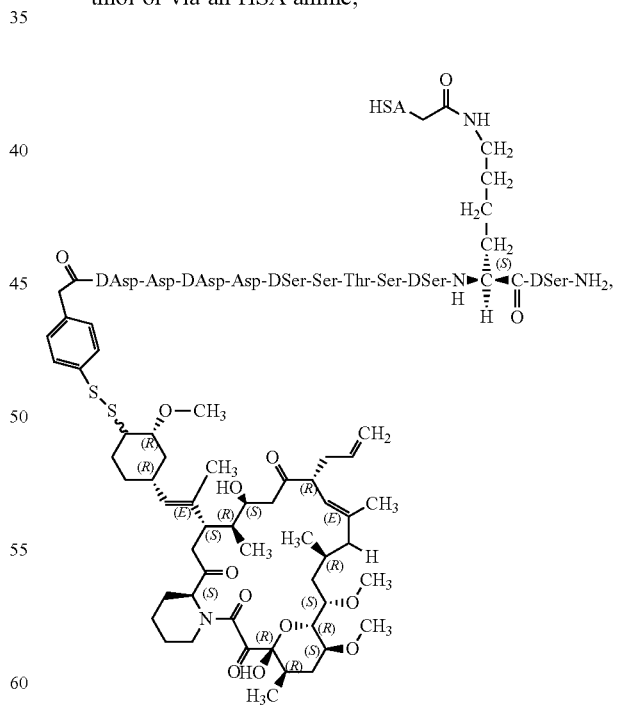
where the attachment to the HSA is via an HSA cysteine thiol or via an HSA amine;

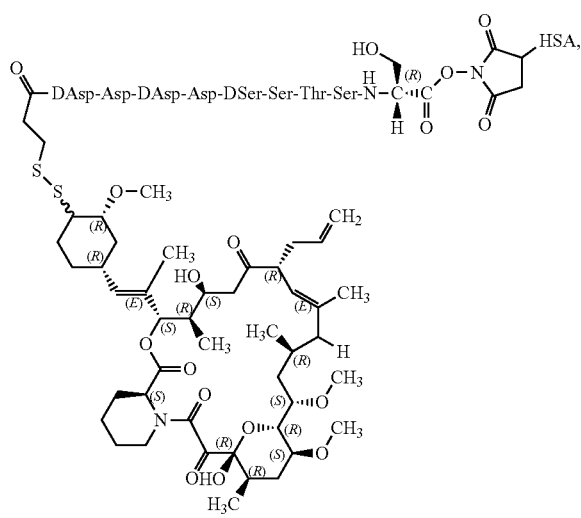

where the attachment to the HSA is via an HSA cysteine thiol or via an HSA amine;

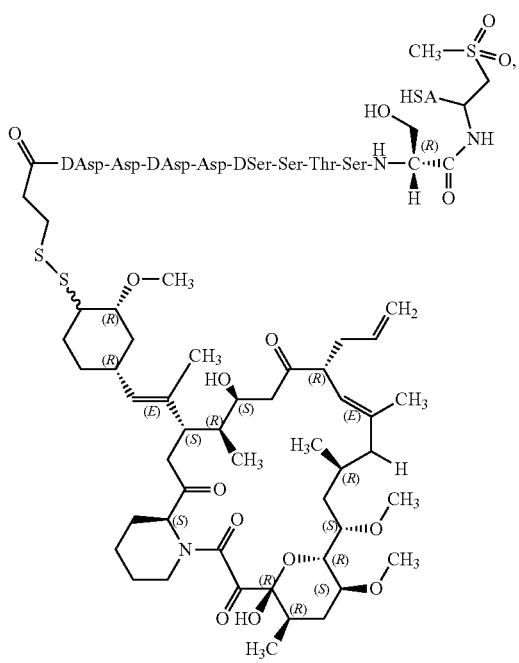

where the attachment to the HSA is via an HSA cysteine thiol or via an HSA amine; or

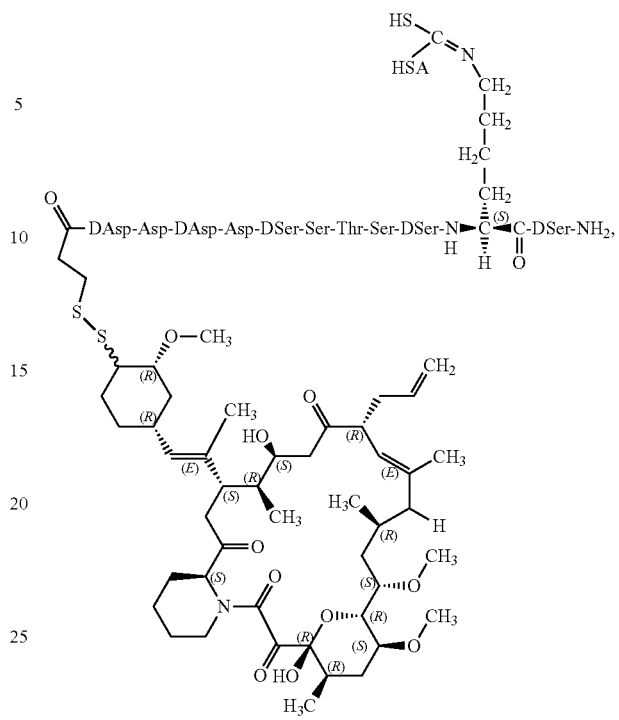

where the attachment to the HSA is via an HSA cysteine thiol or via an HSA amine.

29. A composition comprising a compound of claim 1.

30. The composition of claim 29, wherein the amount of the compound is from about 0.0001% (by weight total composition) to about 99%.

31. A pharmaceutical composition comprising a compound of claim 1.

32. The pharmaceutical composition of claim 31, wherein the amount of the compound is from about 0.0001% (by weight total composition) to about 50%.

33. The pharmaceutical composition of claim 31, further comprising a formulary ingredient.

34. A method for providing an animal with a compound of Formula (I) comprising one or more administrations of one or more compositions to an animal in need thereof, comprising the compound of claim 1, wherein the compositions may be the same or different if there is more than one administration.

35. The method of claim 34, wherein at least one of the one or more compositions further comprises a formulary ingredient.

36. The method of claim 34, wherein at least one of the one or more compositions comprises a pharmaceutical composition.

37. The method of claim 34, wherein at least one of the one or more administrations comprises parenteral administration, a mucosal administration, intravenous administration, subcutaneous administration, topical administration, intradermal administration, oral administration, sublingual administration, intranasal administration, or intramuscular administration.

38. The method of claim 34, wherein if there is more than one administration at least one composition used for at least one administration is different from the composition of at least one other administration.

39. The method of claim 34, wherein the compound of at least one of the one or more compositions is administered to the animal in an amount of from about 0.01 mg/kg animal body weight to about 15 mg/kg animal body weight.

40. The method of claim 34, wherein the animal is a human, a canine, or a primate.

41. A method for treating an animal for an autoimmune disease or for organ rejection, comprising one or more administrations of one or more compositions to an animal in need thereof, comprising the compound of claim 1, wherein (a) the compositions may be the same or different if there is more than one administration, (b) the autoimmune disease is ulcerative colitis, inflammatory bowel disease, Crohn's disease, arthritis, osteoarthritis, or rheumatoid arthritis, and (c) the organ rejection results from an allograft transplantation or a xenograft transplantation.

42. The method of claim 41, wherein at least one of the one or more compositions further comprises a formulary ingredient.

43. The method of claim 41, wherein at least one of the one or more compositions comprises a pharmaceutical composition.

44. The method of claim 41, wherein at least one of the one or more administrations comprises parenteral administration, a mucosal administration, intravenous administration, subcutaneous administration, topical administration, intradermal administration, oral administration, sublingual administration, intranasal administration, or intramuscular administration.

45. The method of claim 41, wherein if there is more than one administration at least one composition used for at least one administration is different from the composition of at least one other administration.

46. The method of claim 41, wherein the compound of at least one of the one or more compositions is administered to the animal in an amount of from about 0.01 mg/kg animal body weight to about 15 mg/kg animal body weight.

47. The method of claim 41, wherein the animal is a human, canine, or a primate.

48. The method of claim 41, wherein the method is for treating organ rejection for a xenograft transplantation.

49. The method of claim 41, wherein the method is for treating organ rejection for an allograft transplantation or for a xenograft transplantation.

50. The method of claim 41, wherein the method is for treating organ rejection for a liver transplant, a kidney transplant, or a heart transplant.

51. The method of claim 41, wherein the method is for treating arthritis, osteoarthritis, or rheumatoid arthritis.

52. The method of claim 41, wherein the animal is susceptible to an autoimmune disease or to an organ rejection.

53. The method of claim 41, wherein the method ameliorates future autoimmune disease or future organ rejection.

54. A method for preparing a compound of claim 1 comprising, (a) reacting a compound of Formula (II)

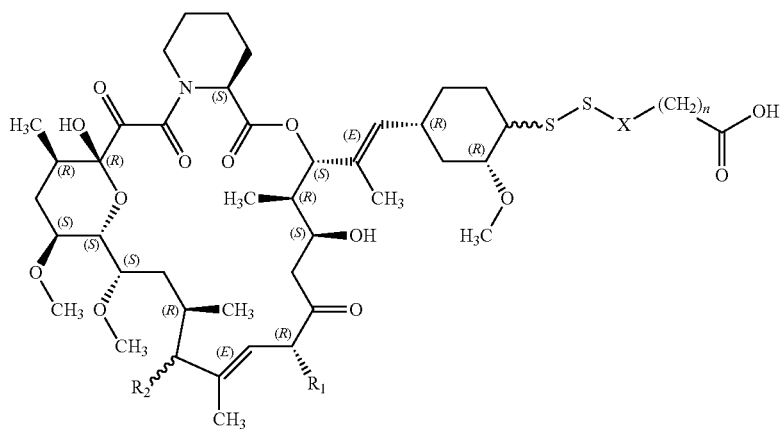

with a W amino acid sequence, where one or more amino acids of W comprises one or more protecting groups and W is attached to a solid support via W's C-terminal amino acid;

(b) optionally removing one or more protecting groups from W;

(c) optionally modifying one of the W amino acids;

(d) cleaving the bond which connects the C-terminal amino acid of W to the solid support to produce a removed compound;

(e) attaching the removed compound to Z, if the removed compound does not include Z; and (f) recovering the compound;

wherein the W amino acid sequence without its one or more protecting groups is identical to (1) a Y' amino acid sequence, (2) a Y amino acid sequence, (3) a (Y—Z)' amino acid sequence, or (4) a Y—Z amino acid sequence;

the Y' amino acid sequence is a pre-modified Y amino acid sequence; and the (Y—Z)' amino acid sequence is a pre-modified Y—Z amino acid sequence.

55. The method of claim 54, further comprising the step of removing all protecting groups from W after step (d) and before step (f).

56. The method of claim 54, further comprising the step of removing all protecting groups from W after step (d) and before step (e).

57. The method of claim 54, further comprising the step of removing all protecting groups from W during step (d).

58. The method of claim 54, wherein the removed compound in step (d) does not include Z.

59. The method of claim 54, wherein step (b) is not optional.

60. The method of claim 54, wherein steps (b) and (c) are not optional.

61. The method of claim 54, wherein steps (b) and (c) are not optional and the modifying of step (c) results in a Lys amino side chain being modified with a maleimide or with a bromoacetamide.

62. The method of claim 54, wherein the solid support is a polystyrene resin.

63. The method of claim 54, wherein the carboxy group adjacent to $(CH_2)_n$ in Formula (II) is activated.

* * * * *